United States Patent
Kotake et al.

(10) Patent No.: US 9,720,323 B2
(45) Date of Patent: Aug. 1, 2017

(54) CHEMICALLY AMPLIFIED POSITIVE RESIST COMPOSITION AND PATTERN FORMING PROCESS

(71) Applicant: Shin-Etsu Chemical Co., Ltd., Tokyo (JP)

(72) Inventors: Masaaki Kotake, Joetsu (JP); Takayuki Fujiwara, Joetsu (JP); Keiichi Masunaga, Joetsu (JP); Daisuke Domon, Joetsu (JP); Satoshi Watanabe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/044,827

(22) Filed: Feb. 16, 2016

(65) Prior Publication Data

US 2016/0246175 A1    Aug. 25, 2016

(30) Foreign Application Priority Data

Feb. 25, 2015   (JP) ................. 2015-035218

(51) Int. Cl.
| | |
|---|---|
| *G03F 7/004* | (2006.01) |
| *G03F 7/039* | (2006.01) |
| *G03F 1/78* | (2012.01) |
| *C07C 381/12* | (2006.01) |
| *C08F 220/20* | (2006.01) |
| *C08F 220/26* | (2006.01) |
| *H01L 21/027* | (2006.01) |
| *G03F 7/20* | (2006.01) |
| *C08F 220/18* | (2006.01) |

(52) U.S. Cl.
CPC .......... *G03F 7/0392* (2013.01); *C07C 381/12* (2013.01); *C08F 220/18* (2013.01); *C08F 220/20* (2013.01); *C08F 220/26* (2013.01); *G03F 1/78* (2013.01); *G03F 7/0045* (2013.01); *G03F 7/0046* (2013.01); *G03F 7/0395* (2013.01); *G03F 7/0397* (2013.01); *G03F 7/2037* (2013.01); *H01L 21/0271* (2013.01); *H01L 21/0274* (2013.01)

(58) Field of Classification Search
CPC ...... G03F 7/004; G03F 7/0045; G03F 7/0046; G03F 7/0392; G03F 7/0395; G03F 7/0397; G03F 7/2037; H01L 21/0271; H01L 21/0274; C07C 381/12; C08F 220/18; C08F 220/26; C08F 220/20

USPC ..... 430/270.1, 322, 325, 329, 942; 526/243, 526/266, 256, 281
See application file for complete search history.

(56) References Cited

U.S. PATENT DOCUMENTS

| | | |
|---|---|---|
| 6,479,210 B2 | 11/2002 | Kinoshita et al. |
| 6,485,883 B2 | 11/2002 | Kodama et al. |
| 6,492,091 B2 | 12/2002 | Kodama et al. |
| 7,527,912 B2 | 5/2009 | Ohsawa et al. |
| 7,923,199 B2 | 4/2011 | Wada |
| 8,361,693 B2 | 1/2013 | Masunaga et al. |
| 8,846,291 B2 | 9/2014 | Utsumi et al. |
| 8,900,791 B2 | 12/2014 | Tsuchimura et al. |
| 8,968,980 B2 * | 3/2015 | Maruyama ............... C07C 65/10 430/270.1 |
| 2010/0310987 A1 | 12/2010 | Maruyama et al. |
| 2013/0029270 A1 | 1/2013 | Hatakeyama |
| 2015/0198876 A1 * | 7/2015 | Domon ................ C07C 61/125 430/285.1 |
| 2016/0131972 A1 * | 5/2016 | Fukushima ........... G03F 7/0045 430/270.1 |
| 2016/0259242 A1 * | 9/2016 | Ohashi ................. G03F 7/0045 |
| 2016/0299428 A1 * | 10/2016 | Masunaga ................ G03F 1/20 |

FOREIGN PATENT DOCUMENTS

| | | |
|---|---|---|
| JP | 11-327143 | 11/1999 |
| JP | 2006-208781 A | 8/2006 |
| JP | 3955384 B2 | 8/2007 |
| JP | 4226803 B2 | 2/2009 |
| JP | 2009-53518 | 3/2009 |
| JP | 4231622 B2 | 3/2009 |
| JP | 2010-100604 A | 5/2010 |
| JP | 2011-22564 A | 2/2011 |
| JP | 2012-123189 A | 6/2012 |
| JP | 5083528 B2 | 11/2012 |
| JP | 2013250433 A * | 12/2013 |

OTHER PUBLICATIONS

Machine translation of JP 2013-250433 (no date).*
Extended European Search Report dated Nov. 2, 2016, issued in counterpart European Application No. 16155252.6. (8 pages).

* cited by examiner

*Primary Examiner* — Amanda C Walke
(74) *Attorney, Agent, or Firm* — Westerman, Hattori, Daniels & Adrian, LLP

(57) ABSTRACT

A resist composition comprising a resin adapted to be decomposed under the action of acid to increase its solubility in alkaline developer and a sulfonium or iodonium salt of nitrogen-containing carboxylic acid has a high resolution. By lithography, a pattern with minimal LER can be formed.

12 Claims, No Drawings

CHEMICALLY AMPLIFIED POSITIVE RESIST COMPOSITION AND PATTERN FORMING PROCESS

CROSS-REFERENCE TO RELATED APPLICATION

This non-provisional application claims priority under 35 U.S.C. §119(a) on Patent Application No. 2015-035218 filed in Japan on Feb. 25, 2015, the entire contents of which are hereby incorporated by reference.

TECHNICAL FIELD

This invention relates to a chemically amplified positive resist composition comprising an onium salt compound of specific structure, and a pattern forming process using the resist composition.

BACKGROUND ART

To meet the recent demand for higher integration in integrated circuits, pattern formation to a finer feature size is required. Acid-catalyzed chemically amplified resist compositions are most often used in forming resist patterns with a feature size of 0.2 µm or less. High-energy radiation such as UV, deep-UV or electron beam (EB) is used as the light source for exposure of these resist compositions. In particular, while EB lithography is utilized as the ultra-fine microfabrication technique, it is also indispensable in processing a photomask blank to form a photomask for use in semiconductor device fabrication.

Polymers comprising a major proportion of aromatic structure having an acidic side chain, for example, polyhydroxystyrene have been widely used in resist materials for the KrF excimer laser lithography. These polymers are not used in resist materials for the ArF excimer laser lithography since they exhibit strong absorption at a wavelength of around 200 nm. These polymers, however, are expected to form useful resist materials for the EB and EUV lithography for forming patterns of finer size than the processing limit of ArF excimer laser because they offer high etching resistance.

Often used as the base polymer in positive resist compositions for EB and EUV lithography is a polymer having an acidic functional group on phenol side chain masked with an acid labile protective group. Upon exposure to high-energy radiation, the acid labile protective group is deprotected by the catalysis of an acid generated from a photoacid generator so that the polymer may turn soluble in alkaline developer. Typical of the acid labile protective group are tertiary alkyl, tert-butoxycarbonyl, and acetal groups. The use of protective groups requiring a relatively low level of activation energy for deprotection such as acetal groups offers the advantage that a resist film having a high sensitivity is obtainable. However, if the diffusion of generated acid is not fully controlled, deprotection reaction can occur even in the unexposed region of the resist film, giving rise to problems like degradation of line edge roughness (LER) and a lowering of in-plane uniformity of pattern line width (CDU).

Attempts were made to ameliorate resist sensitivity and pattern profile in a controlled way by properly selecting and combining components used in resist compositions and adjusting processing conditions. One outstanding problem is the diffusion of acid. Since acid diffusion has a material impact on the sensitivity and resolution of a chemically amplified resist composition, many studies are made on the acid diffusion problem.

Patent Documents 1 and 2 (JP-A 2009-053518 and 2010-100604) describe photoacid generators capable of generating bulky acids like benzenesulfonic acid upon exposure, for thereby controlling acid diffusion and reducing roughness. Since these acid generators are still insufficient in controlling acid diffusion, it is desired to have an acid generator with more controlled diffusion.

Patent Document 3 (JP-A 2011-022564) proposes to control acid diffusion in a resist composition by binding an acid generator capable of generating a sulfonic acid upon light exposure to a base polymer. This approach of controlling acid diffusion by binding recurring units capable of generating acid upon exposure to a base polymer is effective in forming a pattern with reduced LER. However, a problem arises with respect to the solubility in organic solvent of the base polymer having bound therein recurring units capable of generating acid upon exposure, depending on the structure and proportion of the bound units.

Patent Document 4 (JP 5083528) describes a resist composition comprising a resin comprising recurring units having an acetal group and a sulfonium salt capable of generating an acid having a high acid strength such as fluoroalkanesulfonic acid. Regrettably, the pattern obtained therefrom has noticeable LER. This is because the acid strength of fluoroalkanesulfonic acid is too high for the deprotection of an acetal group requiring a relatively low level of activation energy for deprotection. So, even if acid diffusion is controlled, deprotection reaction can occur in the unexposed region with a minor amount of acid that has diffused thereto. The problem arises commonly with sulfonium salts capable of generating benzenesulfonic acids as described in Patent Documents 1 and 2. It is thus desired to have an acid generator capable of generating an acid having an appropriate strength to deprotect an acetal group.

While the aforementioned methodology of generating a bulky acid is effective for suppressing acid diffusion, the methodology of tailoring an acid diffusion regulator (also known as quencher) is also considered effective.

The acid diffusion regulator is, in fact, essential for controlling acid diffusion and improving resist performance. Studies have been made on the acid diffusion regulator while amines and weak acid onium salts have been generally used. The weak acid onium salts are exemplified in several patent documents. Patent Document 5 (JP 3955384) describes that the addition of triphenylsulfonium acetate ensures to form a satisfactory resist pattern without T-top profile, a difference in line width between isolated and grouped patterns, and standing waves. Patent Document 6 (JP-A H11-327143) reports improvements in sensitivity, resolution and exposure margin by the addition of sulfonic acid organic salts or carboxylic acid organic salts. Also, Patent Document 7 (JP 4231622) describes that a resist composition for KrF or EB lithography comprising a PAG capable of generating a fluorinated carboxylic acid is improved in resolution and process latitude such as exposure margin and depth of focus. These systems are based on the mechanism that a salt exchange occurs between a weak acid onium salt and a strong acid (sulfonic acid) generated by another PAG upon exposure, to form a weak acid and a strong acid onium salt. That is, the strong acid (sulfonic acid) having high acidity is replaced by a weak acid (carboxylic acid), thereby suppressing acid-catalyzed decomposition reaction of acid labile group and reducing or controlling the distance of acid diffusion. The onium salt apparently functions as an acid diffusion regulator.

However, a problem of LER arises when a resist composition comprising the foregoing carboxylic acid onium salt or fluorocarboxylic acid onium salt is used in patterning. It would be desirable to have an acid diffusion regulator capable of minimizing LER.

CITATION LIST

Patent Document 1: JP-A 2009-053518
Patent Document 2: JP-A 2010-100604
Patent Document 3: JP-A 2011-022564
Patent Document 4: JP 5083528
Patent Document 5: JP 3955384 (U.S. Pat. No. 6,479,210)
Patent Document 6: JP-A H11-327143
Patent Document 7: JP 4231622 (U.S. Pat. No. 6,485,883)
Patent Document 8: JP 4226803 (U.S. Pat. No. 6,492,091)
Patent Document 9: JP-A 2006-208781
Patent Document 10: JP-A 2012-123189

DISCLOSURE OF INVENTION

An object of the invention is to provide a chemically amplified positive resist composition which exhibits a high resolution and can form a pattern with a minimal LER, and a resist pattern forming process.

In one aspect, the invention provides a chemically amplified positive tone resist composition for high-energy radiation lithography, comprising (A) an onium salt compound and (B) a resin adapted to be decomposed under the action of acid to increase its solubility in alkaline developer. The onium salt compound (A) has the general formula (1) or (2).

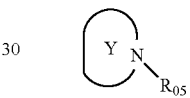
(1)

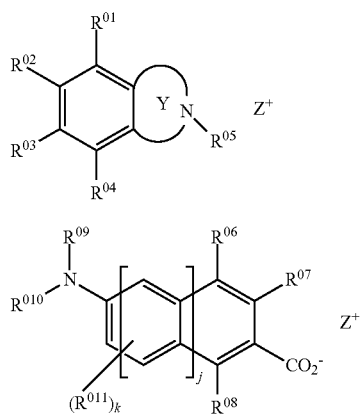
(2)

Herein $R^{o1}$, $R^{o2}$, $R^{o3}$ and $R^{o4}$ are each independently hydrogen, -L-$CO_2^-$, or a straight $C_1$-$C_{20}$, branched or cyclic $C_3$-$C_{20}$ monovalent hydrocarbon group which may be substituted with or separated by a heteroatom, or a pair of $R^{o1}$ and $R^{o2}$, $R^{o2}$ and $R^{o3}$, or $R^{o3}$ and $R^{o4}$ may bond together to form a ring with the carbon atoms to which they are attached. L is a single bond or a straight $C_1$-$C_{10}$, branched or cyclic $C_3$-$C_{20}$ divalent hydrocarbon group which may be substituted with or separated by a heteroatom. $R^{o5}$ is hydrogen or a straight $C_1$-$C_{20}$, branched or cyclic $C_3$-$C_{20}$ monovalent hydrocarbon group which may be substituted with or separated by a heteroatom. $R^{o6}$, $R^{o7}$, $R^{o8}$, $R^{o9}$, $R^{o10}$ and $R^{o11}$ are each independently hydrogen or a straight $C_1$-$C_{20}$, branched or cyclic $C_3$-$C_{20}$ monovalent hydrocarbon group which may be substituted with or separated by a heteroatom, or a pair of $R^{o6}$ and $R^{o7}$ may bond together to form a ring with the carbon atoms to which they are attached, a pair of $R^{o8}$ and $R^{o11}$ may bond together to form a ring with the carbon atoms to which they are attached and any intervening carbon atoms, a pair of $R^{o9}$ and $R^{o10}$ may bond together to form a ring with the nitrogen atom, j is 0 or 1, k is a number in the range: 0≤k≤1 when j=0, or 0≤k≤3 when j=1. $Z^+$ is a sulfonium cation of the general formula (a) or an iodonium cation of the general formula (b).

Herein $R^{100}$, $R^{200}$, and $R^{300}$ are each independently a straight $C_1$-$C_{20}$, branched or cyclic $C_3$-$C_{20}$ monovalent hydrocarbon group which may be substituted with or separated by a heteroatom, or any two or more of $R^{100}$, $R^{200}$, and $R^{300}$ may bond together to form a ring with the sulfur atom. $R^{400}$ and $R^{500}$ are each independently a straight $C_1$-$C_{20}$, branched or cyclic $C_3$-$C_{20}$ monovalent hydrocarbon group which may be substituted with or separated by a heteroatom. The partial structure represented by the formula:

is a cyclic structure having the intervening nitrogen atom in which a hydrogen atom bonded to a cyclic structure-forming carbon atom may be replaced by a straight $C_1$-$C_{20}$, branched or cyclic $C_3$-$C_{20}$ monovalent hydrocarbon group or -L-$CO_2^-$, or in which a cyclic structure-forming carbon atom may be replaced by sulfur, oxygen or nitrogen. It is noted that one substituent: -L-$CO_2^-$ is essentially included in formula (1).

The resin (B) comprises recurring units having the general formula (U-1).

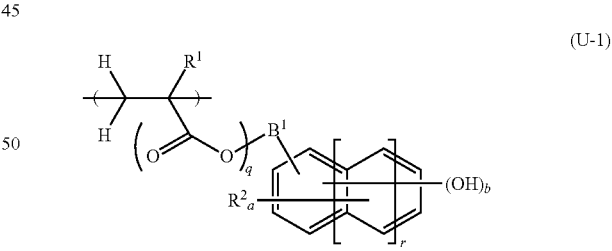
(U-1)

Herein q is 0 or 1, r is an integer of 0 to 2, $R^1$ is hydrogen, fluorine, methyl or trifluoromethyl, $R^2$ is each independently hydrogen or $C_1$-$C_6$ alkyl, $B^1$ is a single bond or $C_1$-$C_{10}$ alkylene group which may contain an ether bond, "a" is an integer satisfying a≤5+2r−b, and "b" is an integer of 1 to 3.

When the resist composition thus constructed is used in lithography to form a pattern, the onium salt compound acts so as to effectively control acid diffusion upon exposure in the pattern forming process, which leads to the advantages of improved resolution in the processing of a resist film to form a pattern and minimal LER of the resulting pattern. The recurring units of formula (U-1) are not only adapted to turn highly soluble in alkaline developer, but also effective for enhancing the adhesion of a resist film to an underlying processable substrate.

In a preferred embodiment, the resin (B) further comprises recurring units having the general formula (U-2).

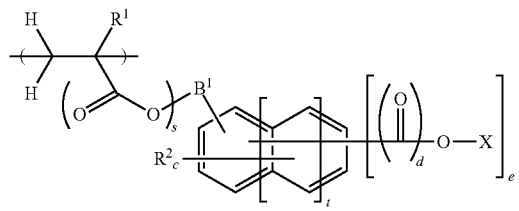

(U-2)

Herein a is 0 or 1, t is an integer of 0 to 2, $R^1$, $R^2$ and $B^1$ are as defined above, c is an integer satisfying c≤5+2t−e, d is 0 or 1, and e is an integer of 1 to 3. X is an acid labile group when e is 1. X is hydrogen or an acid labile group when e is 2 or 3, at least one X being an acid labile group.

In the resist composition thus constructed, since the acid labile group, i.e., protective group in the recurring unit (U-2) undergoes deprotection reaction under the action of acid, a better solubility in alkaline developer is available.

In a preferred embodiment, the resin (B) further comprises recurring units of at least one type selected from units having the general formulae (U-3) and (U-4).

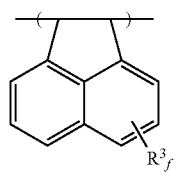

(U-3)

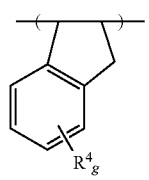

(U-4)

Herein f is an integer of 0 to 6, $R^3$ is each independently hydrogen, an optionally halo-substituted $C_1$-$C_6$ alkyl or primary or secondary alkoxy group, or an optionally halo-substituted $C_1$-$C_7$ alkylcarbonyloxy group, g is an integer of 0 to 4, and $R^4$ is each independently hydrogen, an optionally halo-substituted $C_1$-$C_6$ alkyl or primary or secondary alkoxy group, or an optionally halo-substituted $C_1$-$C_7$ alkylcarbonyloxy group.

The recurring units (U-3) and (U-4) serve to improve etch resistance.

In a preferred embodiment, the resin (B) further comprises recurring units of at least one type selected from units having the general formulae (a1), (a2) and (a3).

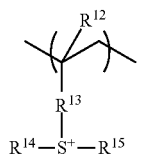

(a1)

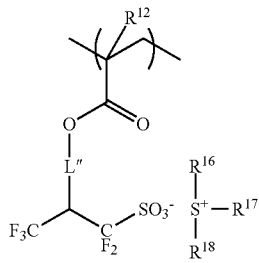

(a2)

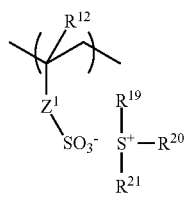

(a3)

Herein $R^{12}$ is each independently hydrogen or methyl. $R^{13}$ is a single bond, phenylene, —O—$R^{22}$—, or —C(=O)—$Z^2$—$R^{22}$—, wherein $Z^2$ is oxygen or NH, $R^{22}$ is a straight, branched or cyclic $C_1$-$C_6$ alkylene, alkenylene or phenylene group, which may contain a carbonyl (—CO—), ester (—COO—), ether (—O—), or hydroxyl moiety. $L''$ is a single bond or —$Z^3$—C(=O)—O—, wherein $Z^3$ is a straight, branched or cyclic $C_1$-$C_{20}$ divalent hydrocarbon group which may be substituted with or separated by a heteroatom. $Z^1$ is a single bond, methylene, ethylene, phenylene, fluorinated phenylene, —O—$R^{23}$— or —C(=O)—$Z^4$—$R^{23}$—, wherein $Z^4$ is oxygen or NH, $R^{23}$ is a straight, branched or cyclic $C_1$-$C_6$ alkylene, alkenylene or phenylene group, which may contain a carbonyl, ester, ether, or hydroxyl moiety. $M^-$ is a non-nucleophilic counter ion. $R^{14}$, $R^{15}$, $R^{16}$, $R^{17}$, $R^{18}$, $R^{19}$, $R^{20}$, and $R^{21}$ are each independently a straight $C_1$-$C_{20}$, branched or cyclic $C_3$-$C_{20}$ monovalent hydrocarbon group in which a hydrogen atom may be substituted by a heteroatom selected from oxygen, sulfur, nitrogen and halogen or in which a heteroatom selected from oxygen, sulfur and nitrogen may intervene, so that a hydroxyl, cyano, carbonyl, ether bond, ester bond, sulfonic acid ester bond, carbonate bond, lactone ring, sultone ring, carboxylic anhydride or haloalkyl group may form or intervene, or a pair of $R^{14}$ and $R^{15}$ may bond together to form a ring with the sulfur atom, or any two or more of $R^{16}$, $R^{17}$ and $R^{18}$ or any two or more of $R^{19}$, $R^{20}$ and $R^{21}$ may bond together to form a ring with the sulfur atom.

The resist composition thus constructed has advantages including effective control of acid diffusion, improved resolution, and minimized LER.

In a preferred embodiment, the resist composition further comprises (D) a polymer comprising recurring units having the general formula (3), and fluorine-containing recurring units of at least one type selected from recurring units having the general formulae (4), (5), (6) and (7).

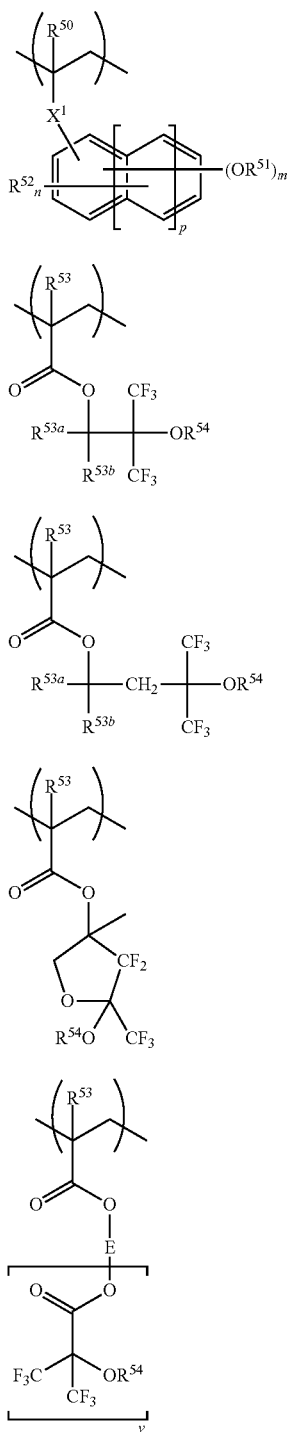

(3)

(4)

(5)

(6)

(7)

Herein $R^{50}$ is hydrogen or methyl, $R^{51}$ is hydrogen or a straight or branched $C_1$-$C_5$ monovalent hydrocarbon group which may be substituted with or separated by a heteroatom, $R^{52}$ is a straight or branched $C_1$-$C_5$ monovalent hydrocarbon group which may be substituted with or separated by a heteroatom, $R^{53}$ is each independently hydrogen, fluorine, methyl or trifluoromethyl, $R^{53a}$ and $R^{53b}$ are each independently hydrogen or a straight, branched or cyclic $C_1$-$C_{10}$ alkyl group, $R^{54}$ is each independently hydrogen, an acid labile group or a straight, branched or cyclic $C_1$-$C_{15}$ mon- ovalent hydrocarbon or fluorinated hydrocarbon group in which an ether bond (—O—) or carbonyl moiety (—C (=O)—) may intervene in a carbon-carbon bond, m is an integer of 1 to 3, n is an integer in the range: 0≤n≤5+2k−m, p is 0 or 1, v is an integer of 1 to 3, $X^1$ is a single bond, —C(=O)O— or —C(=O)NH—, and E is a straight, branched or cyclic $C_1$-$C_{20}$ (v+1)-valent hydrocarbon or fluorinated hydrocarbon group.

Preferably, the resist composition further comprises an acid generator capable of generating sulfonic acid upon receipt of high-energy radiation. Then the resist composition is effective as a chemically amplified positive tone resist composition.

Also preferably, the resist composition further comprises a basic compound. The resist composition thus constructed has greater advantages including effective control of acid diffusion, improved resolution, and minimized LER.

In another aspect, the invention provides a pattern forming process comprising the steps of applying the resist composition defined above onto a processable substrate to form a resist film, exposing patternwise the resist film to high-energy radiation, and developing the exposed resist film in an alkaline developer to form a resist pattern.

With the pattern forming process thus constructed, since the onium salt in the resist composition acts so as to effectively control acid diffusion in the exposure step, a resist film having improved resolution can be processed into a pattern with minimal LER.

Typically, the high-energy radiation is EUV or EB. Then a finer size pattern can be formed in the resist film.

Preferably, the processable substrate has the outermost surface of a chromium-containing material. Typically, the processable substrate is a photomask blank. The pattern forming process thus constructed ensures that even when a processable substrate (typically photomask blank) whose outermost surface is made of a chromium-containing or similar material to which the resist pattern profile is sensitive is used, a resist film is tenaciously bonded to the substrate and a pattern with minimal LER is formed therefrom via exposure and development.

Advantageous Effects of Invention

The chemically amplified positive resist composition of the invention is effective for controlling acid diffusion during the exposure step, exhibits a very high resolution during pattern formation, and forms a pattern with minimal LER. The pattern forming process using the resist composition can form a resist pattern with minimal LER while maintaining a high resolution. The invention is best suited for a micropatterning process, typically EUV or EB lithography.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group.

The abbreviations and acronyms have the following meaning.

EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LER: line edge roughness It is understood that for some structures represented by chemical formulae, there can exist enantiomers and diastereomers because of the presence of asymmetric carbon atoms. In such a case, a single formula collectively represents all such isomers. The isomers may be used alone or in admixture.

The inventors have found that when a sulfonium salt of nitrogen-containing carboxylic acid is added to a resist composition, a pattern with minimal LER can be formed.

Briefly stated, one embodiment of the invention is a chemically amplified positive tone resist composition for high-energy radiation lithography, comprising (A) an onium salt compound having the general formula (1) or (2) and (B) a resin (referred to as "base resin," hereinafter) adapted to be decomposed under the action of acid to increase its solubility in alkaline developer.

The onium salt compound has the general formula (1) or (2).

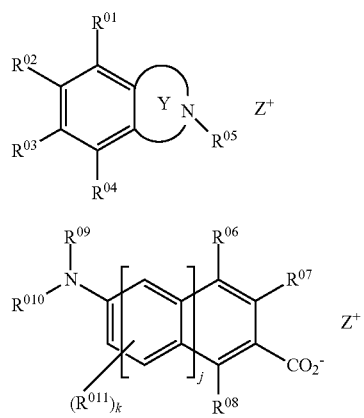

Herein $R^{01}$, $R^{02}$, $R^{03}$ and $R^{04}$ are each independently hydrogen, -L-$CO_2^-$, or a straight $C_1$-$C_{20}$, branched or cyclic $C_3$-$C_{20}$ monovalent hydrocarbon group which may be substituted with or separated by a heteroatom, or a pair of $R^{01}$ and $R^{02}$, $R^{02}$ and $R^{03}$, or $R^{03}$ and $R^{04}$ may bond together to form a ring with the carbon atoms to which they are attached. L is a single bond or a straight $C_1$-$C_{20}$, branched or cyclic $C_3$-$C_{20}$, divalent hydrocarbon group which may be substituted with or separated by a heteroatom. $R^{05}$ is hydrogen or a straight $C_1$-$C_{20}$, branched or cyclic $C_3$-$C_{20}$ monovalent hydrocarbon group which may be substituted with or separated by a heteroatom. $R^{06}$, $R^{07}$, $R^{08}$, $R^{09}$, $R^{010}$ and $R^{011}$ are each independently hydrogen or a straight $C_1$-$C_{20}$, branched or cyclic $C_3$-$C_{20}$ monovalent hydrocarbon group which may be substituted with or separated by a heteroatom, or a pair of $R^{06}$ and $R^{07}$ may bond together to form a ring with the carbon atoms to which they are attached, a pair of $R^{08}$ and $R^{011}$ may bond together to form a ring with the carbon atoms to which they are attached and any intervening carbon atoms, a pair of $R^{09}$ and $R^{010}$ may bond together to form a ring with the nitrogen atom. The subscript j is 0 or 1, and k is a number in the range: $0 \leq k \leq 1$ when j=0, or $0 \leq k \leq 3$ when j=1. $Z^+$ is a sulfonium cation of the general formula (a) or an iodonium cation of the general formula (b).

Herein $R^{100}$, $R^{200}$, and $R^{300}$ are each independently a straight $C_1$-$C_{20}$, branched or cyclic $C_3$-$C_{20}$ monovalent hydrocarbon group which may be substituted with or separated by a heteroatom, or any two or more of $R^{100}$, $R^{200}$, and $R^{300}$ may bond together to form a ring with the sulfur atom. $R^{400}$ and $R^{500}$ are each independently a straight $C_1$-$C_{20}$, branched or cyclic $C_3$-$C_{20}$ monovalent hydrocarbon group which may be substituted with or separated by a heteroatom. The partial structure represented by the formula:

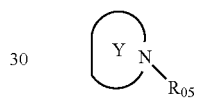

is a cyclic structure having the intervening nitrogen atom in which a hydrogen atom bonded to a cyclic structure-forming carbon atom may be replaced by a straight $C_1$-$C_{20}$, branched or cyclic $C_3$-$C_{20}$ monovalent hydrocarbon group or -L-$CO_2^-$, or in which a cyclic structure-forming carbon atom may be replaced by sulfur, oxygen or nitrogen. It is noted that one substituent: -L-$CO_2^-$ is essentially included in formula (1).

In formula (1), examples of the straight $C_1$-$C_{20}$, branched or cyclic $C_3$-$C_{20}$ monovalent hydrocarbon group represented by $R^{01}$ to $R^{05}$ include methyl, ethyl, propyl, isopropyl, n-butyl, sec-butyl, t-butyl, n-pentyl, t-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, adamantylmethyl, phenyl, naphthyl, and anthracenyl. In these hydrocarbon groups, a hydrogen atom (or atoms) may be replaced by a heteroatom such as oxygen, sulfur, nitrogen or halogen, or a carbon atom (or atoms) may be replaced by a heteroatom such as oxygen, sulfur or nitrogen. As a result, a hydroxyl group, cyano group, carbonyl group, ether bond, thioether bond, ester bond, sulfonic acid ester bond, carbonate bond, carbamate bond, lactone ring, sultone ring, carboxylic anhydride or haloalkyl group may form or intervene.

In formula (1), the partial structure represented by the formula:

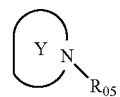

designates a cyclic structure having the intervening nitrogen atom in which at least one hydrogen atom bonded to a cyclic structure-forming carbon atom may be replaced by a straight $C_1$-$C_{20}$, branched or cyclic $C_3$-$C_{20}$ monovalent hydrocarbon group or -L-$CO_2^-$, or in which at least one cyclic structure-forming carbon atom may be replaced by sulfur, oxygen or nitrogen. Examples of the straight $C_1$-$C_{20}$, branched or cyclic $C_3$-$C_{20}$ monovalent hydrocarbon group are as exemplified above for $R^{01}$ to $R^{05}$.

The anion structure in formula (1) is characterized by the essential inclusion of one substituent: -L-$CO_2^-$. That is, the compound of formula (1) is a carboxylic acid onium salt.

In formula (1), examples of the straight $C_1$-$C_{20}$, branched or cyclic $C_3$-$C_{20}$ divalent hydrocarbon group (which may be substituted with or separated by a heteroatom) represented by L include straight alkane-diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; saturated cyclic hydrocarbon groups such as cyclopentanediyl, cyclohexanediyl, norbornanediyl, and adamantanediyl; and unsaturated cyclic hydrocarbon groups such as phenylene and naphthylene. In these hydrocarbon groups, a hydrogen atom (or atoms) may be replaced by an alkyl such as methyl, ethyl, propyl, n-butyl or t-butyl. Also in these hydrocarbon groups, a hydrogen atom (or atoms) may be replaced by a heteroatom such as oxygen, sulfur, nitrogen or halogen to form a hydroxyl group, cyano group, carbonyl group, ether bond, thioether bond, ester bond, sulfonic acid ester bond, carbonate bond, lactone ring, sultone ring, carboxylic anhydride or haloalkyl group.

Examples of the anion structure in the onium salt compound having formula (1) are shown below, but not limited thereto.

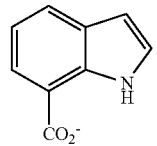
(1)-1

(1)-2

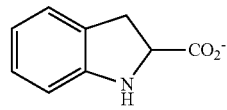
(1)-3

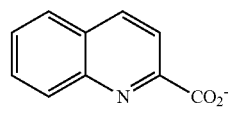
(1)-4

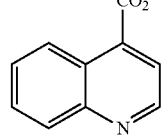
(1)-5

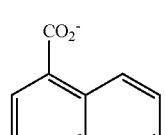
(1)-6

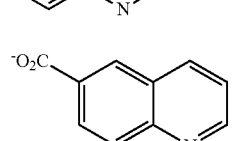
(1)-7

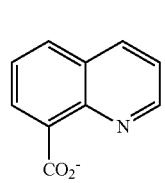
(1)-8

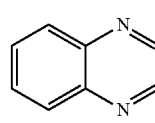
(1)-9

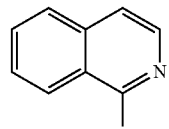
(1)-10

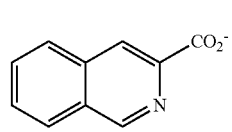
(1)-11

(1)-12

(1)-13

(1)-14

(1)-15

(1)-16

-continued
(1)-17
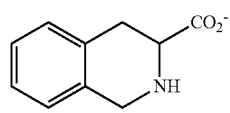
(1)-18
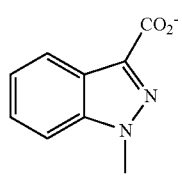
(1)-19
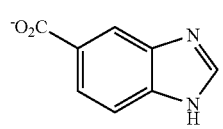
(1)-20
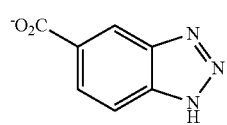
(1)-21
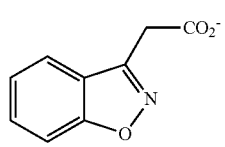
(1)-22
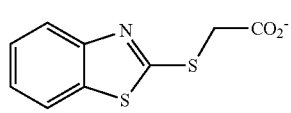
(1)-23
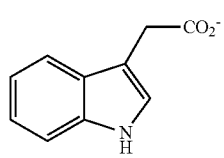
(1)-24
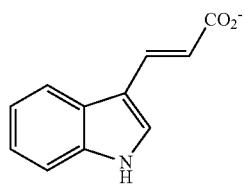
(1)-25
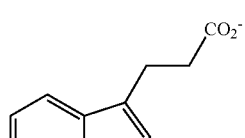
(1)-26
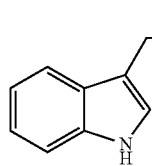
-continued
(1)-27
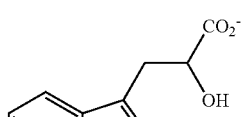
(1)-28
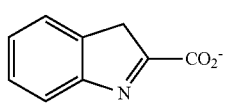
(1)-29
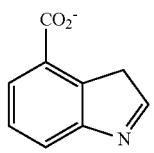
(1)-30
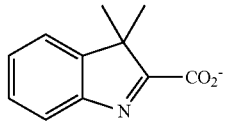
(1)-31
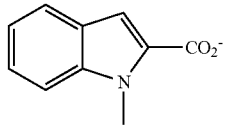
(1)-32
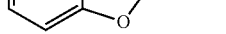
(1)-33
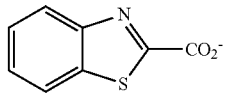
(1)-34
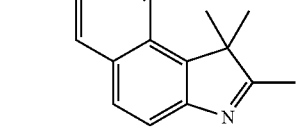
(1)-35
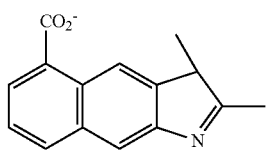
(1)-36
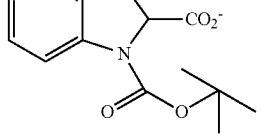
Of the anions having structural formulae (1)-1 to (1)-36, structures (1)-1 to (1)-28, (1)-31, and (1)-36 are especially preferred because of availability of starting carboxylic acids.
Of the illustrative anion structures, those compounds having protected nitrogen atom like (1)-36 have the advantage of ease of synthesis because of a lowering of water solubility, over the unprotected compounds. As the anion in the onium salt compound having formula (1), suitable structures having protected nitrogen atom are illustrated below, but not limited thereto.
(1)-37
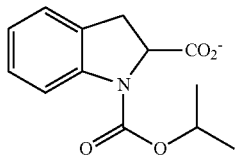
(1)-38
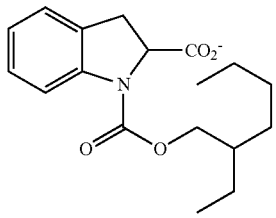
(1)-39
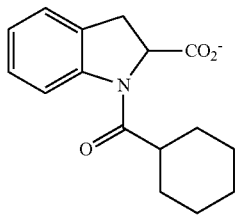
(1)-40
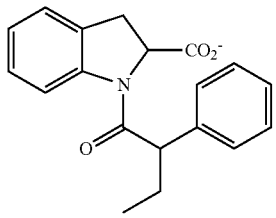
(1)-41
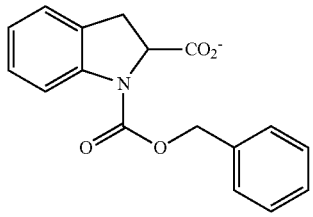
(1)-42
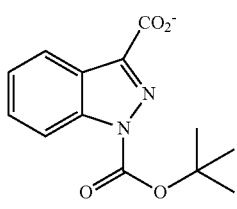
(1)-43
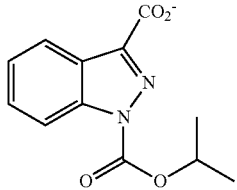
(1)-44
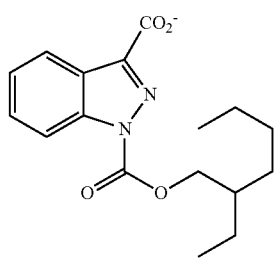
(1)-45
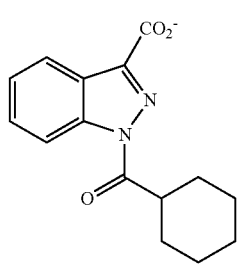
(1)-46
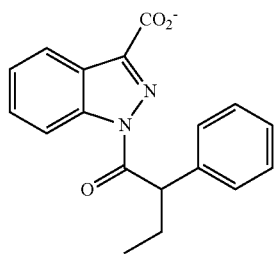
(1)-47
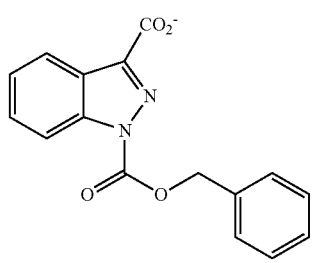
(1)-48
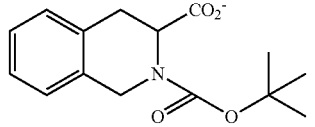
(1)-49
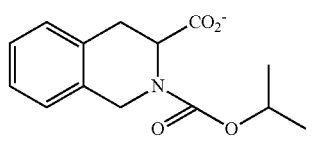
(1)-50
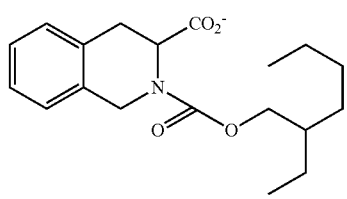

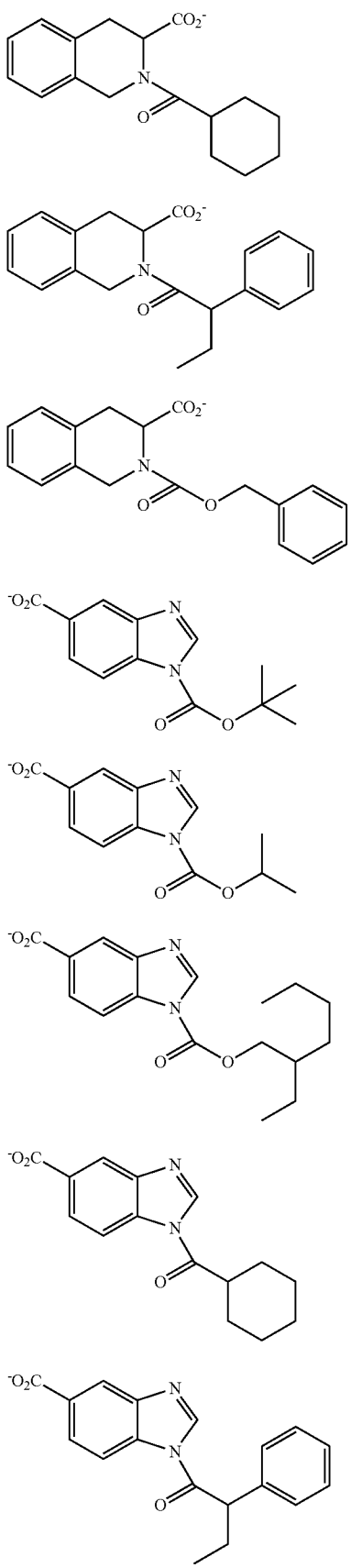
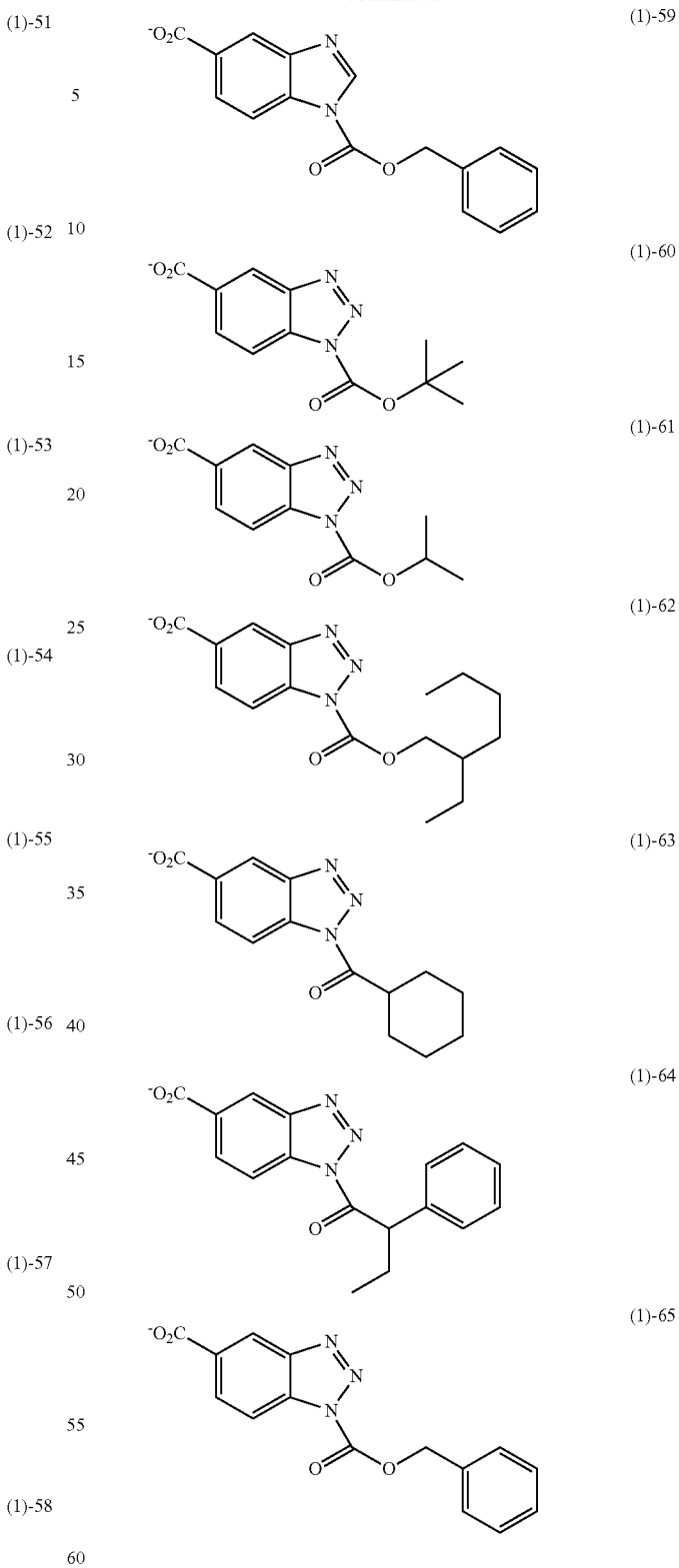

In formula (2), examples of the straight $C_1$-$C_{20}$, branched or cyclic $C_3$-$C_{20}$ monovalent hydrocarbon group represented by $R^{O6}$ to $R^{O11}$ include methyl, ethyl, propyl, isopropyl, n-butyl, sec-butyl, t-butyl, n-pentyl, t-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, adamantylmethyl, phenyl, naphthyl, and anthracenyl. In these hydrocarbon groups, a hydrogen atom (or atoms) may be replaced by a heteroatom such as oxygen, sulfur, nitrogen or halogen, or a carbon atom (or atoms) may be replaced by a heteroatom such as oxygen, sulfur or nitrogen. As a result, a hydroxyl group, cyano group, carbonyl group, ether bond, thioether bond, ester bond, sulfonic acid ester bond, carbonate bond, carbamate bond, lactone ring, sultone ring, carboxylic anhydride or haloalkyl group may form or intervene.

It is noted that when a pair of $R^{06}$ and $R^{07}$ bond together to form a ring with the carbon atoms to which they are attached, or a pair of $R^{08}$ and $R^{011}$ bond together to form a ring with the carbon atoms to which they are attached and any intervening carbon atoms, the ring may be either alicyclic or aromatic.

In conjunction with the partial structure represented by the formula:

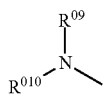

in formula (2) wherein $R^{09}$ and $R^{010}$ bond together to form a ring with the nitrogen atom, suitable ring structures are exemplified below.

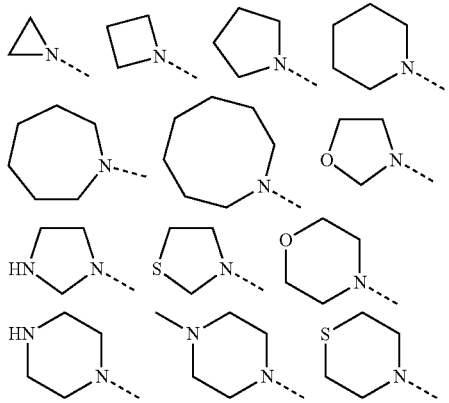

Herein, the broken line designates a valence bond to the aromatic ring in formula (2).

Examples of the anion structure in the onium salt compound having formula (2) are shown below, but not limited thereto.

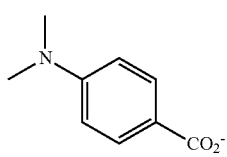

(2)-1

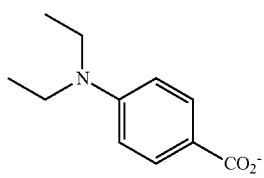

(2)-2

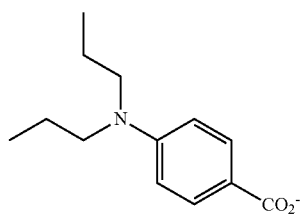

(2)-3

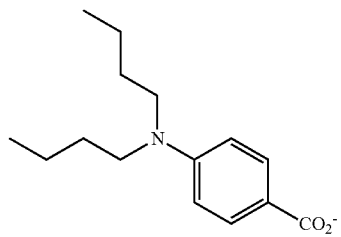

(2)-4

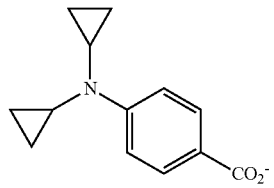

(2)-5

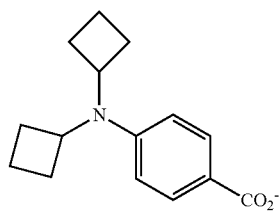

(2)-6

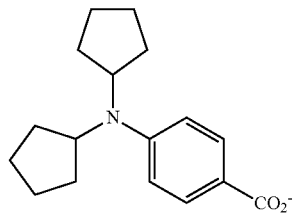

(2)-7

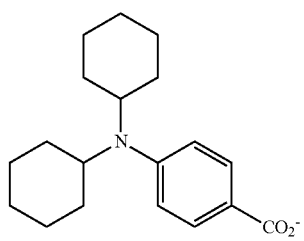

(2)-8

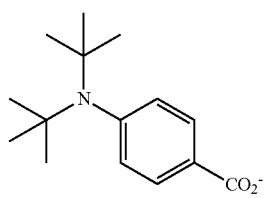

(2)-9

-continued
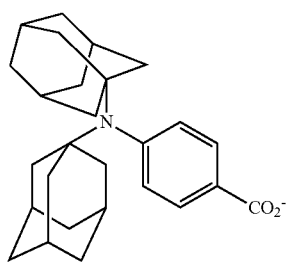
(2)-10
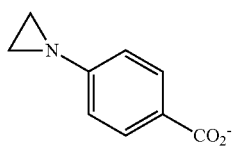
(2)-11
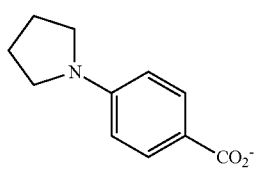
(2)-12
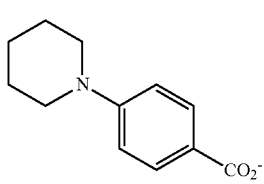
(2)-13
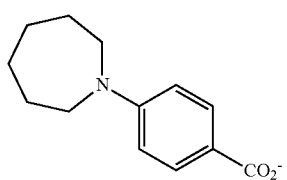
(2)-14
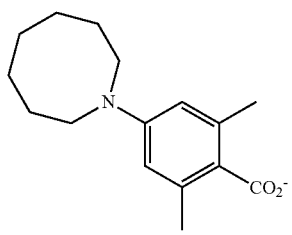
(2)-15
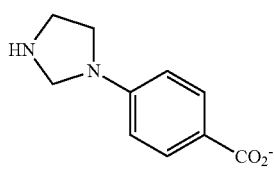
(2)-16
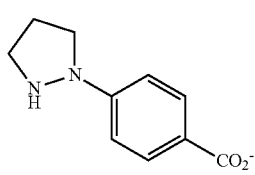
(2)-17
-continued
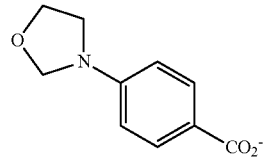
(2)-18
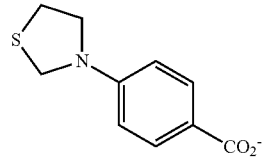
(2)-19
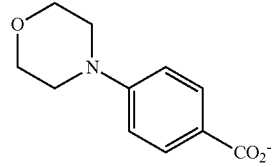
(2)-20
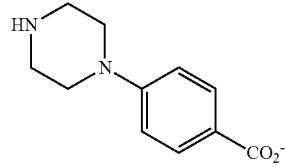
(2)-21
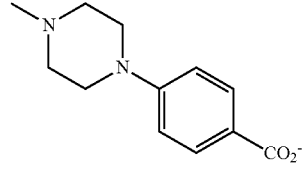
(2)-22
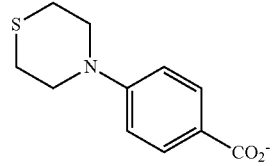
(2)-23
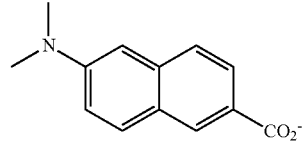
(2)-24
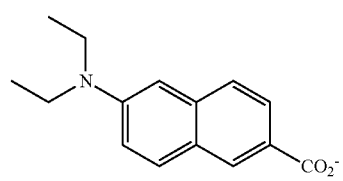
(2)-25

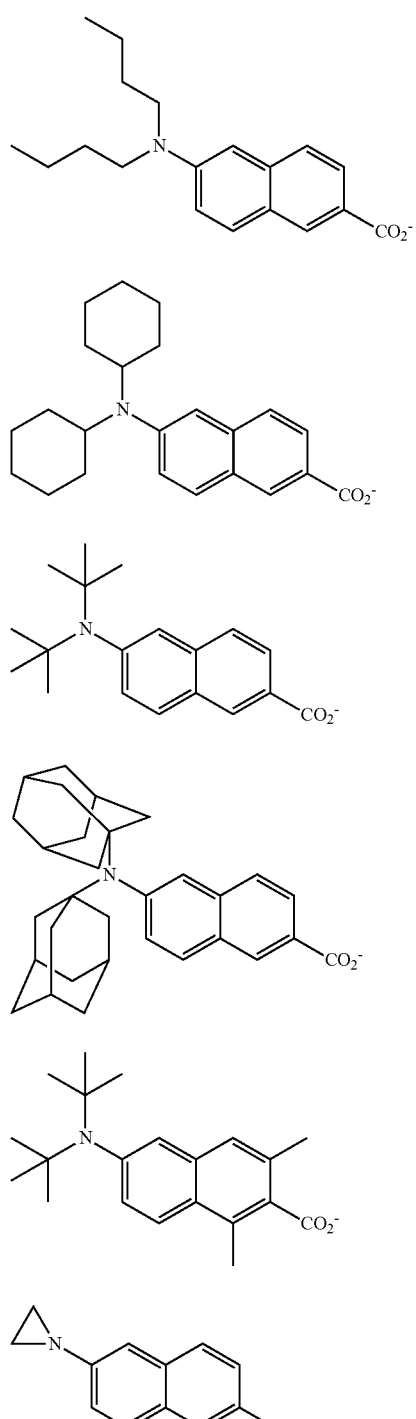
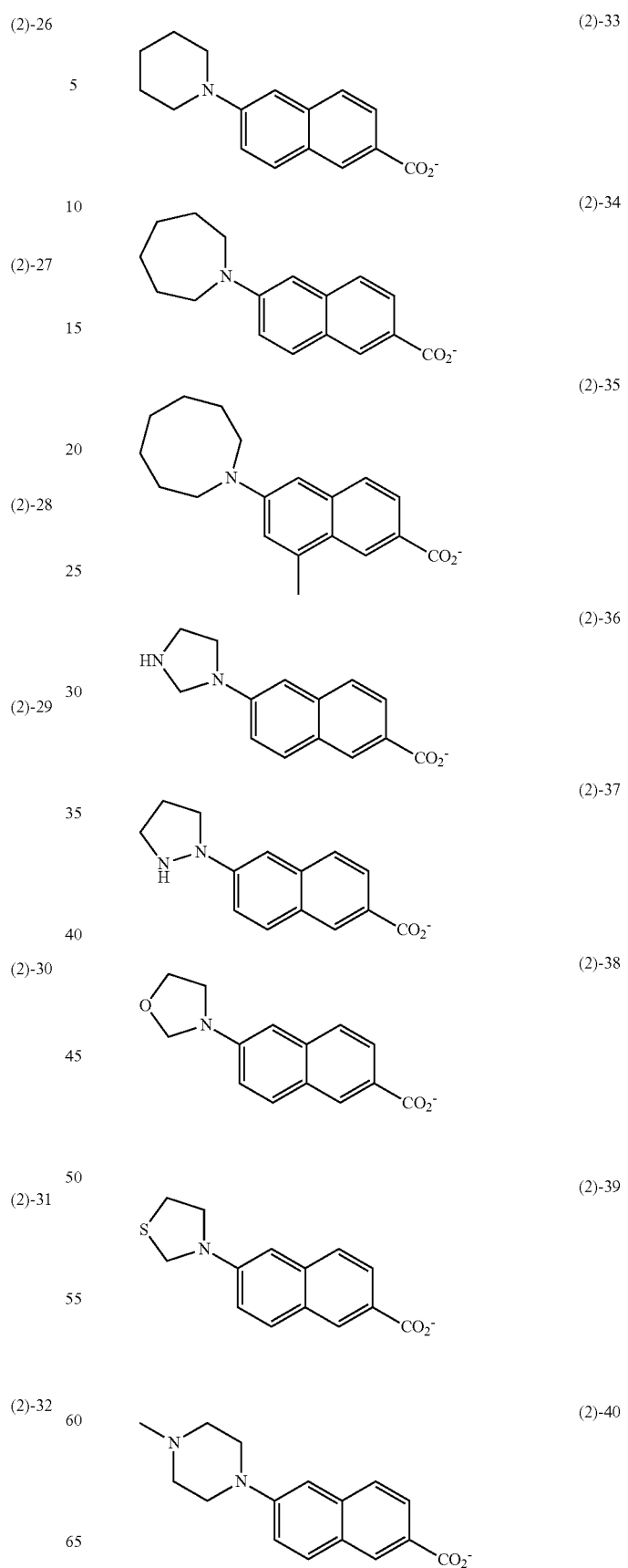

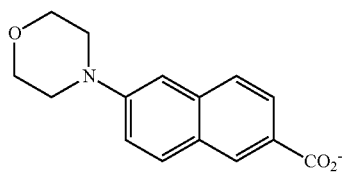

(2)-41

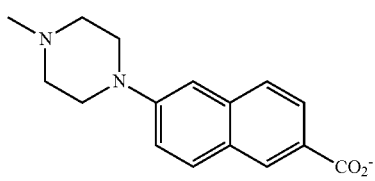

(2)-42

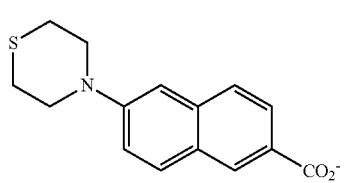

(2)-43

Of the anions having structural formulae (2)-1 to (2)-43, structures (2)-1 to (2)-23 are especially preferred because of availability of starting carboxylic acids and ease of synthesis.

In formula (a), $R^{100}$, $R^{200}$, and $R^{300}$ are each independently a straight $C_1$-$C_{20}$, branched or cyclic $C_3$-$C_{20}$ monovalent hydrocarbon group (which may be substituted with or separated by a heteroatom), examples of which are as exemplified for $R^{01}$ to $R^{05}$ in formula (1). When any two or more of $R^{100}$, $R^{200}$, and $R^{300}$ bond together to form a ring with the sulfur atom, suitable rings are exemplified by the following structures.

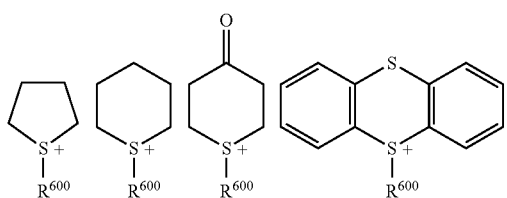

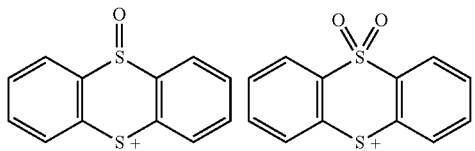

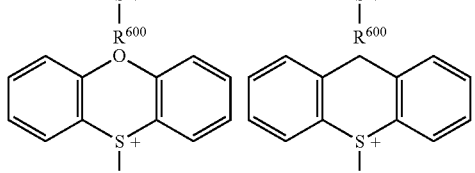

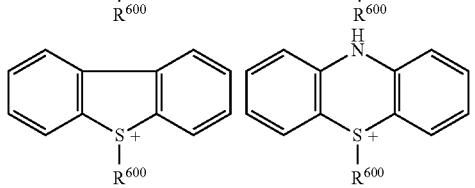

Herein, $R^{600}$ is a monovalent hydrocarbon group as defined and exemplified for $R^{100}$, $R^{200}$, and $R^{300}$.

Preferred examples of the sulfonium cation having formula (a) are shown below, but not limited thereto.

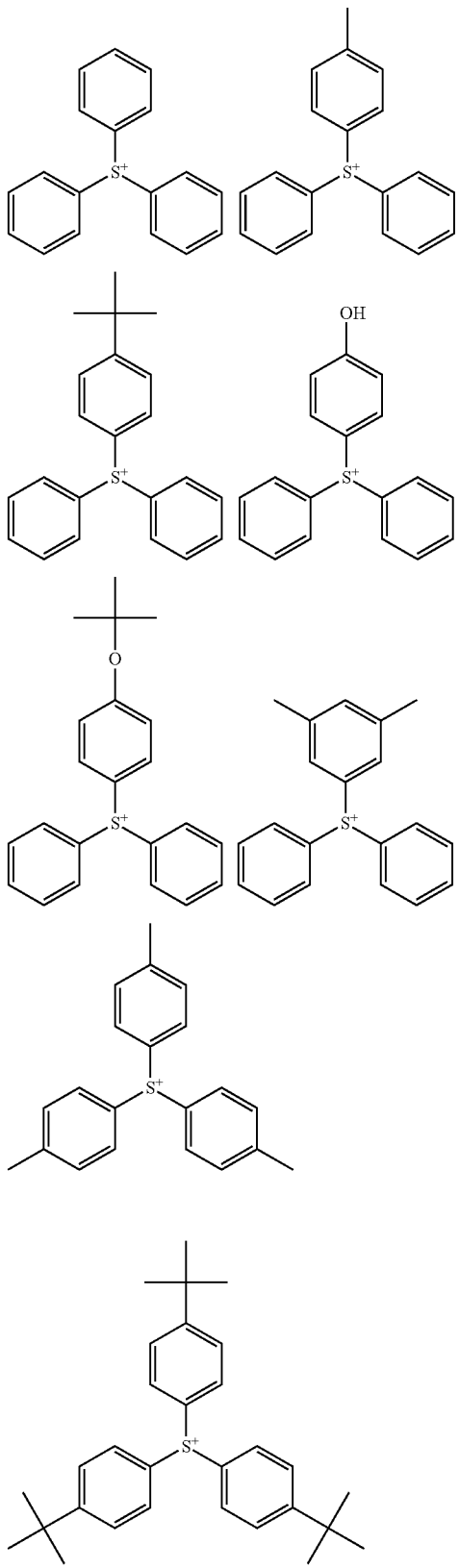

-continued

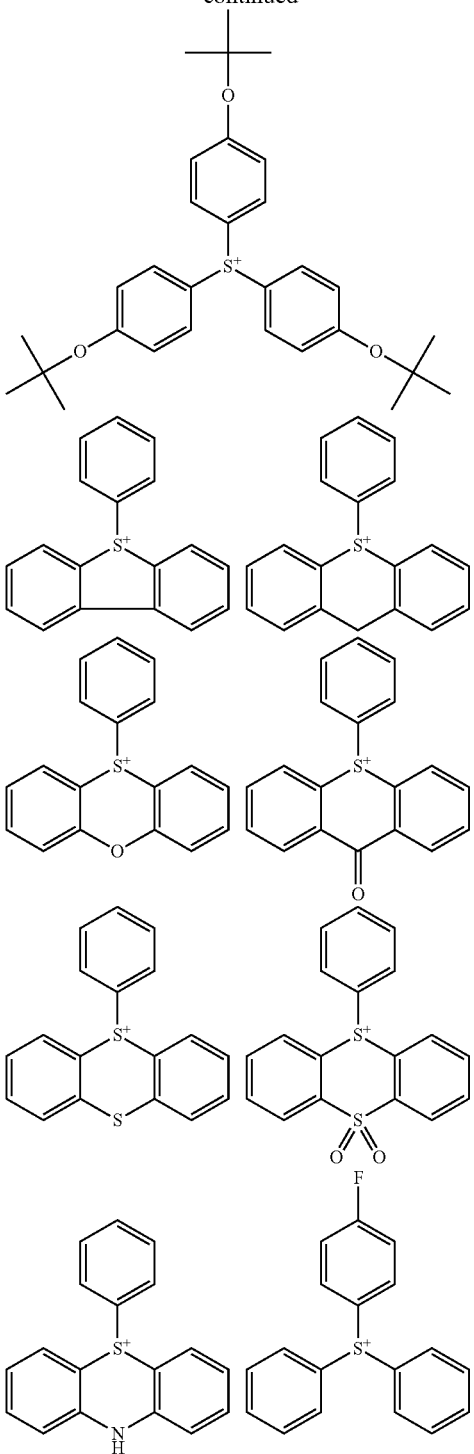

In formula (b), $R^{400}$ and $R^{500}$ are each independently a straight $C_1$-$C_{20}$, branched or cyclic $C_3$-$C_{20}$ monovalent hydrocarbon group (which may be substituted with or separated by a heteroatom), examples of which are as exemplified for $R^{O1}$ to $R^{O5}$ in formula (1), with aryl groups being preferred.

Preferred examples of the iodonium cation having formula (b) include bis(4-methylphenyl)iodonium, bis(4-ethylphenyl)iodonium, bis(4-t-butylphenyl)iodonium, bis(4-(1,1-dimethylpropyl)phenyl)iodonium, 4-methoxyphenylphenyliodonium, 4-t-butoxyphenylphenyliodonium, 4-acryloyloxyphenylphenyliodonium, and 4-methaoryloyloxyphenylphenyliodonium. Inter alia, bis(4-t-butylphenyl)iodonium is more preferred.

Exemplary structures for the carboxylic acid sulfonium or iodonium salt include arbitrary combinations of anions with cations, both as exemplified above.

The carboxylic acid onium salt having formula (1) or (2) functions as an acid diffusion regulator. This function may be accounted for by the following mechanism. Since the acid generated from a PAG in a resist composition must have a strong acidity enough to deprotect the acid labile group on the base resin, a sulfonic acid fluorinated at α-position, imidic acid or methide acid is used in ArF lithography, for example. It is now assumed that the acid diffusion regulator of the invention is co-present with a PAG in a resist composition. The acid generated from the PAG undergoes ion exchange with the acid diffusion regulator and is converted back to a sulfonium or iodonium salt, and instead, the anion moiety of the acid diffusion regulator is converted to and released as carboxylic acid. Differently stated, via ion exchange, the strong acid is neutralized with the inventive carboxylic acid onium salt. That is, the inventive carboxylic acid onium salt functions as an acid diffusion regulator. Another mechanism is also contemplated that the cation of the inventive carboxylic acid onium salt is photo-decomposed to generate carboxylic acid. However, the acid generated thereby is a weak acid, not having an acidity enough to deprotect the acid labile group on the base resin.

In general, the acid diffusion regulator, which may be regarded as onium salt type quencher, tends to form a resist pattern with a lower LER than the amine compound quencher. It accounts for this tendency that salt exchange between strong acid and carboxylic acid onium salt is repeated infinitely. The site where strong acid is generated at the end of exposure is different from the initial site where the strong acid-generating onium salt is present. Since the cycle of acid generation (by high-energy irradiation) and salt exchange is repeated over and over, the acid generation points are averaged, which leads to a resist pattern with reduced LER after development.

As a matter of course, the acid diffusion regulator of the invention is also present in the unexposed region. It is believed that the acid diffusion regulator can trap the acid which has diffused from the exposed region, via the ion exchange reaction mentioned above. It is also believed that since the acid diffusion regulator has a nitrogen atom in its anion moiety, the nitrogen directly traps the acid. Both the mechanisms ensure to quench the acid which has diffused into the unexposed region. As a result, the contrast between the exposed and unexposed regions is increased, leading to substantial improvements in resolution and roughness.

With respect to the compound which exerts a quencher effect by the same mechanism, Patent Document 8 (JP 4226803) and JP-A H11-327143 describe the use of carboxylic acid onium salts, alkylsulfonic acid onium salts, and arylsulfonic acid onium salts as the acid diffusion regulator. However, when the alkylsulfonic acid onium salt or arylsulfonic acid onium salt is used, the acid generated therefrom has a certain level of acid strength so that in the over-exposed region, part of the salt induces deprotection reaction rather than serving as the quencher. As a result, acid diffusion is promoted, degrading resist performance such as resolution or roughness. When an alkanecarboxylic acid onium salt is used, the carboxylic acid generated therefrom has too weak an acidity to react with the acid labile group on the base resin. However, the salt fails to trap exhaustively the strong acid generated by a PAG that has diffused into the unexposed region, leading to resolution and roughness below the satisfactory level. By contrast, since the acid diffusion regulator of the invention has a quench ability due to both ion exchange and neutralization via reaction with nitrogen atom, it can trap the acid that has diffused into the unexposed region more positively than the alkanecarboxylic acid onium salt.

Also, Patent Document 9 (JP-A 2006-208781) and Patent Document 10 (JP-A 2012-123189) disclose a photo-decomposable base in the form of a sulfonium salt having a nitrogen-containing group in its anion moiety, adapted to be decomposed to lose its basicity in the exposed region. A high contrast is available as a result of losing basicity in the exposed region, but maintaining basicity in the unexposed region. In fact, however, the control of acid diffusion is insufficient and resist performance such as resolution or roughness is not satisfactory. This is probably because the sulfonic acid generated from the photo-decomposable base in the exposed region also contributes to deprotection reaction together with the PAG.

On the other hand, JP-A 2007-293250 discloses nitrogen-containing carboxylic acid sulfonium or iodonium salts although synthesis examples are described nowhere. These nitrogen-containing carboxylates of monocyclic structure generally have a high solubility in water and an extremely low solubility in organic solvents. They are thus less compatible in resist compositions. Such properties suggest a possibility that resist performance such as pattern profile or roughness is degraded because the resist film in the unexposed region is partially dissolved away in the positive tone resist process of alkaline development type, or the resist film in the unexposed region is partially left undissolved in the negative tone resist process of organic solvent development type.

By contrast, the inventive onium salt having formula (1) or (2) functioning as acid diffusion regulator is characterized in that the anion moiety is a nitrogen-containing carboxylate of fused ring structure. The inventive onium salt is lipophilic enough to eliminate any concern about performance degradation due to solubility as discussed above. Since the inventive onium salt has the acid trapping function by ion exchange process as previously mentioned, it is effective for improving LER. Since the inventive onium salt can trap the acid that has diffused into the unexposed region, due to both ion exchange reaction and neutralization reaction at the nitrogen-containing site, it is effective for improving contrast and controlling acid diffusion. On use of the onium salt having formula (1) or (2), the lithography performance in terms of resolution and roughness is improved as well. From the aspect of resolution improvement, the salt having formula (1) is especially preferred. The resist composition comprising the salt having formula (1) is quite suitable for micropatterning.

In the resist composition, the onium salt having formula (1) or (2) is preferably formulated in an amount of 0.1 to 50 parts by weight, more preferably 0.5 to 30 parts by weight per 100 parts by weight of the base resin. Outside the range, a less amount of the salt may not exert its function whereas a larger amount of the salt may invite degradations such as a lowering of sensitivity, a lack of solubility, and generation of foreign particles.

The compounds having formulae (1) and (2) may be readily synthesized by the skilled artisan using any well-known organic chemistry methods. For example, the desired compound may be synthesized by ion exchange reaction between a carboxylic acid serving as a precursor to the anion moiety in formula (1) and a cationic agent such as a triarylsulfonium halide or diaryliodonium halide. The carboxylic acid as the precursor may be synthesized by any well-known organic chemistry methods or any commercially available one may be used. The ion exchange reaction may be performed by any well-known methods, for example, with reference to JP-A 2007-145797.

In the positive resist composition of the invention, (D) a polymer comprising recurring units having the general formula (3), and fluorine-containing recurring units of at least one type selected from recurring units having the general formulae (4), (5), (6) and (7) may be added for the purpose of contrast improvement.

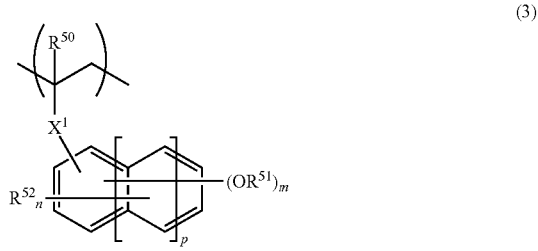

(3)

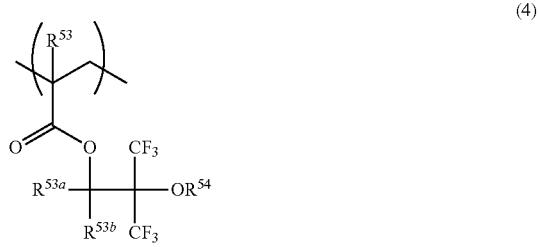

(4)

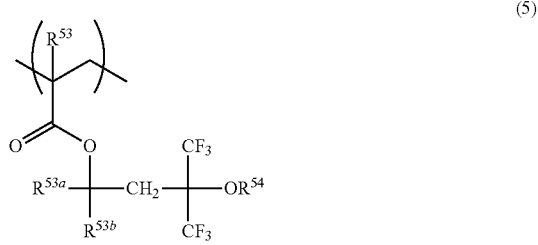

(5)

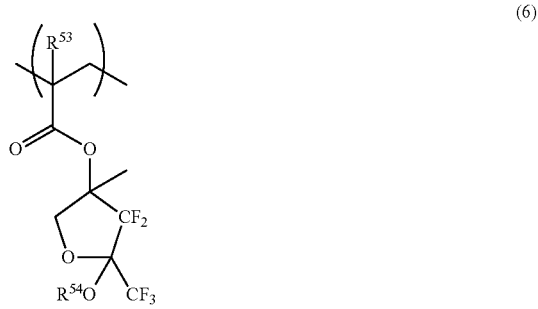

(6)

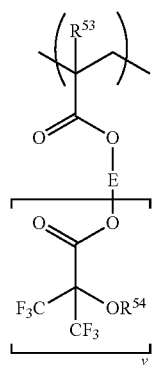

(7)

Herein $R^{50}$ is hydrogen or methyl, $R^{51}$ is hydrogen or a straight or branched $C_1$-$C_5$ monovalent hydrocarbon group which may be substituted with or separated by a heteroatom, $R^{52}$ is a straight or branched $C_1$-$C_5$ monovalent hydrocarbon group which may be substituted with or separated by a heteroatom, $R^{53}$ is each independently hydrogen, fluorine, methyl or trifluoromethyl, $R^{53a}$ and $R^{53b}$ are each independently hydrogen or a straight, branched or cyclic $C_1$-$C_{10}$, alkyl group, $R^{54}$ is each independently hydrogen, an acid labile group or a straight, branched or cyclic $C_1$-$C_{15}$ monovalent hydrocarbon or fluorinated hydrocarbon group in which an ether bond (—O—) or carbonyl moiety (—C(=O)—) may intervene in a carbon-carbon bond, m is an integer of 1 to 3, n is an integer in the range: $0 \le n \le 5 + 2k - m$, p is 0 or 1, v is an integer of 1 to 3, $X^1$ is a single bond, —C(=O)O— or —C(=O)NH—, and E is a straight, branched or cyclic $C_1$-$C_{20}$ (v+1)-valent hydrocarbon or fluorinated hydrocarbon group.

Exemplary of the monovalent hydrocarbon group are alkyl, alkenyl and alkynyl groups, with the alkyl groups being preferred. Suitable alkyl groups include methyl, ethyl, n-propyl, isopropyl, n-butyl, isobutyl, sec-butyl, and n-pentyl. A heteroatom such as oxygen, sulfur or nitrogen may intervene in a carbon-carbon bond of the monovalent hydrocarbon group.

In formula (3), the group: —$OR^{51}$ is preferably hydrophilic. In this case, $R^{51}$ is preferably hydrogen or a $C_1$-$C_5$ alkyl group whose carbon-carbon bond is separated by an oxygen atom.

Examples of the recurring unit having formula (3) are shown below, but not limited thereto.

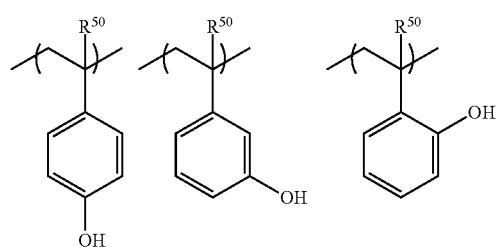

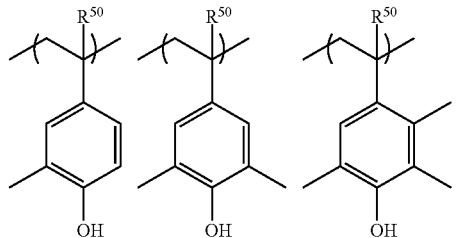

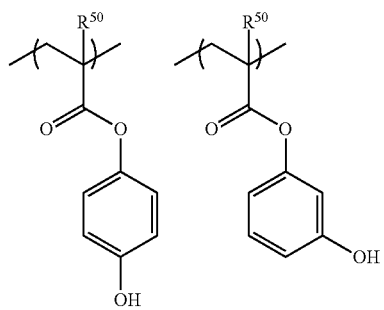

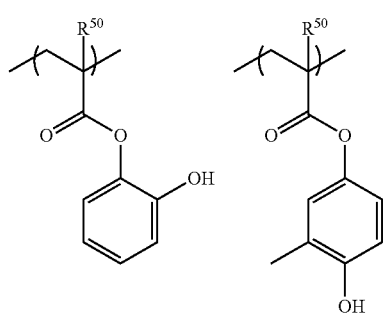

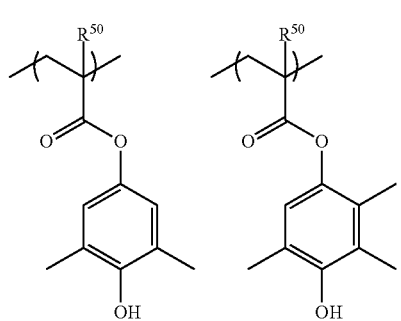

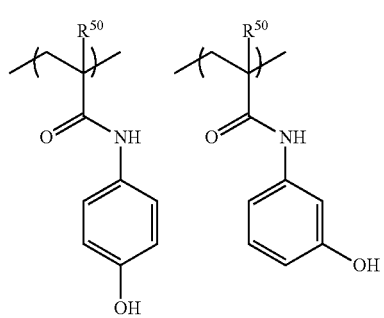

-continued

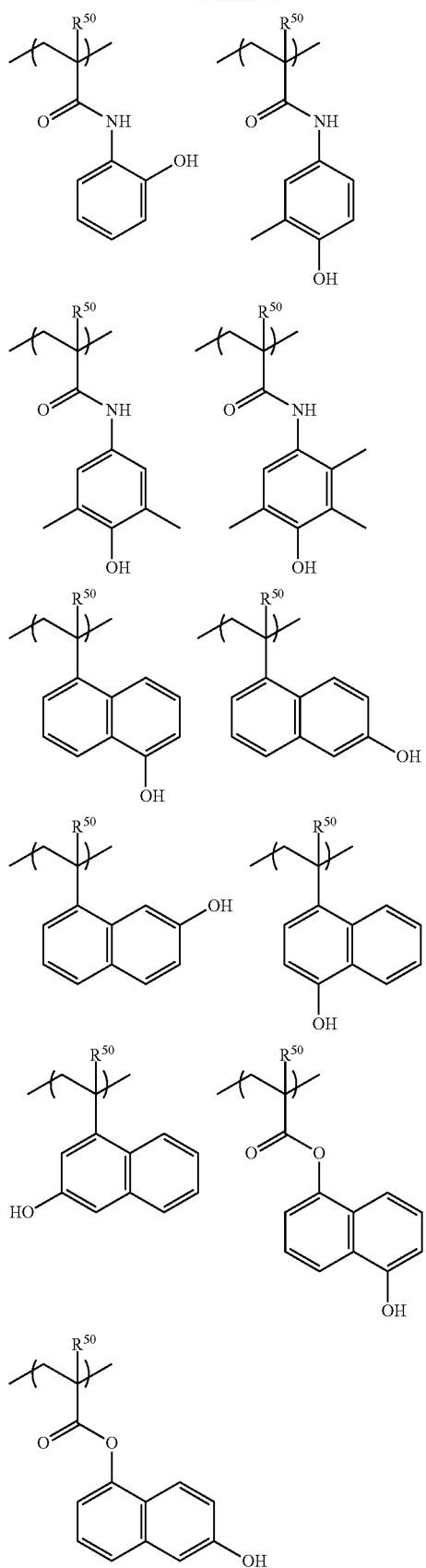
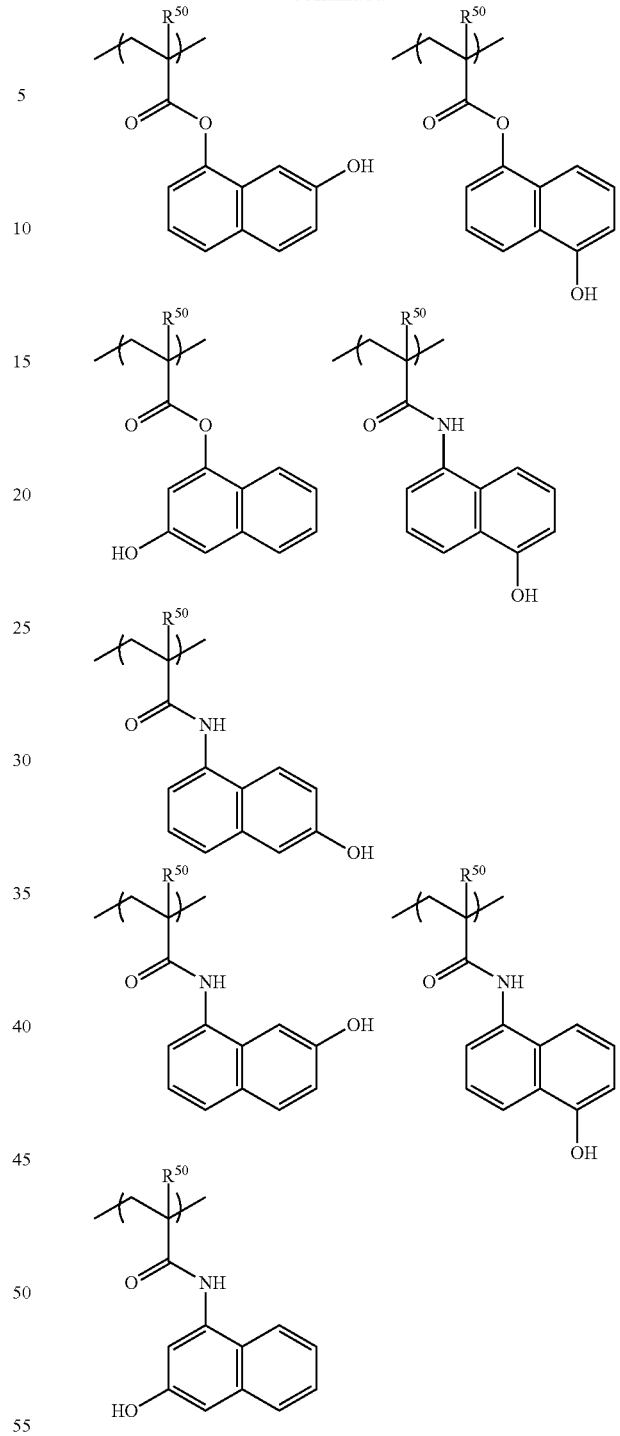

Notably $R^{50}$ is as defined above.

In the recurring unit having formula (3), $X^1$ is preferably —C(=O)O— or —C(=O)NH— rather than a single bond. Also preferably $R^{50}$ is hydrogen or methyl. Due to inclusion of a carbonyl moiety in $X^1$, an acid trapping ability is improved. When $R^{50}$ is methyl, a rigid polymer having a higher glass transition temperature (Tg) is available, which is effective for suppressing acid diffusion. The resulting resist film has age stability sufficient to avoid the degradation of resolution and pattern profile.

The recurring units containing at least one fluorine atom are units of at least one type selected from recurring units having formulae (4) to (7).

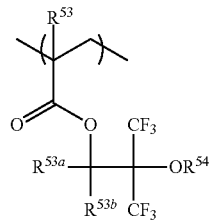
(4)

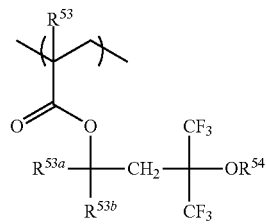
(5)

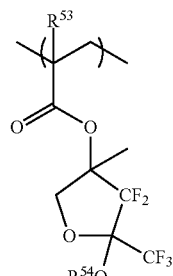
(6)

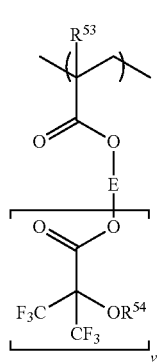
(7)

Herein $R^{53}$ is each independently hydrogen, fluorine, methyl or trifluoromethyl. $R^{53a}$ and $R^{53b}$ are each independently hydrogen or a straight, branched or cyclic $C_1$-$C_{10}$ alkyl group. $R^{54}$ is each independently hydrogen, a straight, branched or cyclic $C_1$-$C_{15}$ monovalent hydrocarbon group or monovalent fluorinated hydrocarbon group, or an acid labile group. When $R^{54}$ is a monovalent hydrocarbon group or monovalent fluorinated hydrocarbon group, an ether bond (—O—) or carbonyl moiety (—C(=O)—) may intervene in a carbon-carbon bond. E is a straight, branched or cyclic $C_1$-$C_{20}$ (v+1)-valent hydrocarbon or fluorinated hydrocarbon group, and v is an integer of 1 to 3.

Examples of the straight, branched or cyclic $C_1$-$C_{10}$ alkyl group include methyl, ethyl, n-propyl, isopropyl, cyclopropyl, n-butyl, isobutyl, sec-butyl, t-butyl, cyclobutyl, n-pentyl, cyclopentyl, n-hexyl, cyclohexyl, n-heptyl, n-octyl, n-nonyl, n-decyl, adamantyl, and norbornyl. Inter alia, the straight, branched or cyclic $C_1$-$C_6$ alkyl groups are preferred.

Exemplary of the straight, branched or cyclic $C_1$-$C_{15}$ monovalent hydrocarbon group are alkyl, alkenyl and alkynyl groups, with the alkyl groups being preferred. Suitable alkyl groups include n-undecyl, n-dodecyl, tridecyl, tetradecyl and pentadecyl as well as the aforementioned groups. Examples of the straight, branched or cyclic $C_1$-$C_{15}$ monovalent fluorinated hydrocarbon group include the foregoing examples of the monovalent hydrocarbon group in which one or more or even all carbon-bonded hydrogen atoms are substituted by fluorine atoms.

Examples of the straight, branched or cyclic $C_1$-$C_{20}$ (v+1)-valent hydrocarbon or fluorinated hydrocarbon group include the foregoing examples of the monovalent hydrocarbon or fluorinated hydrocarbon group, with the number (v) of hydrogen atoms being eliminated.

Examples of the recurring units having formulae (4) to (7) are shown below, but not limited thereto.

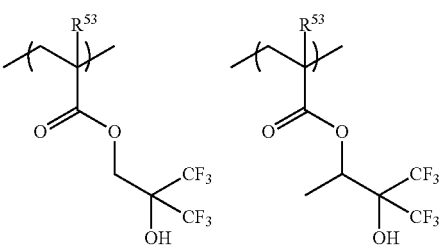

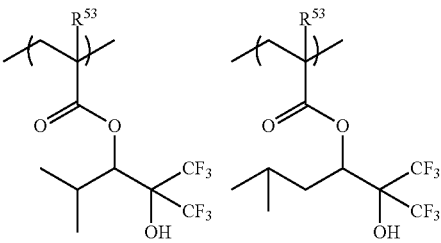

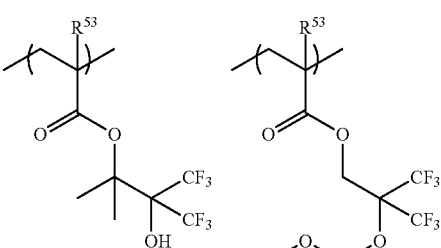

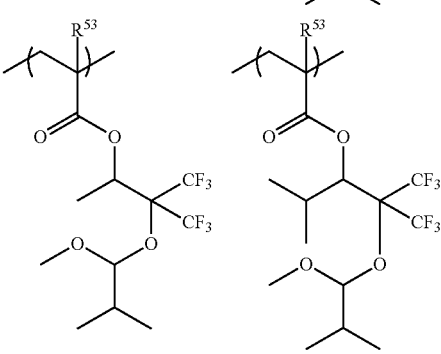

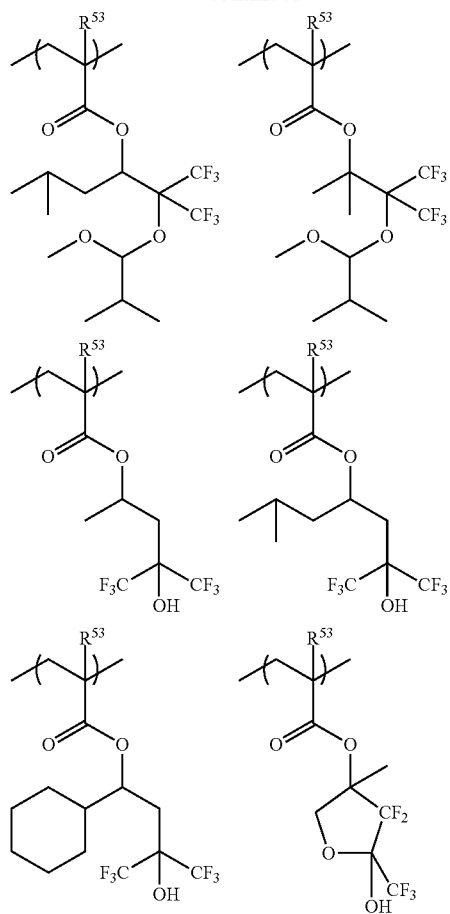
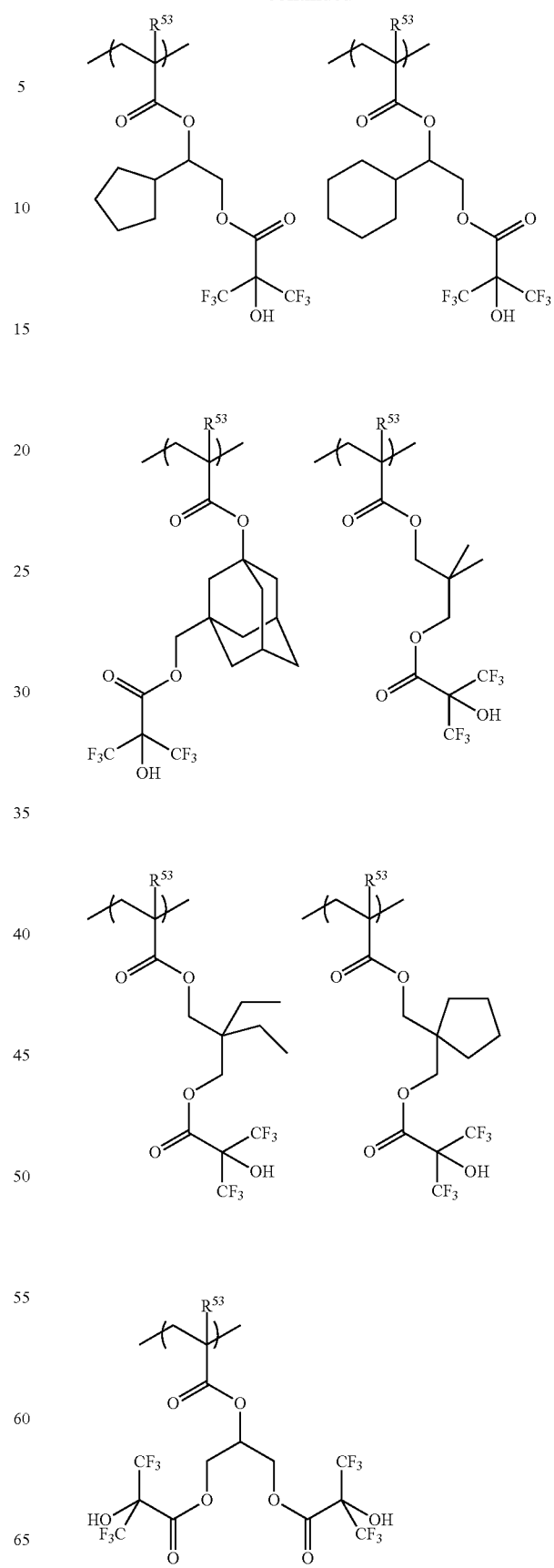

-continued

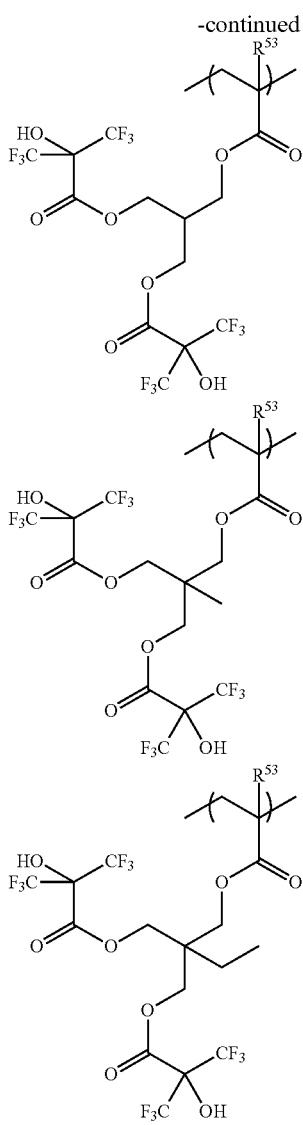

Herein $R^{53}$ is as defined above.

The recurring units having formulae (4) to (7) may be of one type or a mixture of two or more types. Preferably the recurring units having formulae (4) to (7) are incorporated in a range of 20 to 95 mol % based on the overall recurring units of the polymer (D).

In addition to the foregoing units, the polymer (D) may further comprise other units, for example, units described in JP-A 2014-177407, paragraphs [0046] to [0078]. When the polymer (D) comprises other recurring units, the other recurring units are preferably incorporated in a range of up to 50 mol % based on the overall recurring units.

The polymer (D) may be prepared by any well-known techniques, by selecting suitable monomers and effecting copolymerization while optionally combining protection and deprotection reactions. The copolymerization reaction is preferably radical or anionic polymerization though not limited thereto. Reference may be made to JP-A 2004-115630.

The polymer (D) preferably has a weight average molecular weight (Mw) of 2,000 to 50,000, and more preferably 3,000 to 20,000, as measured by GPC versus polystyrene standards. A polymer with a Mw of less than 2,000 may promote acid diffusion, degrade resolution or detract from age stability. A polymer with too high Mw is less soluble in the solvent and tends to cause coating defects. The polymer (D) should preferably have a dispersity (Mw/Mn) of 1.0 to 2.2, especially 1.0 to 1.7.

The polymer (D) is preferably blended in an amount of 0.01 to 30 parts by weight, more preferably 0.1 to 20 parts by weight per 100 parts by weight of the base resin (B).

The resist composition of the invention is also characterized by comprising (B) a base resin comprising recurring units of the general formula (U-1).

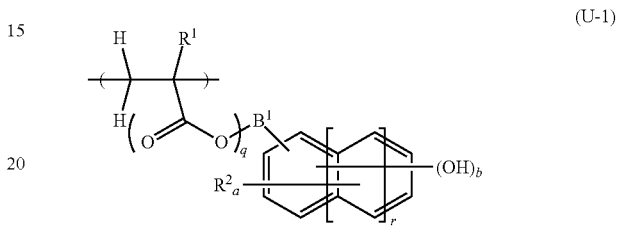

Herein q is 0 or 1, r is an integer of 0 to 2, $R^1$ is hydrogen, fluorine, methyl or trifluoromethyl, $R^2$ is each independently hydrogen or $C_1$-$C_6$ alkyl, $B^1$ is a single bond or $C_1$-$C_{10}$ alkylene which may contain an ether bond, "a" is an integer satisfying a≤5+2r−b, and b is an integer of 1 to 3.

Of the recurring units, the recurring unit free of the linker (—CO—O—$B^1$—), that is, of formula (U-1) wherein q=0 and $B^1$-single bond is a unit derived from a monomer having a 1-substituted or unsubstituted vinyl group bonded to a hydroxyl-substituted aromatic ring, typically a hydroxystyrene unit. For example, units derived from 3-hydroxystyrene, 4-hydroxystyrene, 5-hydroxy-2-vinylnaphthalene, and 6-hydroxy-2-vinylnaphthalene are preferred.

The recurring unit having the linker (—CO—O—$B^1$—) is a unit derived from a carbonyl-substituted vinyl monomer, typically (meth)acrylate. Examples of the recurring unit having the linker (—CO—O—$B^1$—), represented by formula (U-1), are shown below.

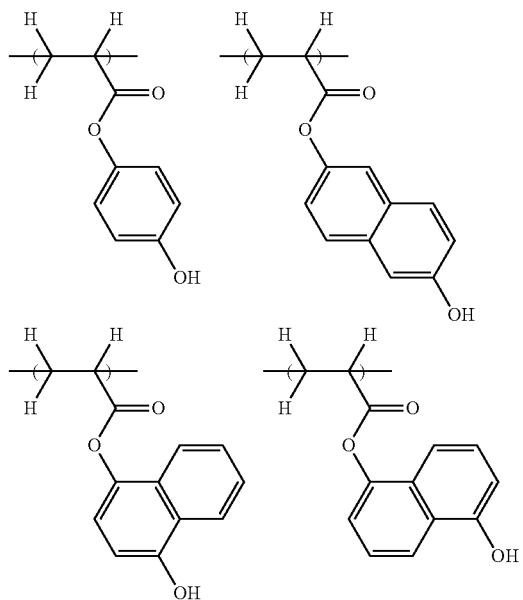

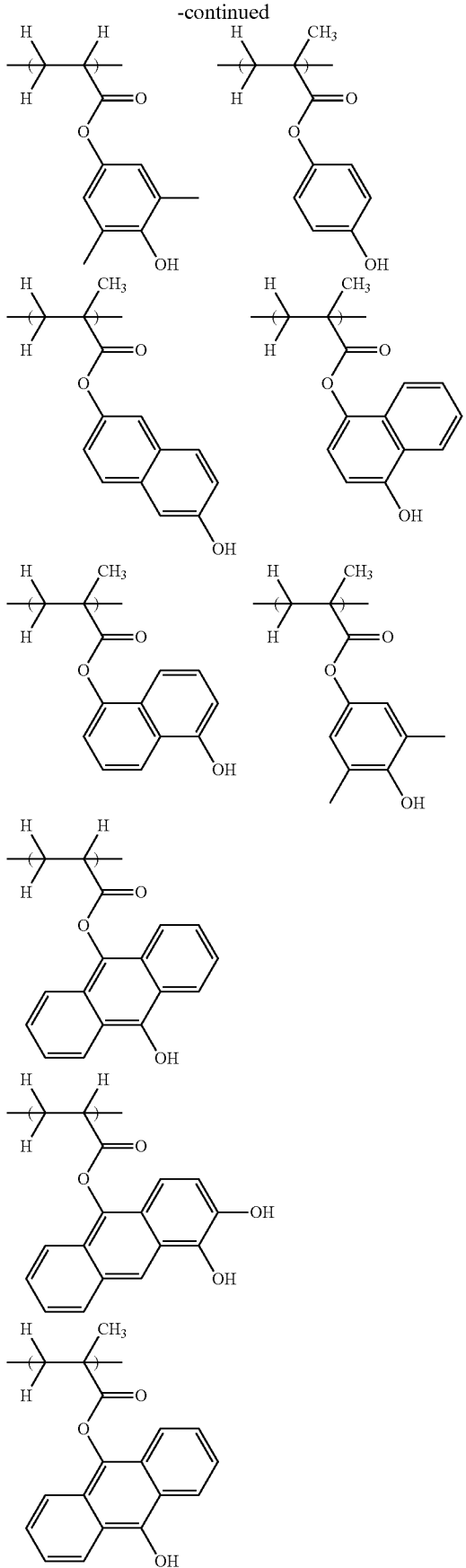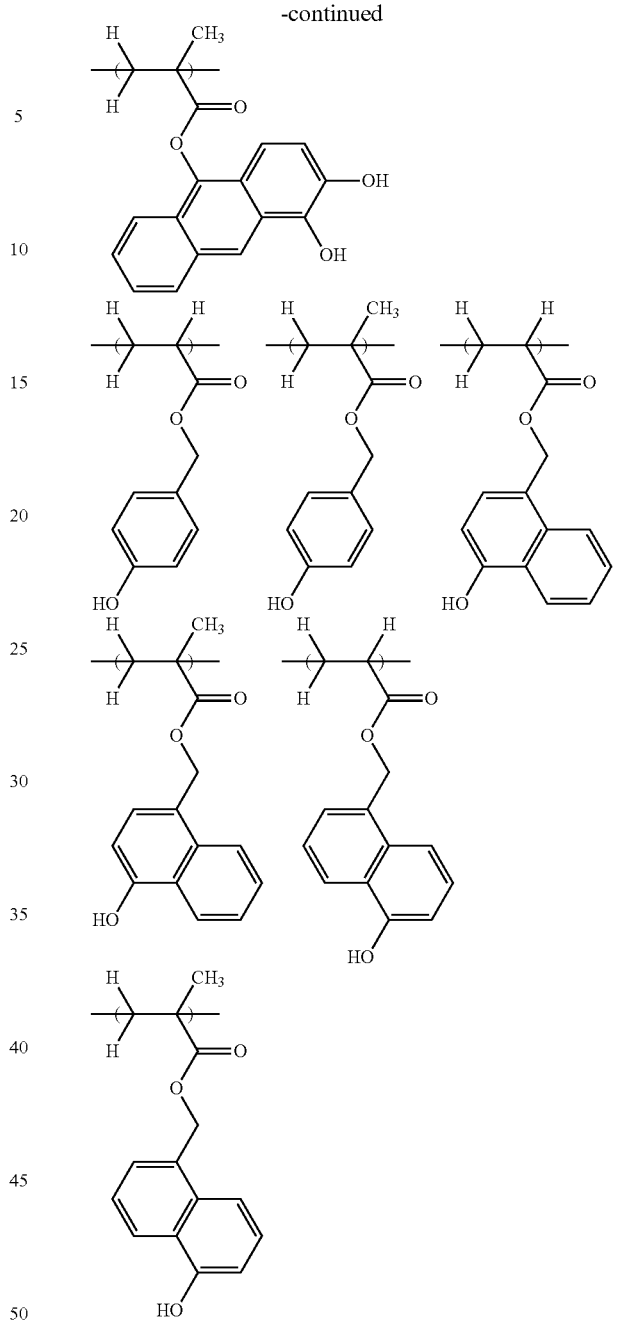

The units having formula (U-1) may be of one type or a mixture of two or more types. In the base resin, the units having formula (U-1) are preferably incorporated in a range of 40 to 90 mol % based on the overall recurring units. When recurring units of at least one type selected from formulae (U-3) and (U-4) for imparting better etch resistance to the resin are also incorporated in the base resin and these units have a phenolic hydroxyl group substituted thereon, a proportion of these units should be added to a proportion of the units having formula (U-1) so that the total may fall in the above-defined range.

In order that the resist composition serve as a positive resist composition wherein the exposed region of a resist film is dissolved in alkaline aqueous solution, the base resin (B) should preferably further comprise units having an acidic functional group protected with an acid labile group, that is, units which are protected with an acid labile group, but turn alkali soluble under the action of acid. Of the units which are protected with an acid labile group, but turn alkali soluble under the action of acid, most preferred are recurring units having the general formula (U-2).

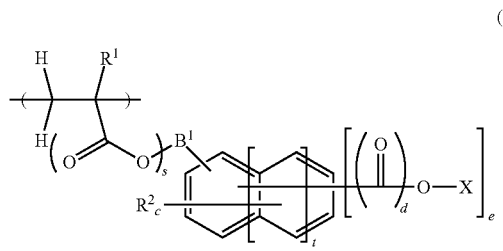
(U-2)

Herein s is 0 or 1, t is an integer of 0 to 2, $R^1$, $R^2$, and $B^1$ are as defined above, c is an integer satisfying c≤5+2t−e, d is 0 or 1, e is an integer of 1 to 3. When e is 1, X is an acid labile group. When e is 2 or 3, X is hydrogen or an acid labile group, at least one X being an acid labile group.

The unit of formula (U-2) corresponds to the unit of formula (U-1) in which at least one phenolic hydroxyl group substituting on aromatic ring is protected with an acid labile group, or a phenolic hydroxyl group is replaced by a carboxyl group which is, in turn, protected with an acid labile group. The acid labile group used herein is not particularly limited. It may be any of acid labile groups which are commonly used in many well-known chemically amplified resist compositions as long as it is eliminated with an acid to provide an acidic group.

The acid labile group is typically selected from tertiary alkyl groups and acetal groups. A choice of tertiary alkyl as the acid labile group is preferred in that when a resist film is formed as thin as 10 to 100 nm, and a fine pattern having a line width of 45 nm or less is printed therein, the pattern is provided with minimal LER. Of the tertiary alkyl groups, those of 4 to 18 carbon atoms are preferred because a corresponding monomer subject to polymerization may be recovered by distillation. In the tertiary alkyl group, suitable alkyl substituents on tertiary carbon are straight, branched or cyclic $C_1$-$C_{15}$ alkyl groups, some of which may contain an oxygen-containing functional group such as ether bond or carbonyl; and alkyl substituents on tertiary carbon may bond together to form a ring.

Examples of the alkyl substituent include methyl, ethyl, propyl, adamantyl, norbornyl, tetrahydrofuran-2-yl, 7-oxanorbornan-2-yl, cyclopentyl, 2-tetrahydrofuryl, tricyclo[5.2.1.0$^{2,6}$]decyl, tetracyclo[4.4.4.0.1$^{2,5}$.1$^{7,10}$]dodecyl, and 3-oxo-1-cyclohexyl. Suitable tertiary alkyl groups having such alkyl substituents include t-butyl, t-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

Also, an acetal group of the general formula (U-2-1) is often used as the acid labile group. It is a good choice of the acid labile group that ensures to form a pattern having a substantially rectangular pattern-substrate interface in a consistent manner.

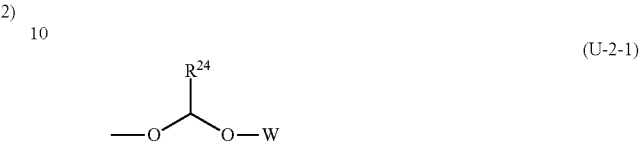
(U-2-1)

Herein $R^{24}$ is hydrogen or a straight, branched or cyclic $C_1$-$C_{10}$ alkyl group, and W is a straight, branched or cyclic $C_1$-$C_{30}$ alkyl group.

In formula (U-2-1), $R^{24}$ is hydrogen or a straight, branched or cyclic $C_1$-$C_{10}$ alkyl group. A choice of $R^{24}$ may depend on the designed sensitivity of acid labile group to acid. For example, hydrogen is selected when the acid labile group is designed to ensure relatively high stability and to be decomposed with strong acid. A straight alkyl group is selected when the acid labile group is designed to have relatively high reactivity and high sensitivity to pH changes. Although the choice varies with a particular combination of acid generator and basic compound in the resist composition. $R^{24}$ is preferably a group in which the carbon in bond with acetal carbon is secondary, when the acid labile group is designed to have a relatively large alkyl group substituted at the end and a substantial change of solubility by decomposition. Examples of $R^{24}$ bonded to acetal carbon via secondary carbon include isopropyl, sec-butyl, cyclopentyl, and cyclohexyl.

Of the acetal groups, an acetal group containing a $C_7$-$C_{30}$ polycyclic alkyl group is preferred for higher resolution. When W is a polycyclic alkyl group, a bond is preferably formed between secondary carbon on the polycyclic structure and acetal oxygen. The acetal oxygen bonded to secondary carbon on the cyclic structure, as compared with the acetal oxygen bonded to tertiary carbon, ensures that a corresponding polymer becomes a stable compound, suggesting that the resist composition has better shelf stability and is not degraded in resolution. Said acetal oxygen, as compared with W bonded to primary carbon via straight alkyl of at least one carbon atom, ensures that a corresponding polymer has a higher glass transition temperature (Tg), suggesting that a resist pattern after development is not deformed by bake.

Examples of the unit having formula (U-2-1) are given below.

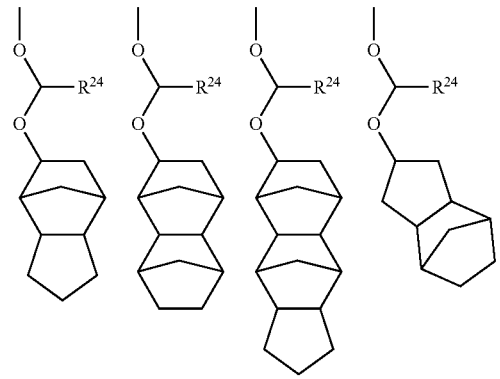

-continued

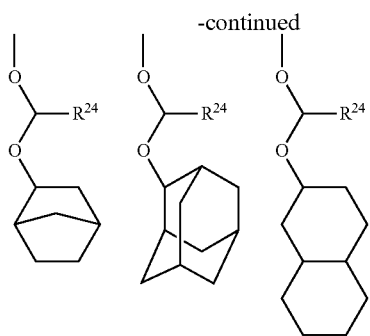

Herein $R^{24}$ is as defined above.

Another choice of acid labile group is to bond (—CH$_2$COO-tertiary alkyl) to a phenolic hydroxyl group. The tertiary alkyl group used herein may be the same as the aforementioned tertiary alkyl groups used for the protection of phenolic hydroxyl group.

The units which are protected with an acid labile group, but turn alkali soluble under the action of acid, represented by formula (U-2) may be of one type or a mixture of two or more types. In the base resin, the units having formula (U-2) are preferably incorporated in a range of 5 to 45 mol % based on the overall recurring units.

In a preferred embodiment, the base resin further comprises recurring units of at least one type selected from units of the general formulae (U-3) and (U-4).

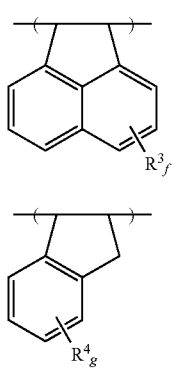

Herein f is an integer of 0 to 6, $R^3$ is each independently hydrogen, an optionally halo-substituted $C_1$-$C_6$ alkyl or primary or secondary alkoxy group, or an optionally halo-substituted $C_1$-$C_7$ alkylcarbonyloxy group, g is an integer of 0 to 4, and $R^4$ is each independently hydrogen, an optionally halo-substituted $C_1$-$C_6$ alkyl or primary or secondary alkoxy group, or an optionally halo-substituted $C_1$-$C_7$ alkylcarbonyloxy group.

Where recurring units of at least one type selected from units of formulae (U-3) and (U-4) are incorporated, the polymer may have another advantage that the binding of cyclic structure to the backbone enhances resistance to EB (to be irradiated during etching and pattern inspection), in addition to the advantage of etch resistance inherent to aromatic ring.

The recurring units which add a cyclic structure to the backbone to improve etch resistance, represented by formula (U-3) or (U-4), may be of one type or a mixture of two or more types. In the base resin, the units having formula (U-3) or (U-4) are preferably incorporated in a range of at least 5 mol % based on the overall monomer units. Where the relevant recurring unit is also a unit which exhibits polarity under the action of a functional group and imparts adhesion-to-substrate or a unit which has a substituent group protected with an acid labile group and turns alkali soluble under the action of acid, a proportion of the relevant recurring units should be added to either unit and included in the preferred range for either unit. Where the units of formula (U-3) or (U-4) have no functional groups or have a functional group which is neither of these groups, the units of formula (U-3) or (U-4) are preferably incorporated in a range of up to 30 mol % based on the overall monomer units. As long as the amount of the units free of functional groups or having a functional group which is neither of the foregoing groups is up to 30 mol %, no development defects are formed.

In the base resin, the units having formula (U-1) and optionally the units having formulae (U-2), (U-3) and (U-4) should preferably account for at least 60 mol % based on the overall monomer units. Then the resist composition has desired properties. More preferably the units having formulae (U-1) to (U-4) account for at least 70 mol %, especially at least 85 mol % based on the overall monomer units.

A base resin wherein all constituent units are selected from recurring units having formulae (U-1) to (U-4) exhibits high etch resistance and high resolution in a compatible manner. In the base resin, recurring units other than the units (U-1) to (U-4) may be incorporated. For example, (meth) acrylate units protected with a conventional acid labile group and (meth)acrylate units having an adhesive group such as lactone structure may be used. Properties of a resist film may be finely adjusted by incorporating such other recurring units although the other units need not necessarily be added.

The base resin used herein may be prepared by any well-known techniques, by selecting suitable monomers and effecting copolymerization while optionally combining protection and deprotection reactions. The copolymerization reaction is preferably radical or anionic polymerization though not limited thereto. Reference may be made to JP-A 2004-115630, for example.

The base resin used herein preferably has a weight average molecular weight (Mw) of 2,000 to 50,000, and more preferably 3,000 to 20,000, as measured by GPC using polystyrene standards. As is well known in the art, a resin with a Mw of at least 2,000 avoids the phenomenon that a pattern is rounded at the top, reduced in resolution, and degraded in LER. If Mw is higher than the necessity, there is a tendency of increasing LER, depending on a particular pattern to be resolved. Thus the resin is preferably controlled to a Mw of up to 50,000, and more preferably to a Mw of up to 20,000 particularly when a pattern with a line width of up to 100 nm is to be formed. Notably, the GPC measurement may use tetrahydrofuran (THF) solvent as commonly used.

The base resin should preferably have a narrow dispersity (Mw/Mn) of 1.0 to 2.0, especially 1.0 to 1.8. A resin with narrow dispersity avoids the phenomenon that foreign particles are left on the pattern after development or the pattern is degraded in profile.

While the base resin used herein is characterized by comprising essentially recurring units having formula (U-1) and optionally recurring units of at least one type selected from formulae (U-2) to (U-4), the base resin may further comprise recurring units of at least one type selected from the general formulae (a1), (a2) and (a3).

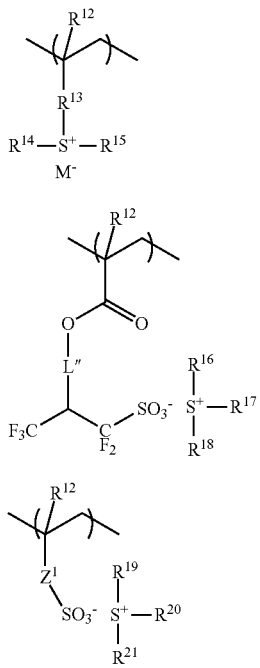

(a1)

(a2)

(a3)

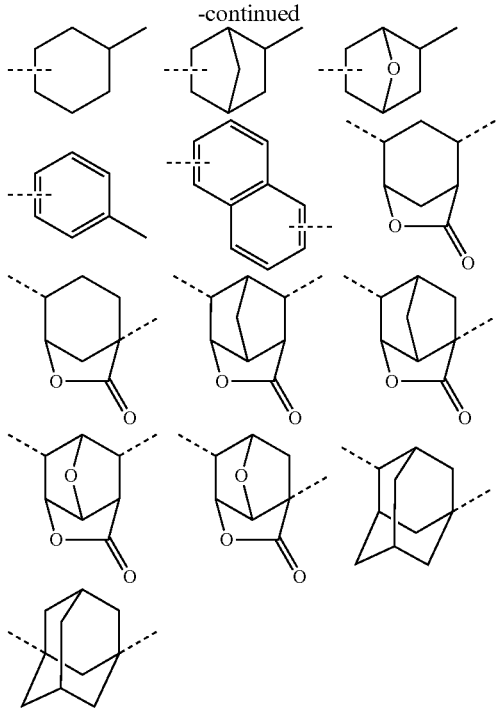
-continued

Herein R[12] is each independently hydrogen or methyl. R[13] is a single bond, phenylene, —O—R[22]—, or —C(=O)—Z[2]—R[22]—, wherein Z[2] is oxygen or NH, and R[22] is a straight, branched or cyclic $C_1$-$C_6$ alkylene, alkenylene or phenylene group, which may contain a carbonyl (—CO—), ester (—COO—), ether (—O—), or hydroxyl moiety. L″ is a single bond or —Z[3]—C(=O)—O—, wherein Z[3] is a straight, branched or cyclic $C_1$-$C_{20}$ divalent hydrocarbon group which may be substituted with or separated by a heteroatom. Z[1] is a single bond, methylene, ethylene, phenylene, fluorinated phenylene, —O—R[23]— or —C(=O)—Z[4]—R[23]—, wherein Z[4] is oxygen or NH, and R[23] is a straight, branched or cyclic $C_1$-$C_6$ alkylene, alkenylene or phenylene group, which may contain a carbonyl, ester, ether, or hydroxyl moiety. W is a non-nucleophilic counter ion. R[14], R[15], R[16], R[17], R[18], R[19], R[20], and R[21] are each independently a straight $C_1$-$C_{20}$, branched or cyclic $C_3$-$C_{20}$ monovalent hydrocarbon group in which a hydrogen atom may be substituted by a heteroatom such as oxygen, sulfur, nitrogen or halogen or in which a heteroatom such as oxygen, sulfur or nitrogen may intervene, so that a hydroxyl, cyano, carbonyl, ether bond, ester bond, sulfonic acid eater bond, carbonate bond, lactone ring, sultone ring, carboxylic anhydride or haloalkyl group may form or intervene, or a pair of R[14] and R[15] may bond together to form a ring with the sulfur atom, or any two or more of R[16], R[17] and R[18] or any two or more of R[19], R[20] and R[21] may bond together to form a ring with the sulfur atom.

In formula (a2), when L″ is —Z[3]—C(=O)—O—, Z[3] is a straight, branched or cyclic $C_1$-$C_{20}$ divalent hydrocarbon group which may be substituted with or separated by a heteroatom. Examples of the group Z[3] are shown below, but not limited thereto.

The broken line designates a valence bond.

When R[14] and R[15] bond together to form a ring with the sulfur atom, or when any two or more of R[16], R[17], and R[18], or any two or more of R[19], R[20], and R[21] bond together to form a ring with the sulfur atom, exemplary rings are shown below.

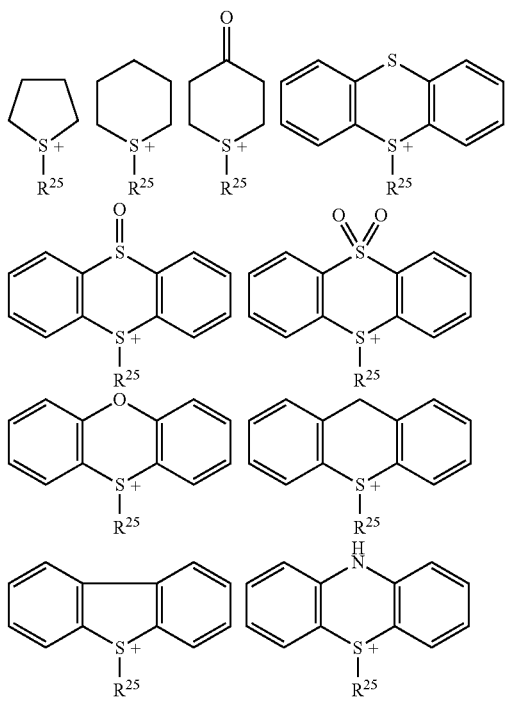

Herein R[25] is as defined and exemplified for R[14] to R[21].

Exemplary structures of the sulfonium cation in formulae (a2) and (a3) are shown below, but not limited thereto.

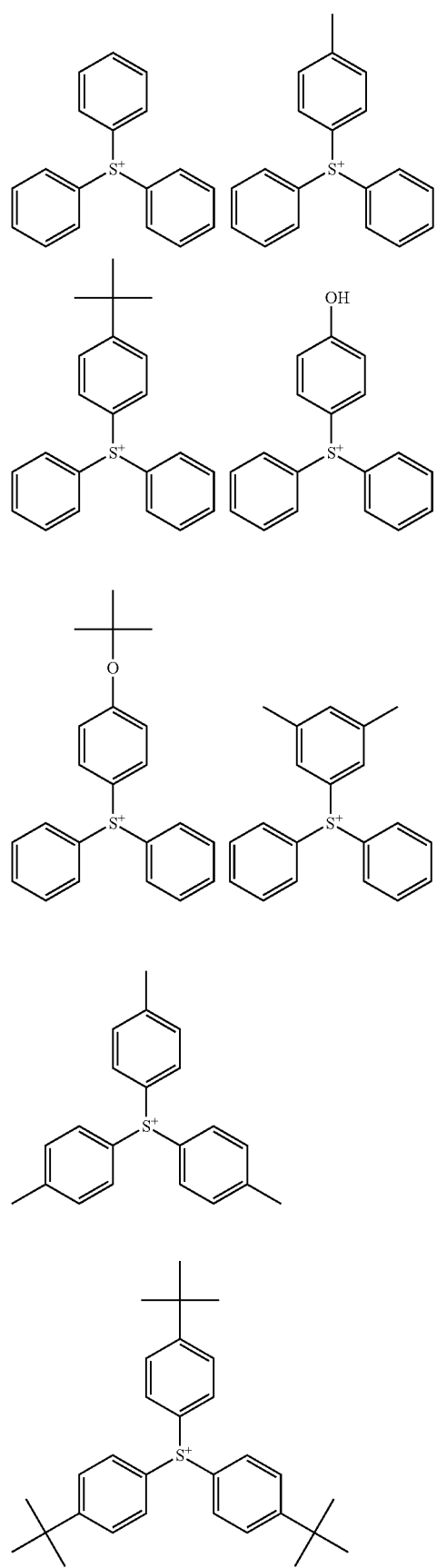

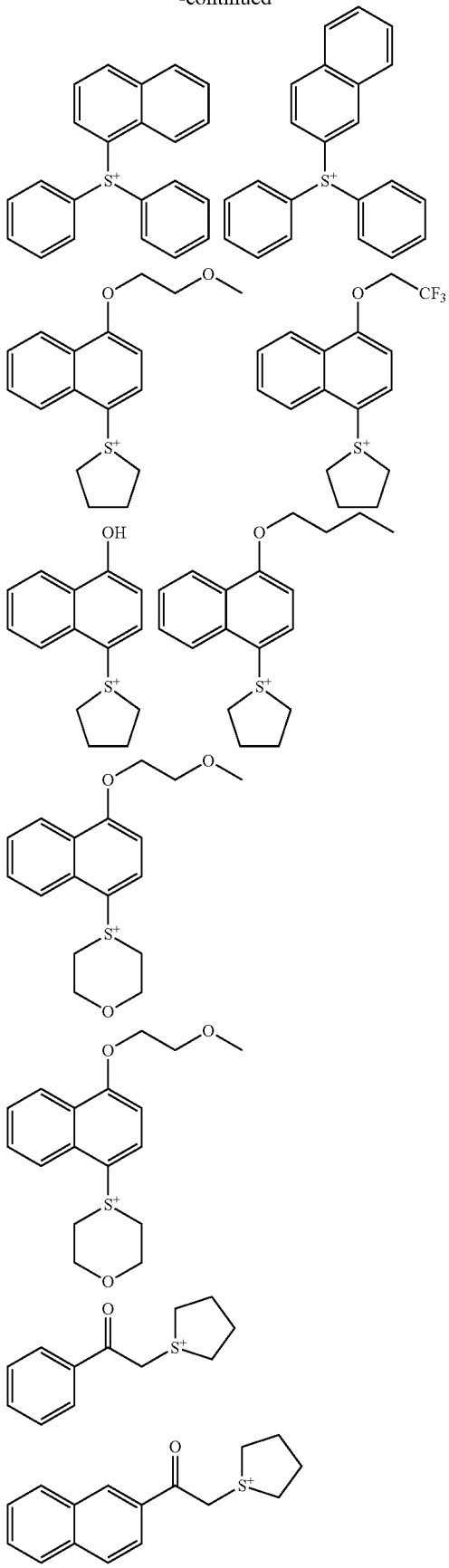

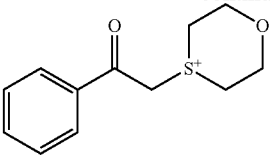

The units of formulae (a1), (a2) and (a3) are units capable of generating an acid upon receipt of high-energy radiation. With the relevant units bound into a polymer, an appropriate control of acid diffusion becomes possible, and a pattern with minimal LER can be formed.

Where the base resin comprises recurring units (a1), (a2) or (a3), the amount of such units incorporated is preferably 0.1 to 50 mol %, more preferably 1 to 30 mol % based on the overall recurring units of the base resin.

Preferably, a photoacid generator (PAG) is added to the resist composition in order that the composition function as a chemically amplified positive resist composition. The PAG may be any compound capable of generating an acid upon exposure to actinic light or high-energy radiation. Suitable PAGs include sulfonium salts, iodonium salts, sulfonyldi-azomethane, N-sulfonyloxyimide, and oxime-O-sulfonate compounds, which may be used alone or in admixture of two or more.

Examples of the PAG are described in JP-A 2008-111103, paragraphs [0122] to [0142](U.S. Pat. No. 7,537,880). Of such exemplary PAGs, those PAGs of arylsulfonate or alkanesulfonate type are preferred because they generate an acid having an appropriate strength to deprotect the acid labile group on the recurring units of formula (U-2). The preferred PAGs are compounds having a sulfonium anion of the structure shown below while a pairing cation may be any of the exemplary cations listed above for the sulfonium cation having formula (a).

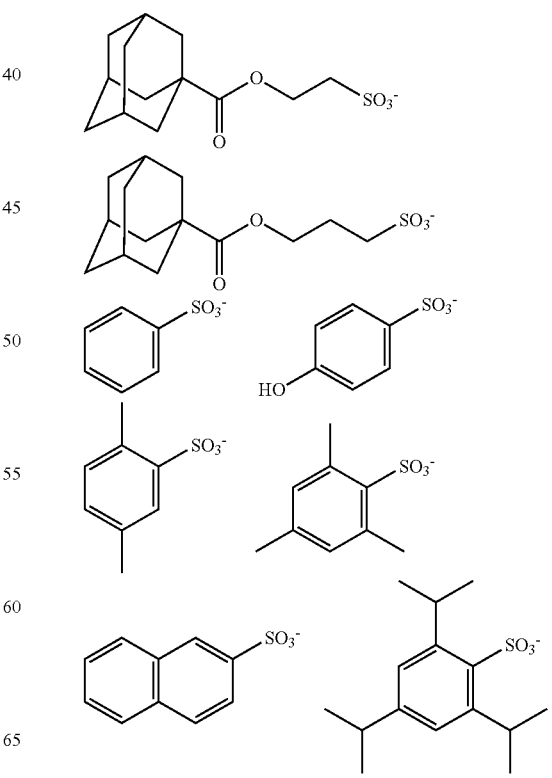

53
-continued
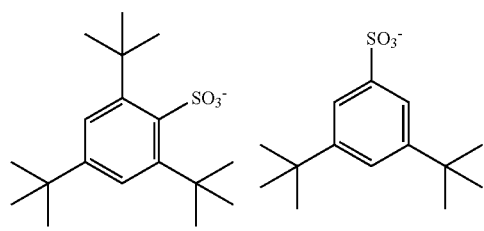
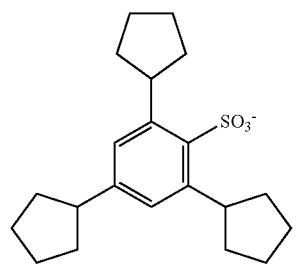
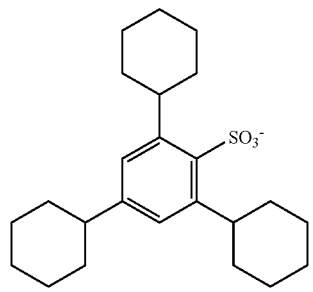
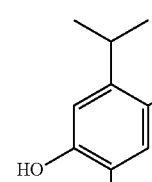
54
-continued
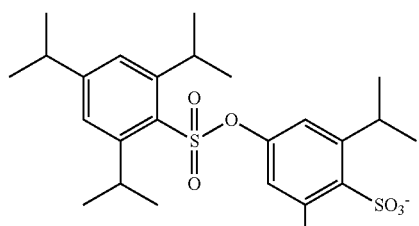
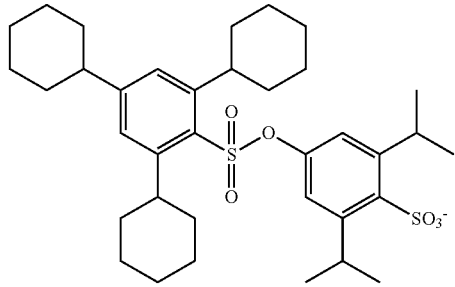
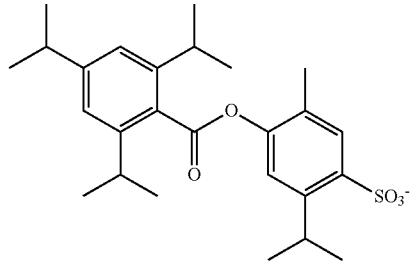
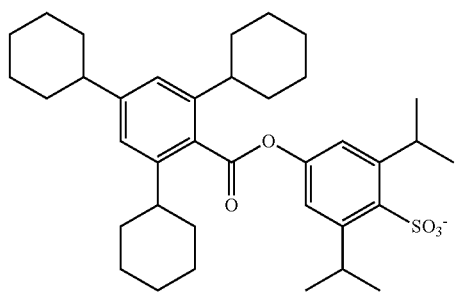
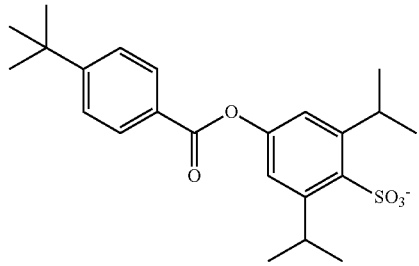
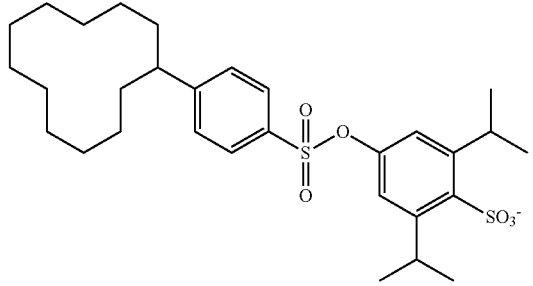

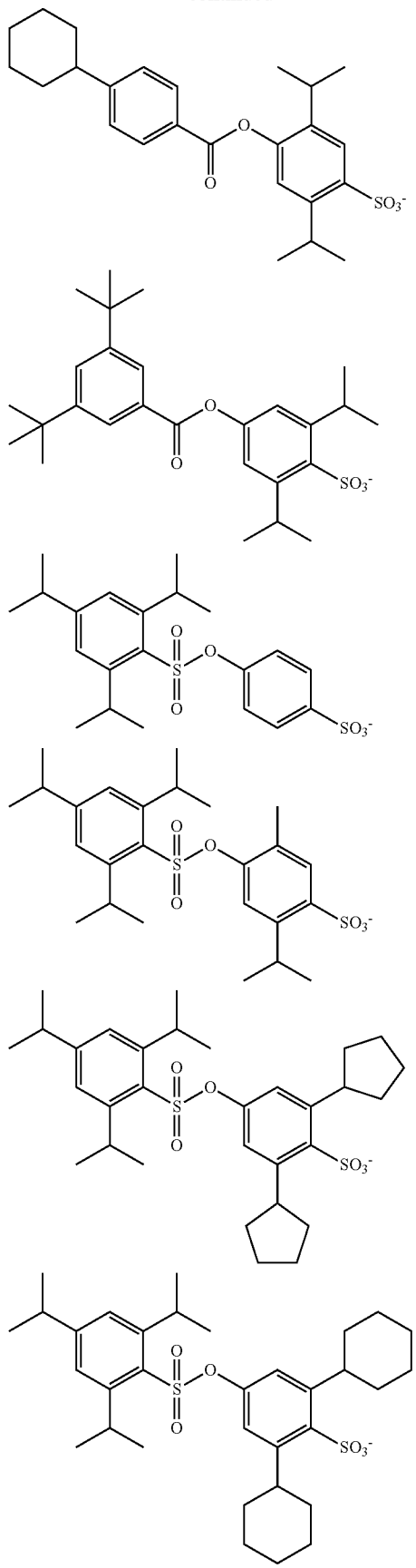
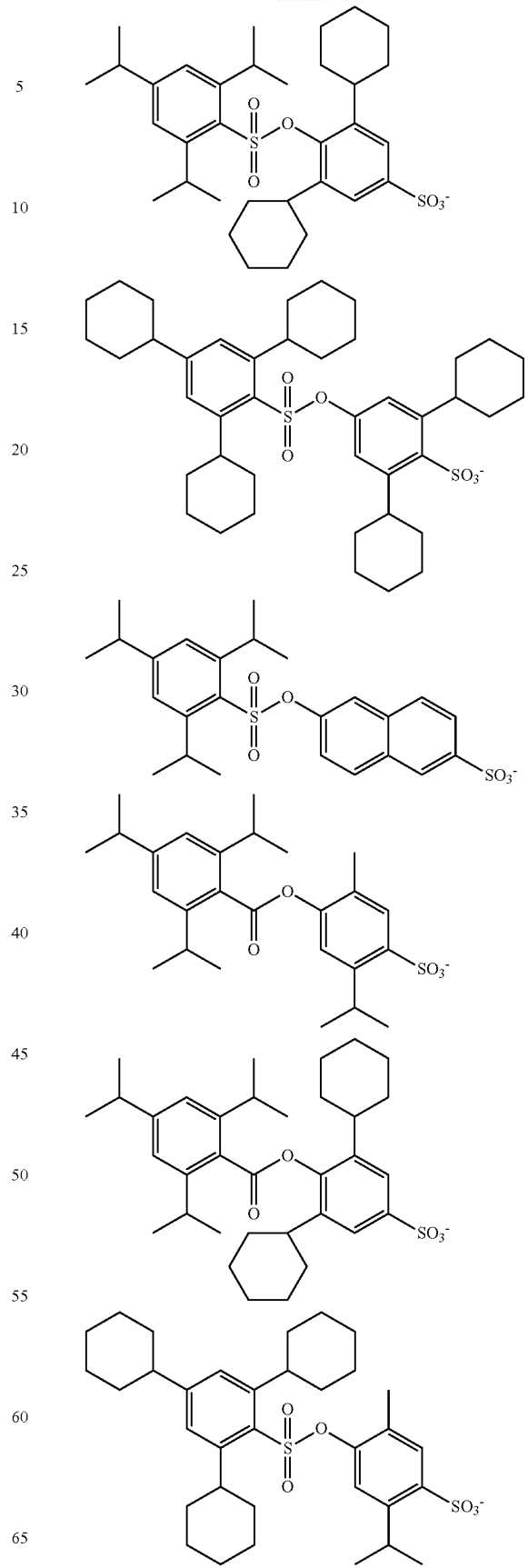

57
-continued
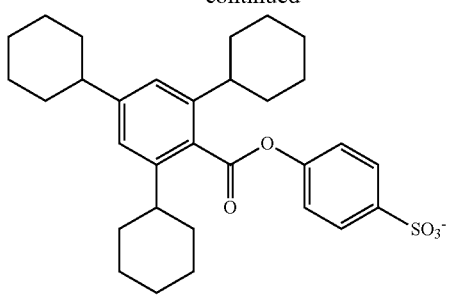
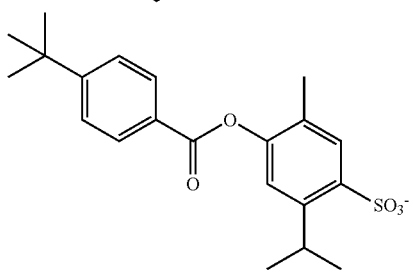
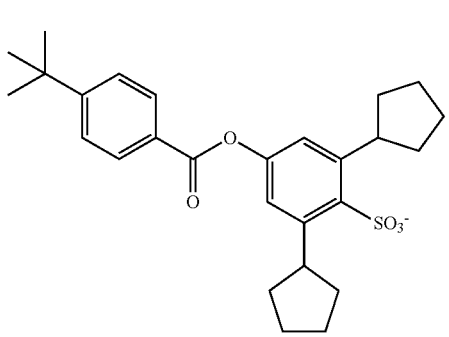
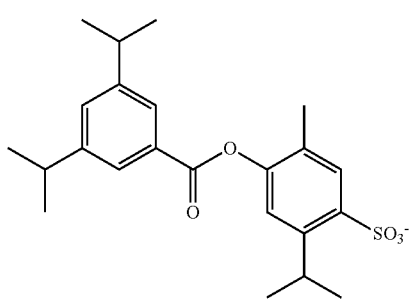
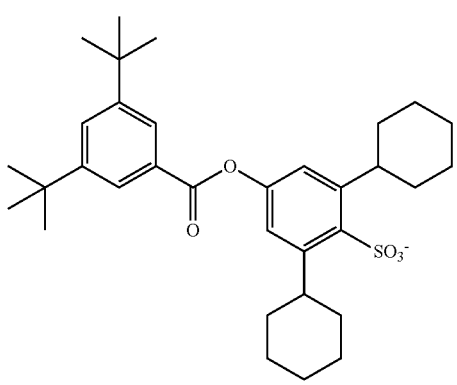
58
-continued
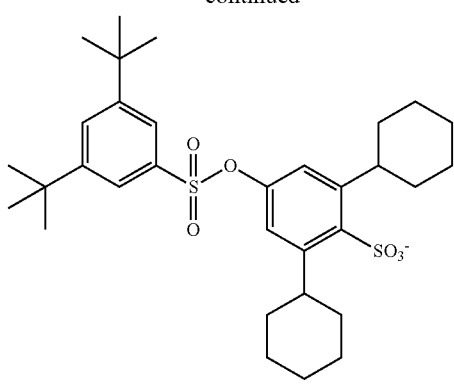
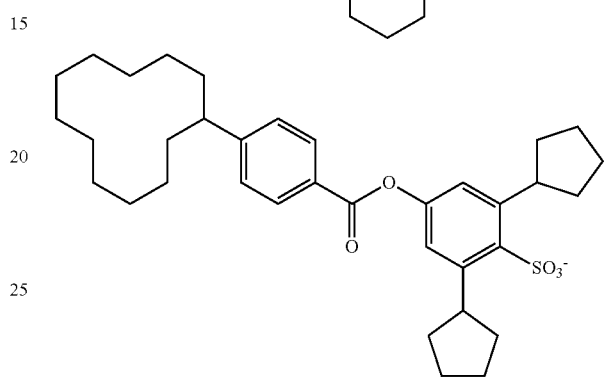
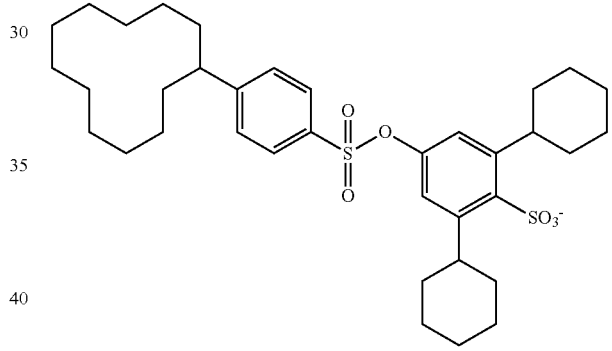
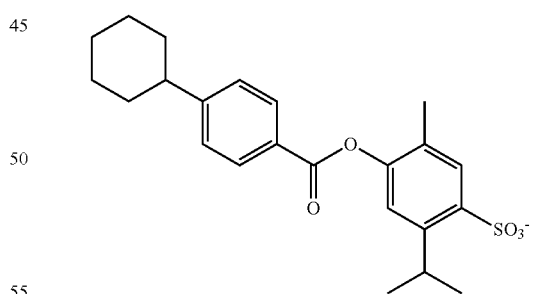
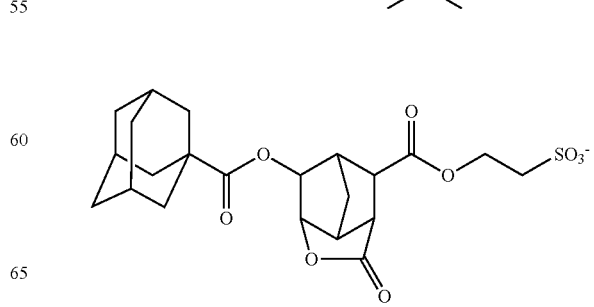

59
-continued
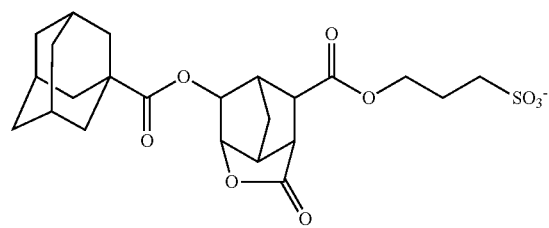
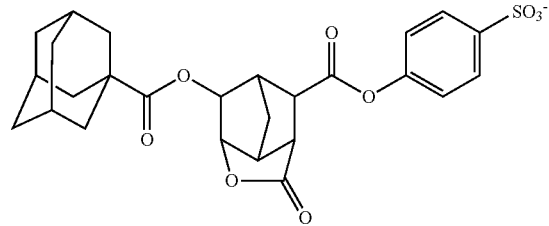
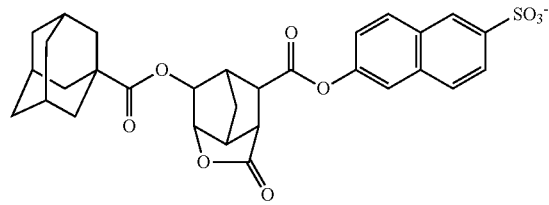
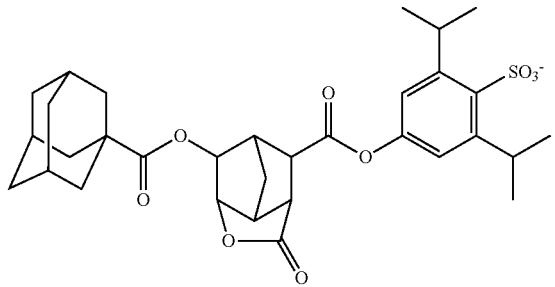
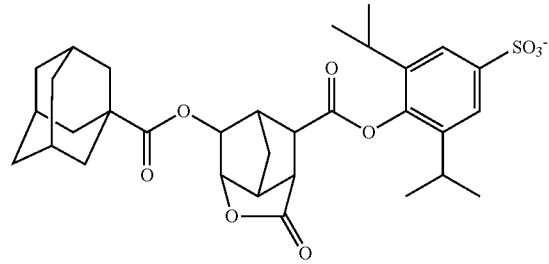
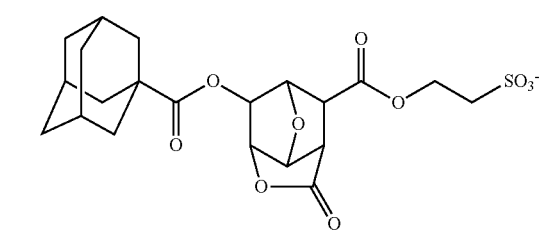
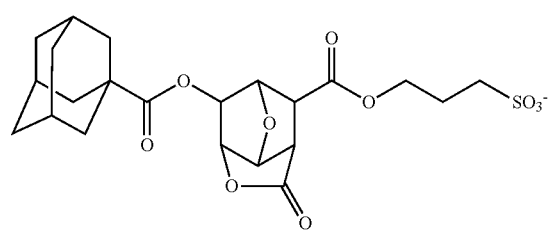
60
-continued
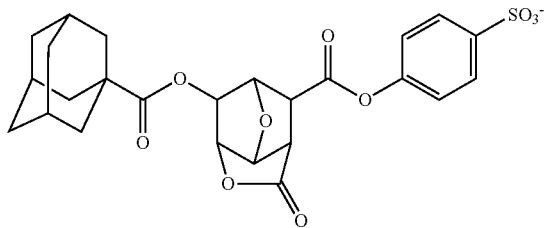
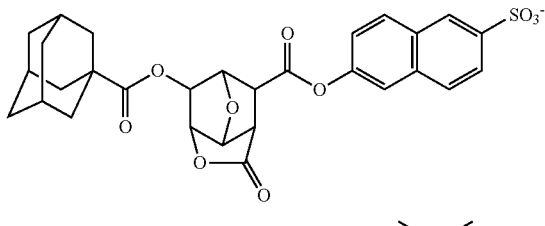
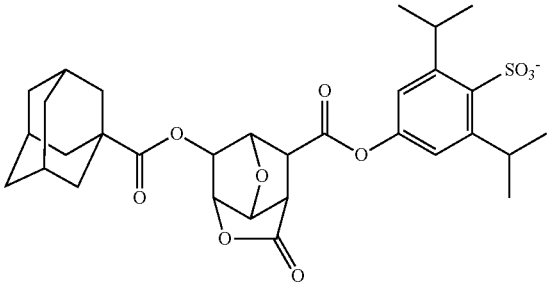
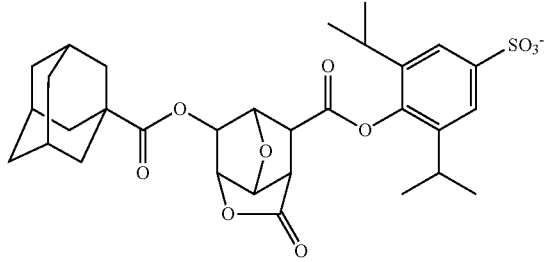
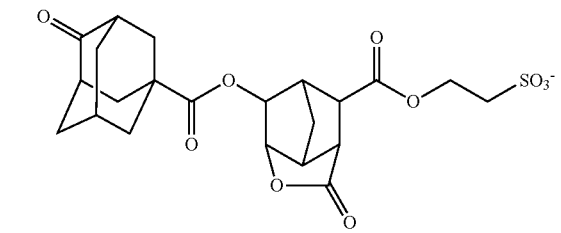
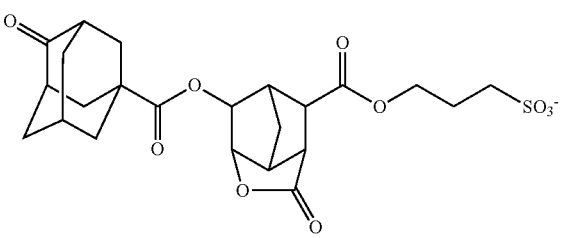
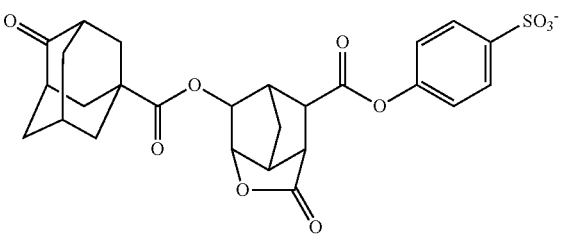

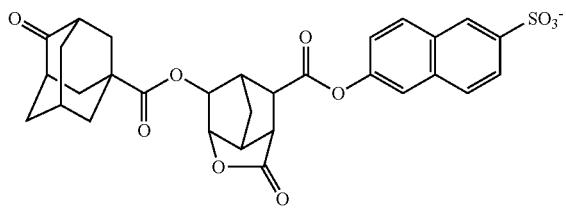
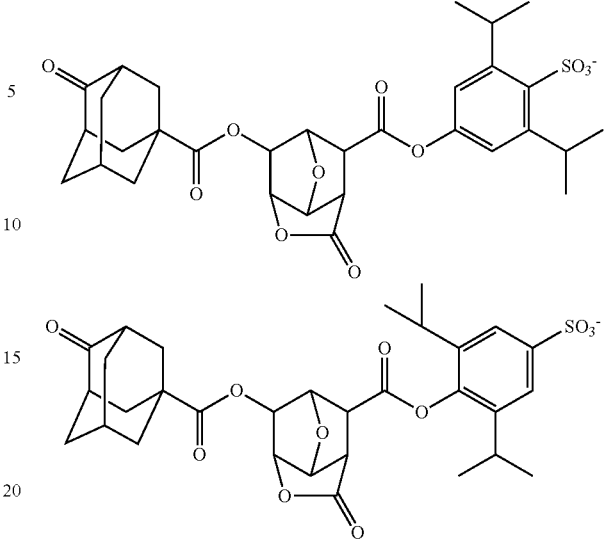

A basic compound may be added to the resist composition for the purpose of correcting pattern profile. The addition of a basic compound is effective for controlling acid diffusion and when a substrate whose outermost surface is made of a chromium-containing material is used as the processable substrate, is effective for suppressing the influence of the acid (generated in resist film) on the chromium-containing material. The basic compound is typically used in an amount of 0.01 to 5 parts, more preferably 0.05 to 3 parts by weight per 100 parts by weight of the base resin. A number of basic compounds are known. Suitable basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts. Numerous examples of these compounds are described in Patent Document 9. Any basic compounds may be used alone or in admixture of two or more. Inter alia, tris(2-(methoxymethoxy)ethyl)amine, tris[2-(methoxymethoxy)ethyl]amine N-oxide, morpholine derivatives, and imidazole derivatives are preferred.

A surfactant may be added to the resist composition. Any suitable one may be selected from those surfactants commonly used for facilitating coating operation. A number of suitable surfactants are known from JP-A 2004-115630 and other patent documents. The surfactant is typically used in an amount of up to 2 parts, more preferably 0.01 to 1 part by weight per 100 parts by weight of the base resin.

Process

Another embodiment of the invention is a pattern forming process comprising the steps of applying the resist composition onto a processable substrate to form a resist film, exposing patternwise the resist film to high-energy radiation, and developing the exposed resist film in an alkaline developer to form a resist pattern.

A pattern may be formed from the resist composition using any well-known lithography process. In general, the resist composition is applied onto a processable substrate, typically a substrate for integrated circuit fabrication (e.g., Si, SiO$_2$, SiN, SiON, TiN, WSi, BPSG, SOG or organic antireflective coating) or a substrate for mask circuit fabrication (e.g., Cr, CrO, CrON or MoSi) by a suitable coating technique such as spin coating. The coating is prebaked on a hot plate at a temperature of 60 to 150° C. for 1 to 20 minutes, preferably 80 to 140° C. for 1 to 10 minutes, to form a resist film of 0.05 to 2.0 μm thick.

The resist film is then exposed by the lithography. Specifically, the resist film is subjected to direct beam writing or exposed to high-energy radiation such as UV, DUV, excimer laser, EB, EUV, x-ray, γ-ray or synchrotron radiation through a mask having the desired pattern in a dose of 1 to 200 mJ/cm$^2$, and preferably 10 to 100 mJ/cm$^2$. The chemically amplified resist composition of the invention is best suited for pattern imaging with EUV or EB. The exposure step may be performed by standard lithography. If desired, the immersion lithography using a liquid, typically water between the mask and the resist film is applicable. In this case, a protective film which is insoluble in water may be formed on the resist film.

After exposure, the resist film is baked (PEB) on a hot plate at 60 to 150° C. for 1 to 20 minutes, and preferably at 80 to 140° C. for 1 to 10 minutes. This is followed by development in a developer which is an alkaline aqueous solution, typically an aqueous solution of 0.1 to 5 wt %, more typically 2 to 3 wt % of tetramethylammonium hydroxide (TMAH). Development may be carried out by a conventional method such as dip, puddle, or spray development for 0.1 to 3 minutes, and preferably 0.5 to 2 minutes. These steps result in the formation of the desired positive pattern on the substrate.

One advantage of the resist composition is high etch resistance. Also the resist composition is effective when it is required that the pattern experience a minimal change of line width with a post-exposure delay (PED), i.e., when the duration between exposure and PEB is prolonged. The resist composition is effectively applicable to a processable substrate, specifically a substrate having a surface layer of material to which a resist film is less adherent and which is likely to invite pattern stripping or pattern collapse, and particularly a substrate having sputter deposited thereon metallic chromium or a chromium compound containing at least one light element selected from oxygen, nitrogen and carbon. The invention is effective for pattern formation on photomask blanks.

EXAMPLE

Examples of the invention are given below by way of illustration and not by way of limitation. Mw and Mn are weight and number average molecular weights, respectively, as measured by GPC versus polystyrene standards, and Mw/Mn is a polydispersity index. The copolymer composition is computed on a molar basis. Me stands for methyl.

Synthesis Example 1-1

Synthesis of triphenylsulfonium
indole-2-carboxylate (Salt-1)

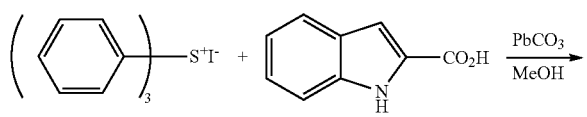

-continued

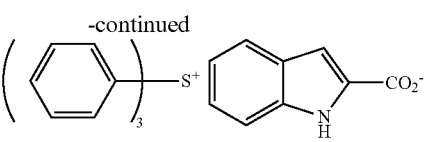

A solution of 2.4 g of indole-2-carboxylic acid, 2.0 g of lead carbonate, and 5.8 g of triphenylsulfonium iodide in 30 g of methanol was heated and stirred at 70° C. for 8 hours. The reaction solution was cooled to room temperature and filtered. The filtrate was concentrated under reduced pressure. The solid precipitate was washed with methyl isobutyl ketone and dried in vacuum, obtaining 4.8 g of the target compound, triphenylsulfonium indole-2-carboxylate. Yield 75%. The compound was analyzed by spectroscopy, with the data shown below.

IR (D-ATR): 3389, 3135, 3083, 3022, 1574, 1523, 1474, 1445, 1415, 1382, 1371, 1340, 1320, 1230, 995, 844, 826, 816, 765, 755, 748, 699, 683 cm$^{-1}$

Time-of-flight mass spectrometry (TOFMS, MALDI)
Positive M$^+$ 263 (corresponding to $(C_6H_5)_3S^+$)
Negative M$^-$ 160 (corresponding to $C_8H_6N-CO_2^-$)

Synthesis Example 1-2

Synthesis of triphenylsulfonium
4-morpholin-4-yl-benzoate (Salt-8)

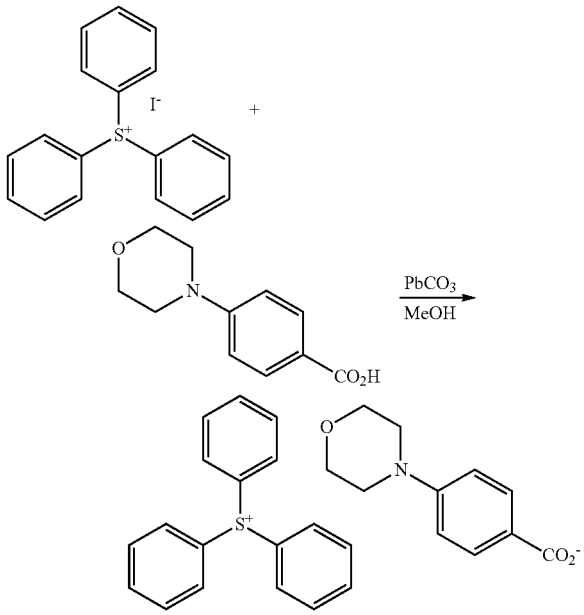

A solution of 3.1 g of 4-(4-morpholinyl)benzoic acid, 2.0 g of lead carbonate, and 5.8 g of triphenylsulfonium iodide in 30 g of methanol was heated and stirred at 70° C. for 8 hours. The reaction solution was cooled to room temperature and filtered. The filtrate was concentrated under reduced pressure. The solid precipitate was washed with methyl isobutyl ketone and dried in vacuum, obtaining 5.8 g of the target compound, triphenylsulfonium 4-morpholin-4-yl-benzoate. Yield 83%. The spectroscopic data of the compound are shown below.

IR (D-ATR): 3351, 3082, 3038, 3009, 2995, 2861, 2826, 1601, 1549, 1510, 1478, 1449, 1364, 1347, 1235, 1118, 995, 927, 792, 759, 703, 687, 658 cm$^{-1}$

TOFMS (MALDI)
Positive M+ 263 (corresponding to $(C_6H_5)_3S^+$)
Negative M− 206 (corresponding to $C_{10}H_{12}NO-CO_2^-$)

Synthesis Example 1-3

Synthesis of Salt-2 to Salt-7, Salt-9 to Salt-13
Salt-2 to Salt-7 and Salt-9 to Salt-13 were synthesized by the same procedure as in Synthesis Examples 1-1 and 1-2.

Synthesis Example 2

Synthesis of Polymers
Polymers for use in resist compositions were synthesized according to the following formulation.

Synthesis Example 2-1

Synthesis of Polymer A1
A 3-L flask was charged with 407.5 g of acetoxystyrene, 42.5 g of acenaphthylene, and 1,275 g of toluene as solvent. The reactor was cooled at −70° C. in a nitrogen atmosphere, after which vacuum pumping and nitrogen flow were repeated three times. The reactor was warmed up to room temperature, whereupon 34.7 g of 2,2′-azobis(2,4-dimethylvaleronitrile) (V-65 by Wako Pure Chemical Industries, Ltd.) was added as polymerization initiator. The reactor was heated at 55° C., whereupon reaction ran for 40 hours. With stirring, a mixture of 970 g of methanol and 180 g of water was added dropwise to the reaction solution. After 30 minutes of standing, the lower layer (polymer layer) was concentrated under reduced pressure. The polymer layer concentrate was dissolved again in 0.45 L of methanol and 0.54 L of tetrahydrofuran (THF), to which 160 g of triethylamine and 30 g of water were added. The reaction mixture was heated at 60° C. for 40 hours for deprotection reaction. The reaction solution was concentrated under reduced pressure. To the concentrate, 548 g of methanol and 112 g of acetone were added for dissolution. With stirring, 990 g of hexane was added dropwise to the solution. After 30 minutes of standing, 300 g of THF was added to the lower layer (polymer layer). With stirring, 1,030 g of hexane was added dropwise thereto. After 30 minutes of standing, the lower layer (polymer layer) was concentrated under reduced pressure. The polymer solution was neutralized with 82 g of acetic acid. The reaction solution was concentrated, dissolved in 0.3 L of acetone, and poured into 10 L of water for precipitation. The precipitate was filtered and dried, yielding 280 g of a white polymer. The polymer was analyzed by $^1$H-NMR and GPC, with the results shown below.

Copolymer Compositional Ratio
hydroxystyrene:acenaphthylene=89.3:10.7
Mw=5,000
Mw/Mn=1.63

Under acidic conditions, 100 g of the polymer was reacted with 50 g of 2-methyl-1-propenyl methyl ether. This was followed by neutralization, phase separation, and crystallization, obtaining 125 g of a polymer, designated Polymer A1.

Polymers P1, A2 and A3 were similarly synthesized.

Examples 1 to 63 and Comparative Examples 1 to 6

Preparation of Positive Resist Composition
(A) Acid diffusion regulator: inventive onium salts (Salt-1 to Salt-13) or comparative onium salt (Comparative Salt-1)
(B) Resin: polymers synthesized above (Polymers P1, A1 to A3)
(C) Photoacid generator: PAG-A to PAG-C A positive resist composition in solution form was prepared by dissolving the components in an organic solvent in accordance with the formulation shown in Tables 1 and 2, and filtering through a filter with a pore size of 0.2 μm or a nylon or UPE filter with a pore size of 0.02 μm. The organic solvents in Tables 1 and 2 are PGMEA (propylene glycol monomethyl ether acetate), EL (ethyl lactate), PGME (propylene glycol monomethyl ether), and CyH (cyclohexanone). The composition contained 0.075 part of surfactant FC-4430 (3M). The components in Tables 1 and 2 are identified below.

Acid Diffusion Regulator:

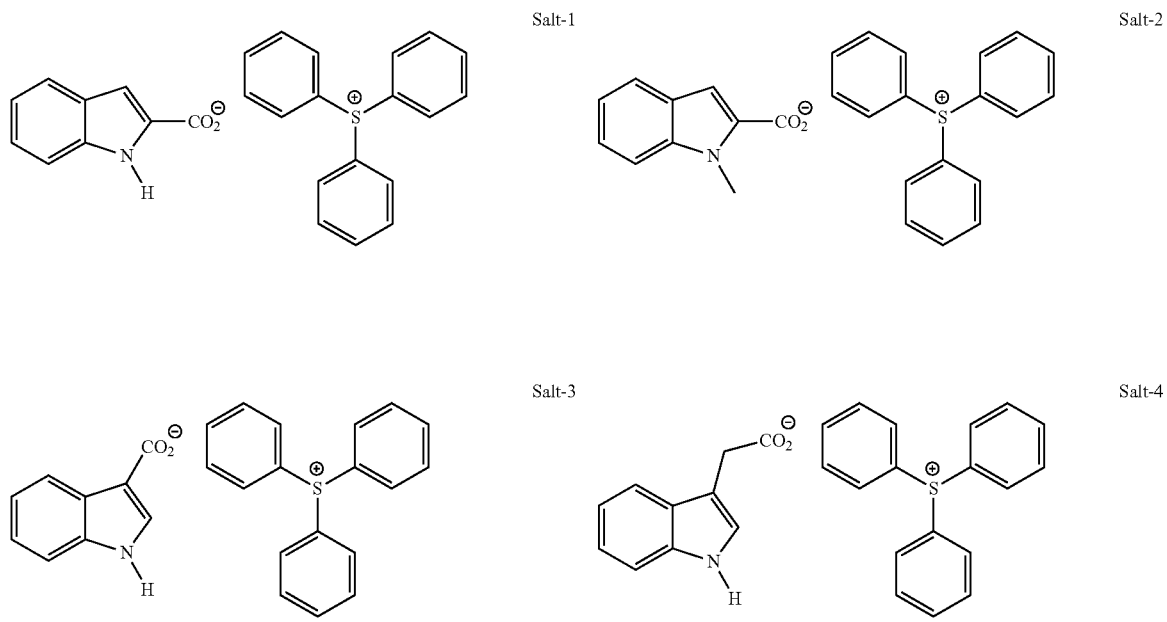

-continued
Salt-5
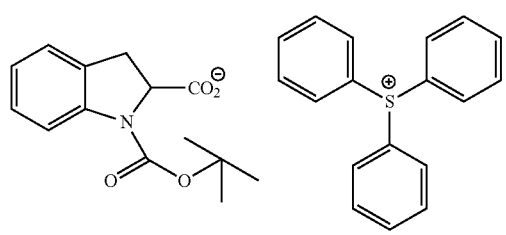
Salt-6
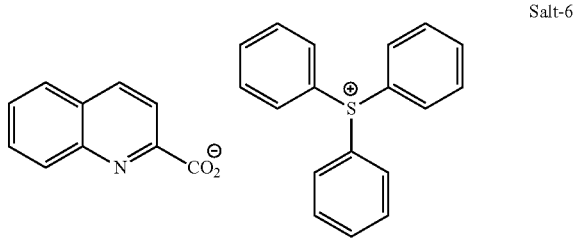
Salt-7
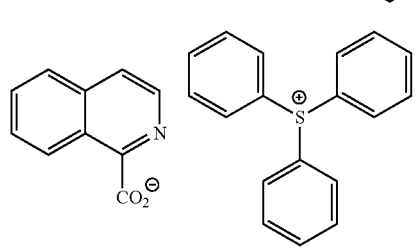
Salt-8
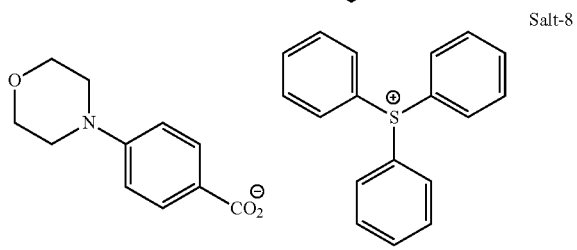
Salt-9
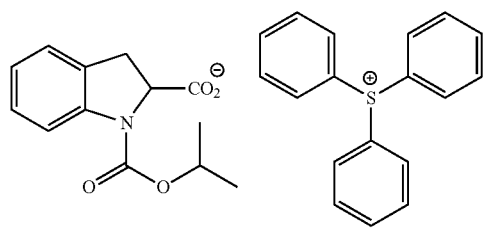
Salt-10
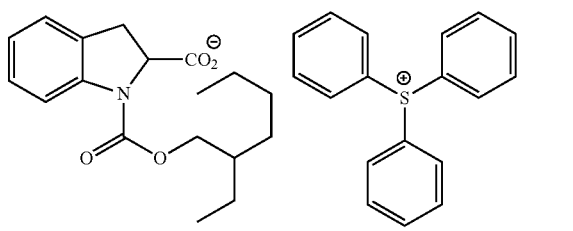
Salt-11
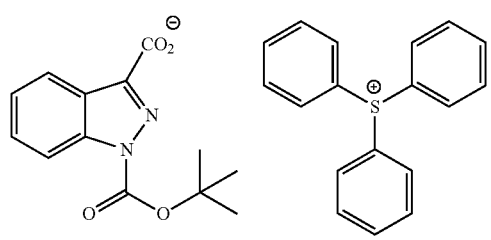
Salt-12
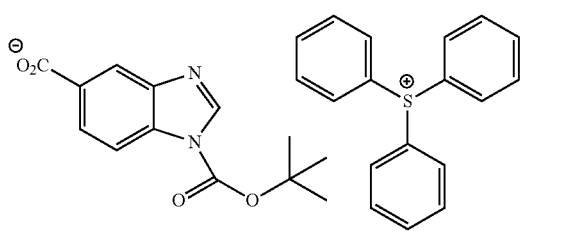
Salt-13
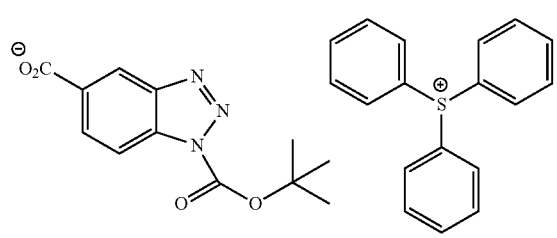
Comparative Salt-1
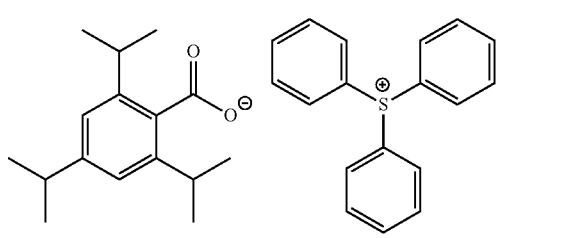
Resin 1:
Polymer P1
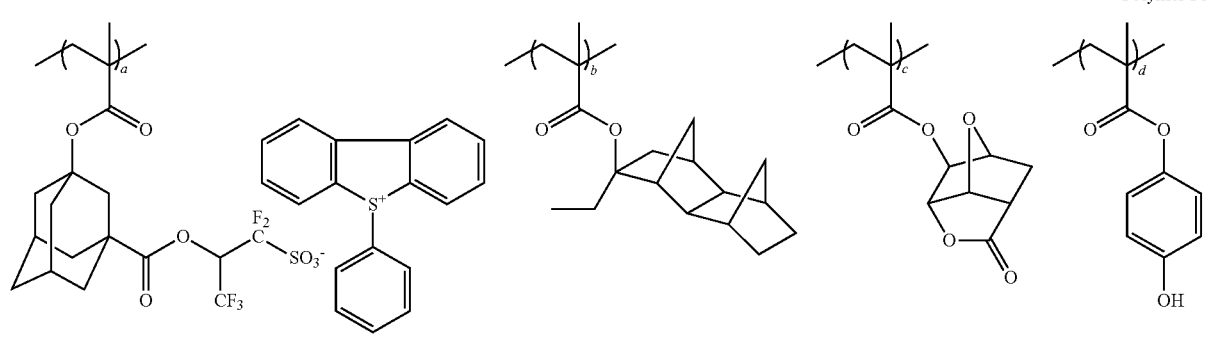
($a$ = 0.20, $b$ = 0.30, $c$ = 0.30, $d$ = 0.20, Mw = 14,500)

-continued
Resin 2:
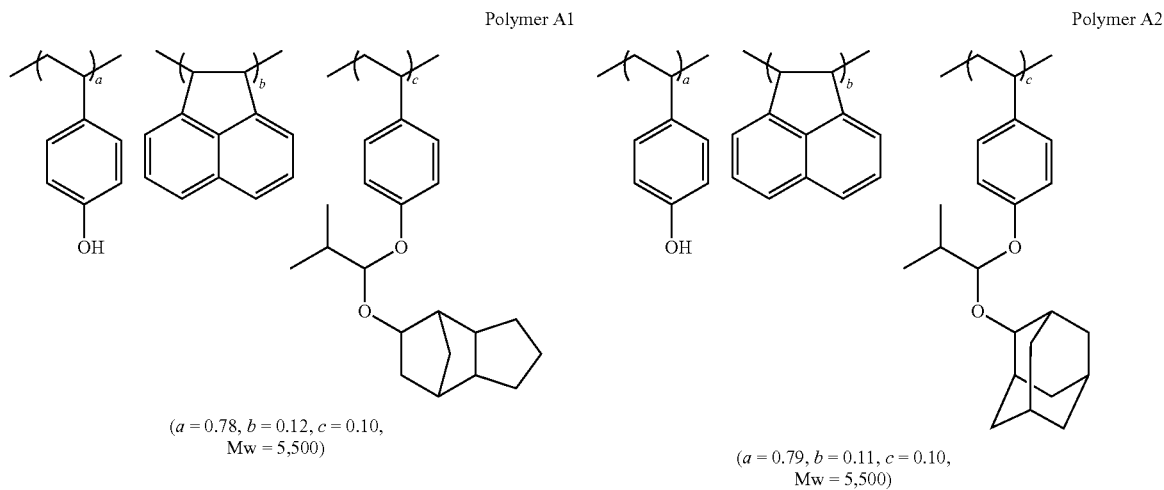
Polymer A1 ($a = 0.78, b = 0.12, c = 0.10$, Mw = 5,500)
Polymer A2 ($a = 0.79, b = 0.11, c = 0.10$, Mw = 5,500)
Polymer A3 ($a = 0.69, b = 0.10, c = 0.21$, Mw = 4,000)
Polymer (D)
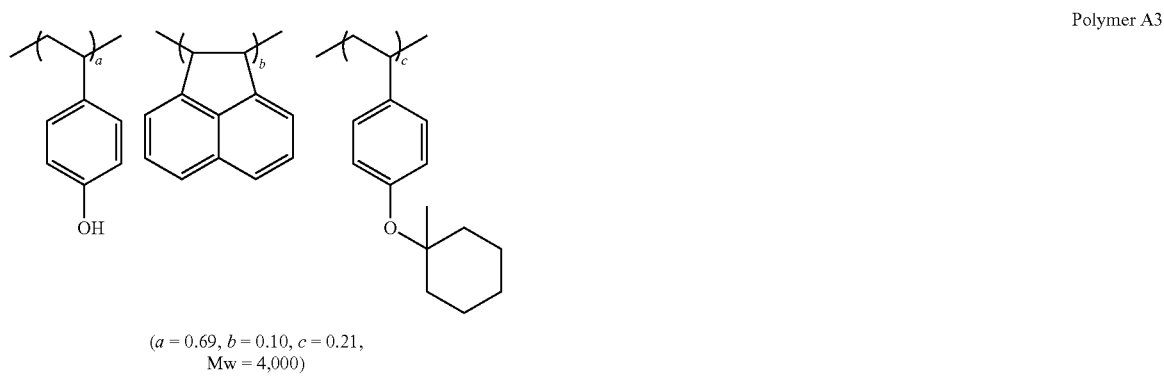
Polymer B ($a = 0.80, b = 0.20$, Mw = 6,000)
Acid generator:
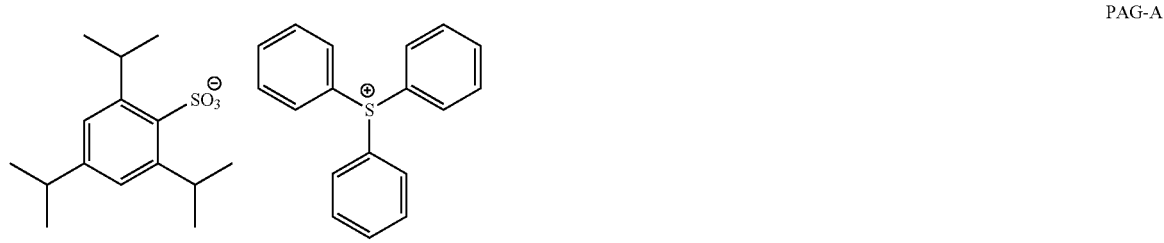
PAG-A -continued

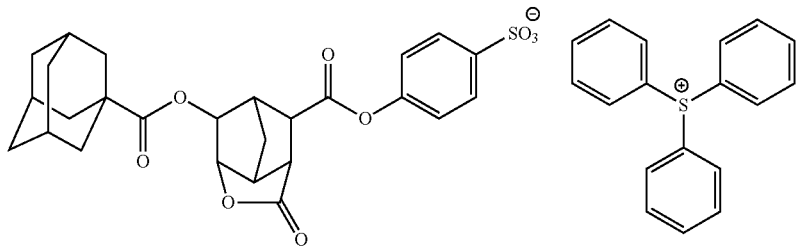

PAG-B

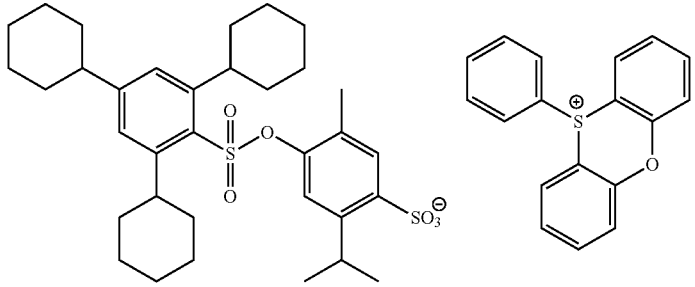

PAG-C

TABLE 1

| | | Acid diffusion regulator (pbw) | Resin 1 (pbw) | Resin 2 (pbw) | Polymer D (pbw) | Acid generator (pbw) | Solvent 1 (pbw) | Solvent 2 (pbw) | Solvent 3 (pbw) |
|---|---|---|---|---|---|---|---|---|---|
| Example | 1 | Salt-1 (3) | | Polymer A1 (80) | | PAG-A (9) | PGMEA (840) | CyH (2,130) | |
| | 2 | Salt-1 (3) | | Polymer A1 (80) | | PAG-B (9) | PGMEA (840) | CyH (2,130) | |
| | 3 | Salt-1 (3) | | Polymer A1 (80) | | PAG-C (9) | PGMEA (840) | CyH (2,130) | |
| | 4 | Salt-1 (3) | | Polymer A2 (80) | | PAG-A (9) | PGMEA (840) | CyH (2,130) | |
| | 5 | Salt-1 (3) | | Polymer A3 (80) | | PAG-A (9) | PGMEA (840) | CyH (2,130) | |
| | 6 | Salt-1 (3) | Polymer P1 (40) | Polymer A1 (40) | | | PGMEA (840) | CyH (2,130) | |
| | 7 | Salt-1 (3) | Polymer P1 (40) | Polymer A2 (40) | | | PGMEA (840) | CyH (2,130) | |
| | 8 | Salt-1 (3) | Polymer P1 (40) | Polymer A3 (40) | | | PGMEA (840) | CyH (2,130) | |
| | 9 | Salt-2 (3) | | Polymer A1 (80) | | PAG-A (9) | PGMEA (840) | CyH (2,130) | |
| | 10 | Salt-2 (3) | | Polymer A1 (80) | | PAG-B (9) | PGMEA (840) | CyH (2,130) | |
| | 11 | Salt-2 (3) | | Polymer A2 (80) | | PAG-A (9) | PGMEA (840) | CyH (2,130) | |
| | 12 | Salt-2 (3) | | Polymer A3 (80) | | PAG-A (9) | PGMEA (840) | CyH (2,130) | |
| | 13 | Salt-2 (3) | Polymer P1 (40) | Polymer A1 (40) | | | PGMEA (840) | CyH (2,130) | |
| | 14 | Salt-2 (3) | Polymer P1 (40) | Polymer A2 (40) | | | PGMEA (840) | CyH (2,130) | |
| | 15 | Salt-2 (3) | Polymer P1 (40) | Polymer A3 (40) | | | PGMEA (840) | CyH (2,130) | |
| | 16 | Salt-3 (3) | | Polymer A1 (80) | | PAG-A (9) | PGMEA (255) | EL (1,640) | PGME (1,310) |
| | 17 | Salt-3 (3) | | Polymer A2 (80) | | PAG-A (9) | PGMEA (255) | EL (1,640) | PGME (1,310) |
| | 18 | Salt-3 (3) | | Polymer A3 (80) | | PAG-A (9) | PGMEA (255) | EL (1,640) | PGME (1,310) |
| | 19 | Salt-3 (3) | Polymer P1 (40) | Polymer A1 (40) | | | PGMEA (255) | EL (1,640) | PGME (1,310) |
| | 20 | Salt-3 (3) | Polymer P1 (40) | Polymer A2 (40) | | | PGMEA (255) | EL (1,640) | PGME (1,310) |
| | 21 | Salt-3 (3) | Polymer P1 (40) | Polymer A3 (40) | | | PGMEA (255) | EL (1,640) | PGME (1,310) |
| | 22 | Salt-4 (3) | | Polymer A1 (80) | | PAG-A (9) | EL (1,850) | PGME (1,280) | |

TABLE 1-continued

| | | Acid diffusion regulator (pbw) | Resin 1 (pbw) | Resin 2 (pbw) | Polymer D (pbw) | Acid generator (pbw) | Solvent 1 (pbw) | Solvent 2 (pbw) | Solvent 3 (pbw) |
|---|---|---|---|---|---|---|---|---|---|
| | 23 | Salt-4 (3) | | Polymer A2 (80) | | PAG-A (9) | EL (1,850) | PGME (1,280) | |
| | 24 | Salt-4 (3) | | Polymer A3 (80) | | PAG-A (9) | EL (1,850) | PGME (1,280) | |
| | 25 | Salt-4 (3) | Polymer P1 (40) | Polymer A1 (40) | | | EL (1,850) | PGME (1,280) | |
| | 26 | Salt-5 (2.5) | | Polymer A1 (80) | | PAG-A (9) | PGMEA (840) | CyH (2,130) | |
| | 27 | Salt-5 (2.5) | | Polymer A2 (80) | | PAG-A (9) | PGMEA (840) | CyH (2,130) | |
| | 28 | Salt-5 (2.5) | | Polymer A2 (80) | | PAG-C (9) | PGMEA (840) | CyH (2,130) | |
| | 29 | Salt-5 (2.5) | | Polymer A2 (80) | Polymer B (3) | PAG-C (9) | PGMEA (840) | CyH (2,130) | |
| | 30 | Salt-5 (2.5) | | Polymer A3 (80) | | PAG-A (9) | PGMEA (840) | CyH (2,130) | |
| | 31 | Salt-5 (2.5) | Polymer P1 (40) | Polymer A1 (40) | | | PGMEA (840) | CyH (2,130) | |
| | 32 | Salt-6 (2.2) | | Polymer A1 (80) | | PAG-A (9) | PGMEA (840) | CyH (2,130) | |
| | 33 | Salt-6 (2.2) | | Polymer A2 (80) | | PAG-A (9) | PGMEA (840) | CyH (2,130) | |
| | 34 | Salt-6 (2.2) | | Polymer A3 (80) | | PAG-A (9) | PGMEA (840) | CyH (2,130) | |
| | 35 | Salt-6 (2.2) | Polymer P1 (40) | Polymer A1 (40) | | | PGMEA (840) | CyH (2,130) | |
| | 36 | Salt-7 (2.0) | | Polymer A1 (80) | | PAG-A (9) | PGMEA (840) | CyH (2,130) | |
| | 37 | Salt-7 (2.0) | | Polymer A2 (80) | | PAG-A (9) | PGMEA (840) | CyH (2,130) | |
| | 38 | Salt-7 (2.0) | | Polymer A3 (80) | | PAG-A (9) | PGMEA (840) | CyH (2,130) | |
| | 39 | Salt-7 (2.0) | Polymer P1 (40) | Polymer A1 (40) | | | PGMEA (840) | CyH (2,130) | |

TABLE 2

| | | Acid diffusion regulator (pbw) | Resin 1 (pbw) | Resin 2 (pbw) | Polymer D (pbw) | Acid generator (pbw) | Solvent 1 (pbw) | Solvent 2 (pbw) | Solvent 3 (pbw) |
|---|---|---|---|---|---|---|---|---|---|
| Example | 40 | Salt-8 (2.2) | | Polymer A1 (80) | | PAG-A (9) | PGMEA (840) | CyH (2,130) | |
| | 41 | Salt-8 (2.2) | | Polymer A1 (80) | | PAG-B (9) | PGMEA (840) | CyH (2,130) | |
| | 42 | Salt-8 (2.2) | | Polymer A2 (80) | | PAG-A (9) | PGMEA (840) | CyH (2,130) | |
| | 43 | Salt-8 (2.2) | | Polymer A3 (80) | | PAG-A (9) | PGMEA (840) | CyH (2,130) | |
| | 44 | Salt-8 (2.2) | Polymer P1 (40) | Polymer A1 (40) | | | PGMEA (840) | CyH (2,130) | |
| | 45 | Salt-9 (3.1) | | Polymer A1 (80) | | PAG-A (9) | PGMEA (840) | EL (2,130) | |
| | 46 | Salt-9 (3.1) | | Polymer A2 (80) | | PAG-A (9) | PGMEA (840) | EL (2,130) | |
| | 47 | Salt-9 (3.1) | | Polymer A2 (80) | | PAG-C (9) | PGMEA (840) | EL (2,130) | |
| | 48 | Salt-9 (3.1) | | Polymer A2 (80) | Polymer B (3) | PAG-C (9) | PGMEA (840) | EL (2,130) | |
| | 49 | Salt-9 (3.1) | Polymer P1 (40) | Polymer A1 (40) | | | PGMEA (840) | EL (2,130) | |
| | 50 | Salt-10 (3.0) | | Polymer A1 (80) | | PAG-A (9) | PGMEA (840) | EL (2,130) | |
| | 51 | Salt-10 (3.0) | | Polymer A2 (80) | | PAG-A (9) | PGMEA (840) | EL (2,130) | |
| | 52 | Salt-10 (3.0) | | Polymer A2 (80) | | PAG-C (9) | PGMEA (840) | EL (2,130) | |
| | 53 | Salt-10 (3.0) | | Polymer A2 (80) | Polymer B (3) | PAG-C (9) | PGMEA (840) | EL (2,130) | |
| | 54 | Salt-10 (3.0) | Polymer P1 (40) | Polymer A1 (40) | | | PGMEA (840) | EL (2,130) | |
| | 55 | Salt-11 (2.4) | | Polymer A2 (80) | | PAG-A (9) | PGMEA (840) | EL (2,130) | |

TABLE 2-continued

|  |  | Acid diffusion regulator (pbw) | Resin 1 (pbw) | Resin 2 (pbw) | Polymer D (pbw) | Acid generator (pbw) | Solvent 1 (pbw) | Solvent 2 (pbw) | Solvent 3 (pbw) |
|---|---|---|---|---|---|---|---|---|---|
|  | 56 | Salt-11 (2.4) |  | Polymer A2 (80) |  | PAG-C (9) | PGMEA (840) | EL (2,130) |  |
|  | 57 | Salt-11 (2.4) |  | Polymer A2 (80) | Polymer B (3) | PAG-C (9) | PGMEA (840) | EL (2,130) |  |
|  | 58 | Salt-12 (2.2) |  | Polymer A2 (80) |  | PAG-A (9) | PGMEA (840) | EL (2,130) |  |
|  | 59 | Salt-12 (2.2) |  | Polymer A2 (80) |  | PAG-C (9) | PGMEA (840) | EL (2,130) |  |
|  | 60 | Salt-12 (2.2) |  | Polymer A2 (80) | Polymer B (3) | PAG-C (9) | PGMEA (840) | EL (2,130) |  |
|  | 61 | Salt-13 (2.1) |  | Polymer A2 (80) |  | PAG-A (9) | PGMEA (840) | EL (2,130) |  |
|  | 62 | Salt-13 (2.1) |  | Polymer A2 (80) |  | PAG-C (9) | PGMEA (840) | EL (2,130) |  |
|  | 63 | Salt-13 (2.1) |  | Polymer A2 (80) | Polymer B (3) | PAG-C (9) | PGMEA (840) | EL (2,130) |  |
| Comparative Example | 1 | Comparative Salt-1 (4) |  | Polymer A1 (80) |  | PAG-A (9) | PGMEA (840) | CyH (2,130) |  |
|  | 2 | Comparative Salt-1 (4) |  | Polymer A1 (80) |  | PAG-B (9) | PGMEA (840) | CyH (2,130) |  |
|  | 3 | Comparative Salt-1 (4) |  | Polymer A1 (80) |  | PAG-C (9) | PGMEA (840) | CyH (2,130) |  |
|  | 4 | Comparative Salt-1 (4) |  | Polymer A2 (80) |  | PAG-A (9) | PGMEA (840) | CyH (2,130) |  |
|  | 5 | Comparative Salt-1 (4) |  | Polymer A3 (80) |  | PAG-A (9) | PGMEA (840) | CyH (2,130) |  |
|  | 6 | Comparative Salt-1 (4) | Polymer P1 (40) | Polymer A1 (40) |  |  | PGMEA (840) | CyH (2,130) |  |

EB Writing Test

Using a coater/developer system ACT-M (Tokyo Electron Ltd.), each of the positive resist compositions (Examples 1 to 63 and Comparative Examples 1 to 6) was spin coated onto a mask blank of 152 mm squares having a chromium oxynitride film at the outermost surface and prebaked on a hot plate at 110° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 m inward from the blank periphery, and an average film thickness and a film thickness range were computed therefrom.

The coated mask blanks were exposed to EB using an EB writer system EBM-5000Plus (NuFlare Technology Inc., accelerating voltage 50 keV), then baked (PEB) at 90° C. for 600 seconds, and developed in a 2.38 wt % tetramethylammonium hydroxide (TMAH) aqueous solution, thereby yielding positive patterns.

The patterned mask blank was observed under a top-down scanning electron microscope (TD-SEM). The optimum exposure (Eop) was defined as the exposure dose ($\mu C/cm^2$) which provided a 1:1 resolution at the top and bottom of a 400-nm 1:1 line-and-space pattern. The maximum resolution of the resist was defined as the minimum line width of a line-and-space pattern that could be resolved at the optimum exposure. The LER of a 200-nm line-and-space pattern was measured under SEM. On observation in cross section of the resist pattern under SEM, it was visually judged whether or not the pattern profile was rectangular. The test results of the resist compositions are shown in Tables 3 and 4.

TABLE 3

|  |  | Eop. $\mu C/cm^2$ | Maximum resolution, nm | LER, nm | Pattern profile |
|---|---|---|---|---|---|
| Example | 1 | 50 | 35 | 4.5 | rectangular |
|  | 2 | 50 | 40 | 4.8 | rectangular |
|  | 3 | 49 | 35 | 4.4 | rectangular |
|  | 4 | 50 | 35 | 4.7 | rectangular |
|  | 5 | 51 | 35 | 4.6 | rectangular |
|  | 6 | 52 | 35 | 4.4 | rectangular |
|  | 7 | 50 | 35 | 4.5 | rectangular |
|  | 8 | 49 | 35 | 4.5 | rectangular |
|  | 9 | 48 | 35 | 4.7 | rectangular |
|  | 10 | 49 | 40 | 4.8 | rectangular |
|  | 11 | 50 | 35 | 4.7 | rectangular |
|  | 12 | 50 | 35 | 4.7 | rectangular |
|  | 13 | 49 | 35 | 4.6 | rectangular |
|  | 14 | 50 | 35 | 4.4 | rectangular |
|  | 15 | 51 | 35 | 4.5 | rectangular |
|  | 16 | 51 | 35 | 4.8 | rectangular |
|  | 17 | 50 | 35 | 4.7 | rectangular |
|  | 18 | 50 | 35 | 4.8 | rectangular |
|  | 19 | 50 | 35 | 4.5 | rectangular |
|  | 20 | 51 | 35 | 4.5 | rectangular |
|  | 21 | 51 | 35 | 4.6 | rectangular |
|  | 22 | 52 | 35 | 4.7 | rectangular |
|  | 23 | 52 | 35 | 4.8 | rectangular |
|  | 24 | 51 | 35 | 4.7 | rectangular |
|  | 25 | 52 | 35 | 4.6 | rectangular |
|  | 26 | 51 | 40 | 4.5 | rectangular |
|  | 27 | 51 | 40 | 4.5 | rectangular |
|  | 28 | 51 | 35 | 4.4 | rectangular |
|  | 29 | 50 | 35 | 4.3 | rectangular |
|  | 30 | 52 | 40 | 4.6 | rectangular |
|  | 31 | 52 | 35 | 4.4 | rectangular |
|  | 32 | 52 | 40 | 4.6 | rectangular |

TABLE 3-continued

|  | Eop. µC/cm² | Maximum resolution, nm | LER, nm | Pattern profile |
|---|---|---|---|---|
| 33 | 51 | 40 | 4.6 | rectangular |
| 34 | 52 | 40 | 4.6 | rectangular |
| 35 | 52 | 40 | 4.5 | rectangular |
| 36 | 51 | 40 | 4.5 | rectangular |
| 37 | 52 | 40 | 4.4 | rectangular |
| 38 | 52 | 40 | 4.4 | rectangular |
| 39 | 53 | 35 | 4.4 | rectangular |

TABLE 4

|  |  | Eop. µC/cm² | Maximum resolution, nm | LER, nm | Pattern profile |
|---|---|---|---|---|---|
| Example | 40 | 51 | 45 | 4.8 | rectangular |
|  | 41 | 52 | 45 | 4.9 | rectangular |
|  | 42 | 53 | 45 | 4.7 | rectangular |
|  | 43 | 52 | 45 | 4.6 | rectangular |
|  | 44 | 53 | 45 | 4.5 | rectangular |
|  | 45 | 53 | 35 | 4.5 | rectangular |
|  | 46 | 54 | 37 | 4.4 | rectangular |
|  | 47 | 52 | 35 | 4.3 | rectangular |
|  | 48 | 52 | 35 | 4.2 | rectangular |
|  | 49 | 51 | 40 | 4.8 | rectangular |
|  | 50 | 53 | 37 | 4.5 | rectangular |
|  | 51 | 52 | 40 | 4.5 | rectangular |
|  | 52 | 51 | 35 | 4.4 | rectangular |
|  | 53 | 52 | 35 | 4.3 | rectangular |
|  | 54 | 51 | 37 | 4.7 | rectangular |
|  | 55 | 51 | 40 | 4.6 | rectangular |
|  | 56 | 52 | 35 | 4.4 | rectangular |
|  | 57 | 52 | 35 | 4.3 | rectangular |
|  | 58 | 52 | 37 | 4.6 | rectangular |
|  | 59 | 51 | 35 | 4.4 | rectangular |
|  | 60 | 52 | 35 | 4.2 | rectangular |
|  | 61 | 49 | 37 | 4.6 | rectangular |
|  | 62 | 51 | 35 | 4.4 | rectangular |
|  | 63 | 52 | 35 | 4.3 | rectangular |
| Comparative Example | 1 | 49 | 55 | 5.6 | inversely tapered |
|  | 2 | 50 | 55 | 5.7 | inversely tapered |
|  | 3 | 51 | 50 | 5.2 | inversely tapered |
|  | 4 | 50 | 55 | 5.6 | inversely tapered |
|  | 5 | 49 | 55 | 5.5 | inversely tapered |
|  | 6 | 49 | 50 | 5.4 | inversely tapered |

As seen from the data in Tables 3 and 4, the salts having formulae (1) and (2) are useful acid diffusion regulators. The resist compositions of Examples 1 to 63 containing the salts having formulae (1) and (2) within the scope of the invention exhibit a high resolution, satisfactory pattern rectangularity, and acceptable values of LER. In contrast, the resist compositions of Comparative Examples 1 to 6 are inferior in resolution and LER. This is because the acid generated upon exposure diffuses into the unexposed region to induce the unwanted reaction that a few protective groups on the base resin in the unexposed region are deprotected. Since the resist composition containing the inventive salt has a higher basicity than the resist composition containing the comparative salt, the likelihood of the unwanted reaction is reduced as compared with the resist composition containing the comparative salt. As a result, a pattern with reduced roughness can be formed.

EB Writing Test after Coating of Antistatic Film

Each of the positive resist compositions (Examples 1 to 8 and Comparative Examples 1 to 6) was spin coated onto a 6-inch silicon wafer and baked at 110° C. for 240 seconds to form a resist film of 80 nm thick. Using a coater/developer system Clean Track Mark 8 (Tokyo Electron Ltd.), a conductive polymer composition was dispensed dropwise and spin coated over the entire resist film and baked on a hot plate at 90° C. for 90 seconds to form an antistatic film of 60 nm thick. The conductive polymer composition used herein was a water dispersion of polystyrene-doped polyaniline as described in Proc. of SPIE Vol. 8522 85220O-1.

The coated wafer was exposed to EB using an EB writer system HL-800D (Hitachi High-Technologies, Ltd., accelerating voltage 50 keV), then baked (PEB) at 110° C. for 240 seconds, and developed in a 2.38 wt % TMAH aqueous solution for 80 seconds, thereby yielding a positive pattern.

The patterned wafer was observed under a TD-SEM. The optimum exposure (Eop) was defined as the exposure dose (µC/cm²) which provided a 1:1 resolution at the top and bottom of a 400-nm 1:1 line-and-space pattern. The maximum resolution of the resist was defined as the minimum line width of a line-and-space pattern that could be resolved at the optimum exposure. The results are shown in Table 5.

TABLE 5

|  |  | Eop, µC/cm² | Maximum resolution, nm |
|---|---|---|---|
| Eample | 1 | 48 | 60 |
|  | 2 | 48 | 70 |
|  | 3 | 50 | 60 |
|  | 4 | 49 | 60 |
|  | 5 | 49 | 60 |
|  | 6 | 50 | 60 |
|  | 7 | 49 | 60 |
|  | 8 | 48 | 60 |
| Comparative Example | 1 | 47 | 80 |
|  | 2 | 48 | 90 |
|  | 3 | 49 | 80 |
|  | 4 | 48 | 80 |
|  | 5 | 47 | 80 |
|  | 6 | 47 | 80 |

As seen from the data in Table 5, the salts having formula (1) are useful acid diffusion regulators. The resist compositions of Examples 1 to 8 containing the salts having formula (1) within the scope of the invention exhibit a satisfactory resolution. In contrast, the resist compositions of Comparative Examples 1 to 6 are inferior in resolution. This is because the very weak acid in the antistatic film induces the unwanted reaction to deprotect a few protective groups on the base resin in the unexposed region. Since the resist composition containing the inventive salt has a higher basicity than the resist composition containing the comparative salt, the likelihood of the unwanted reaction is reduced as compared with the resist composition containing the comparative salt. As a result, a pattern with a higher resolution can be formed.

It has been demonstrated that using the resist composition within the scope of the invention, a pattern having a very high resolution and minimal LER can be formed via exposure and development. Even when the resist film is overlaid with an antistatic film, the resist composition within the scope of the invention maintains a high resolution. The pattern forming process using the resist composition within the scope of the invention is advantageous in the photolithography for semiconductor device fabrication and photomask blank processing.

While the invention has been illustrated and described in typical embodiments, it is not intended to be limited to the details shown. Any modified embodiments having substantially the same features and achieving substantially the same results as the technical idea disclosed herein are within the spirit and scope of the invention.

Japanese Patent Application No. 2015-035218 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A chemically amplified positive resist composition for high-energy radiation lithography, comprising (A) an onium salt compound having the general formula (1) or (2) and (B) a resin comprising recurring units having the general formula (U-1), adapted to be decomposed under the action of acid to increase its solubility in alkaline developer,

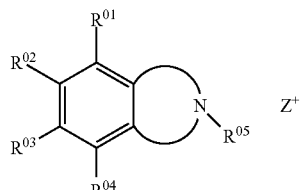
(1)

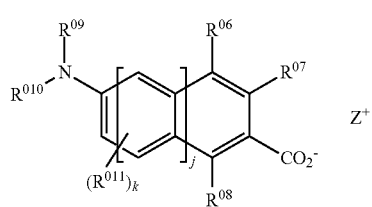
(2)

wherein $R^{01}$, $R^{02}$, $R^{03}$ and $R^{04}$ are each independently hydrogen, $-L-CO_2^-$, or a straight $C_1$-$C_{20}$, branched or cyclic $C_3$-$C_{20}$ monovalent hydrocarbon group which may be substituted with or separated by a heteroatom, or a pair of $R^{01}$ and $R^{02}$, $R^{02}$ and $R^{03}$, or $R^{03}$ and $R^{04}$ may bond together to form a ring with the carbon atoms to which they are attached, L is a single bond or a straight $C_1$-$C_{20}$, branched or cyclic $C_3$-$C_{20}$ divalent hydrocarbon group which may be substituted with or separated by a heteroatom, $R^{05}$ is hydrogen or a straight $C_1$-$C_{20}$, branched or cyclic $C_3$-$C_{20}$ monovalent hydrocarbon group which may be substituted with or separated by a heteroatom;

wherein in formula (1), the partial structure represented by the formula:

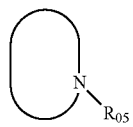

is a cyclic structure having the intervening nitrogen atom in which a hydrogen atom bonded to a cyclic structure-forming carbon atom may be replaced by a straight $C_1$-$C_{20}$, branched or cyclic $C_3$-$C_{20}$ monovalent hydrocarbon group or $-L-CO_2^-$, or in which a cyclic structure-forming carbon atom may be replaced by sulfur, oxygen or nitrogen, with the proviso that one substituent: $-L-CO_2^-$ is essentially included in formula (1), and $R^{06}$, $R^{07}$, $R^{08}$ and $R^{011}$ are each independently hydrogen or a straight $C_1$-$C_{20}$, branched or cyclic $C_3$-$C_{20}$ monovalent hydrocarbon group which may be substituted with or separated by a heteroatom, and $R^{09}$ and $R^{010}$ are both hydrogen or each independently a straight $C_1$-$C_{20}$, branched or cyclic $C_3$-$C_{20}$ monovalent hydrocarbon group which may be substituted with or separated by a heteroatom, or a pair of $R^{06}$ and $R^{07}$ may bond together to form a ring with the carbon atoms to which they are attached, a pair of $R^{08}$ and $R^{011}$ may bond together to form a ring with the carbon atoms to which they are attached and any intervening carbon atoms, or a pair of $R^{09}$ and $R^{010}$ may bond together to form a ring with the nitrogen atom, j is 0 or 1, k is a number in the range: $0 \leq k \leq 1$ when j=0, or $0 \leq k \leq 3$ when j=1, and $Z^+$ is a sulfonium cation of the general formula (a) or an iodonium cation of the general formula (b):

wherein $R^{100}$, $R^{200}$, and $R^{300}$ are each independently a straight $C_1$-$C_{20}$, branched or cyclic $C_3$-$C_{20}$ monovalent hydrocarbon group which may be substituted with or separated by a heteroatom, or any two or more of $R^{100}$, $R^{200}$, and $R^{300}$ may bond together to form a ring with the sulfur atom, $R^{400}$ and $R^{500}$ are each independently a straight $C_1$-$C_{20}$, branched or cyclic $C_3$-$C_{20}$ monovalent hydrocarbon group which may be substituted with or separated by a heteroatom; and

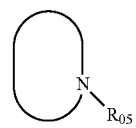

wherein general formula (U-1) is the following structure:

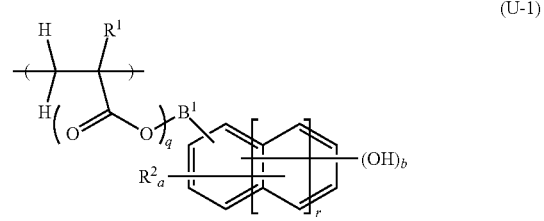
(U-1)

wherein q is 0 or 1, r is an integer of 0 to 2, $R^1$ is hydrogen, fluorine, methyl or trifluoromethyl, $R^2$ is each independently hydrogen or $C_1$-$C_6$ alkyl, $B^1$ is a single bond or $C_1$-$C_{10}$ alkylene group which may contain an ether bond, a is an integer satisfying $a \leq 5+2r-b$, and b is an integer of 1 to 3.

2. The resist composition of claim 1 wherein the anion moiety of the onium salt compound having formula (1) is selected from the following formulae (1)-1 to (1)-65, and the anion moiety of the onium salt compound having formula (2) is selected from the following formulae (2)-1 to (2)-43
(1)-1
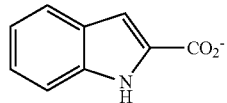
(1)-2
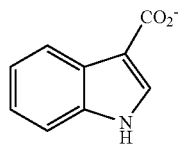
(1)-3
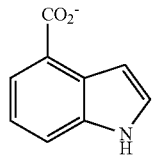
(1)-4
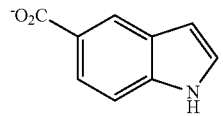
(1)-5
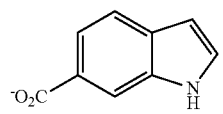
(1)-6
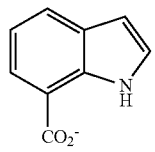
(1)-7
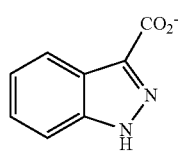
(1)-8
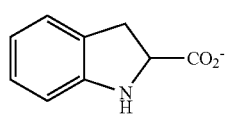
(1)-9
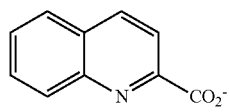
(1)-10
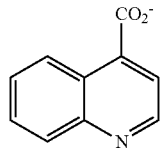
-continued
(1)-11
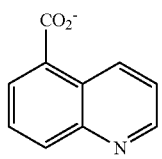
(1)-12
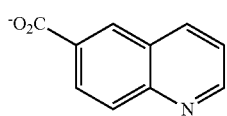
(1)-13
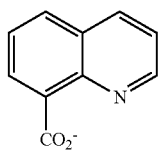
(1)-14
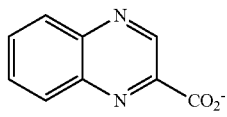
(1)-15
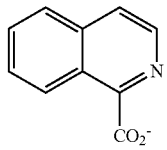
(1)-16
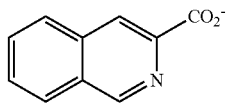
(1)-17
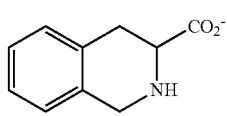
(1)-18
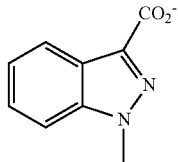
(1)-19
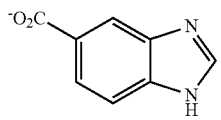
(1)-20
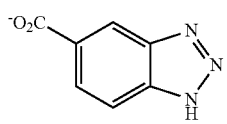
(1)-21
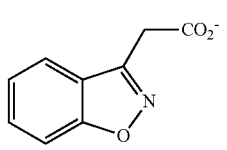

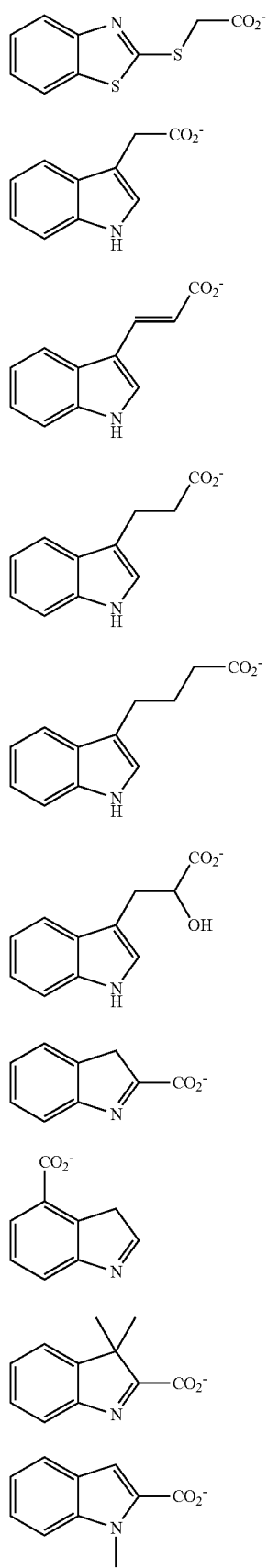
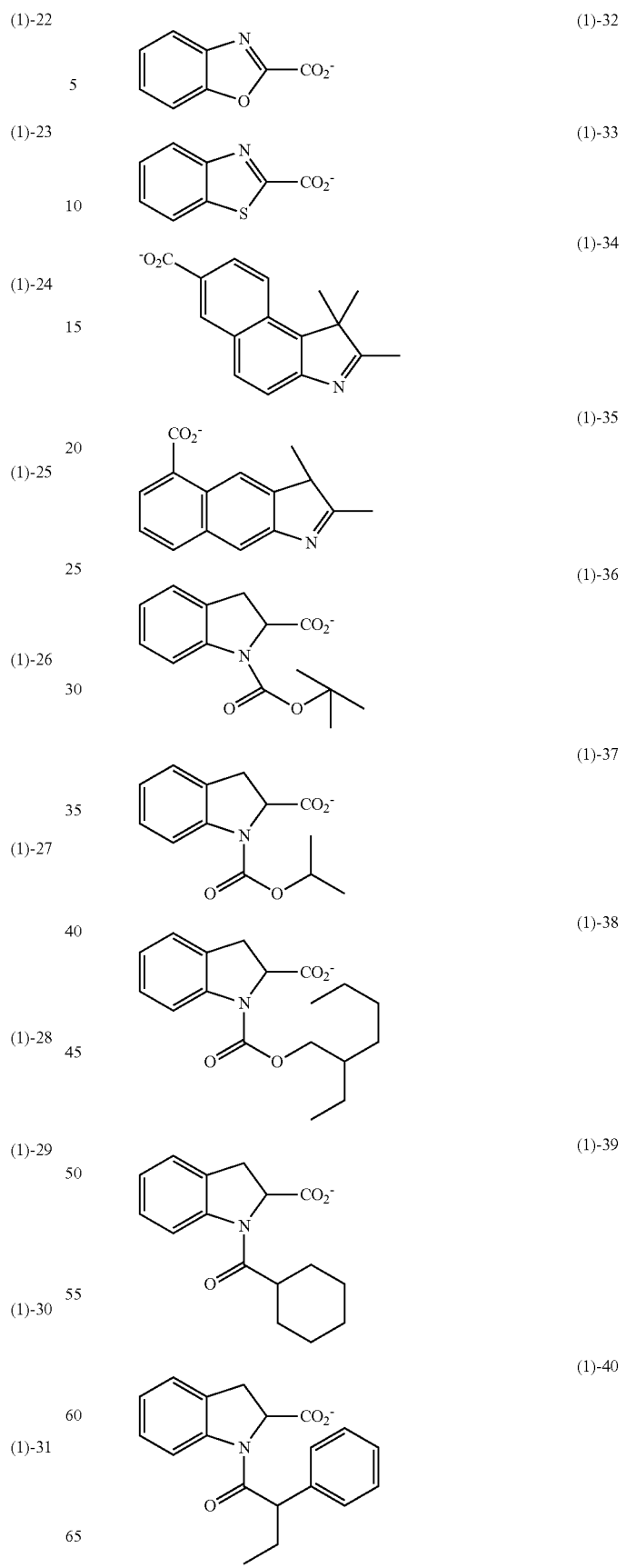

(1)-41
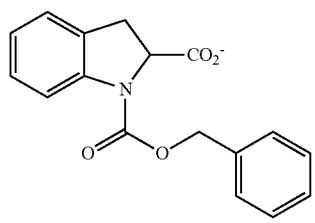
(1)-42
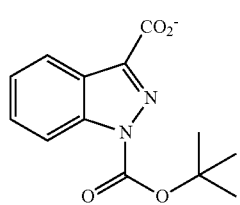
(1)-43
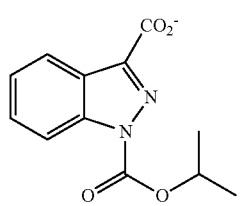
(1)-44
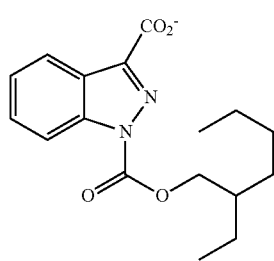
(1)-45
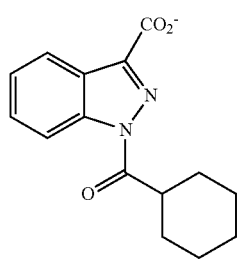
(1)-46
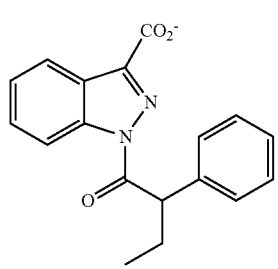
(1)-47
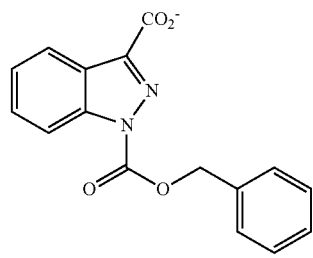
(1)-48
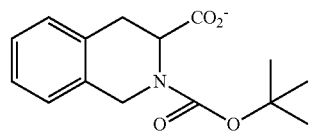
(1)-49
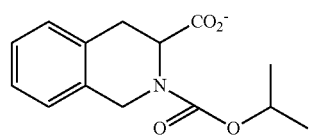
(1)-50
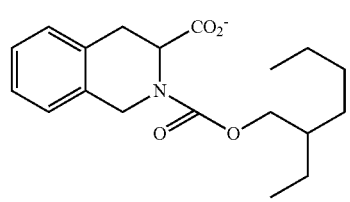
(1)-51
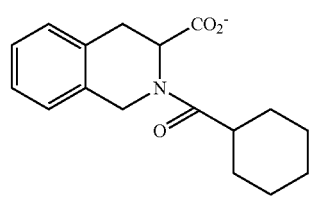
(1)-52
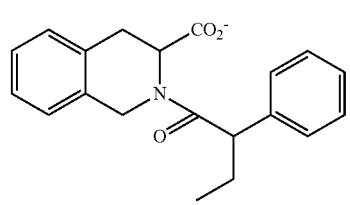
(1)-53
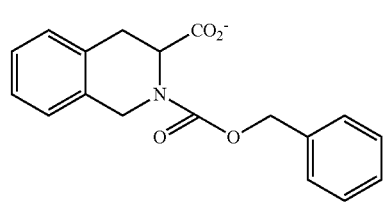
(1)-54
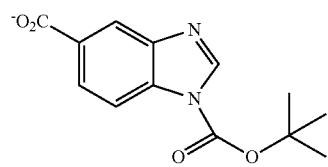

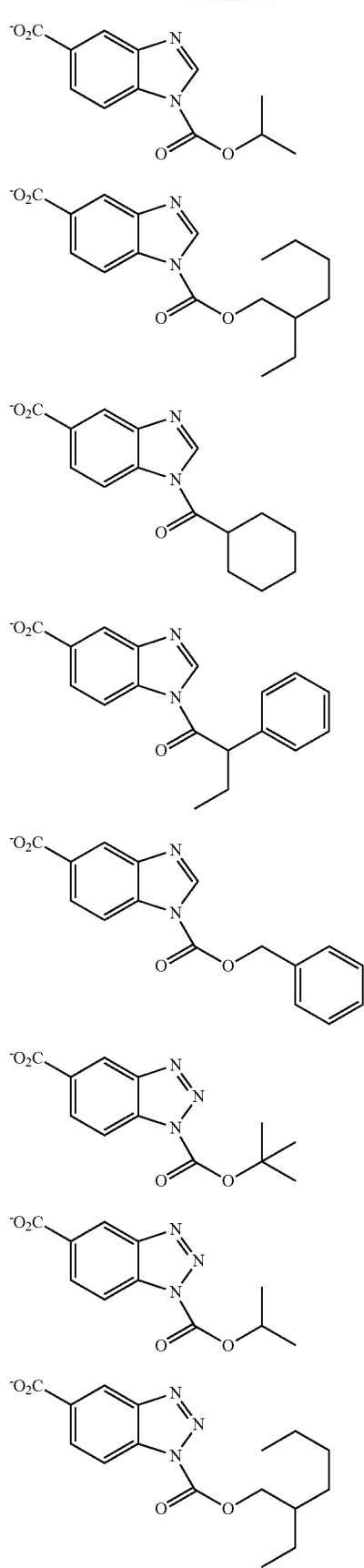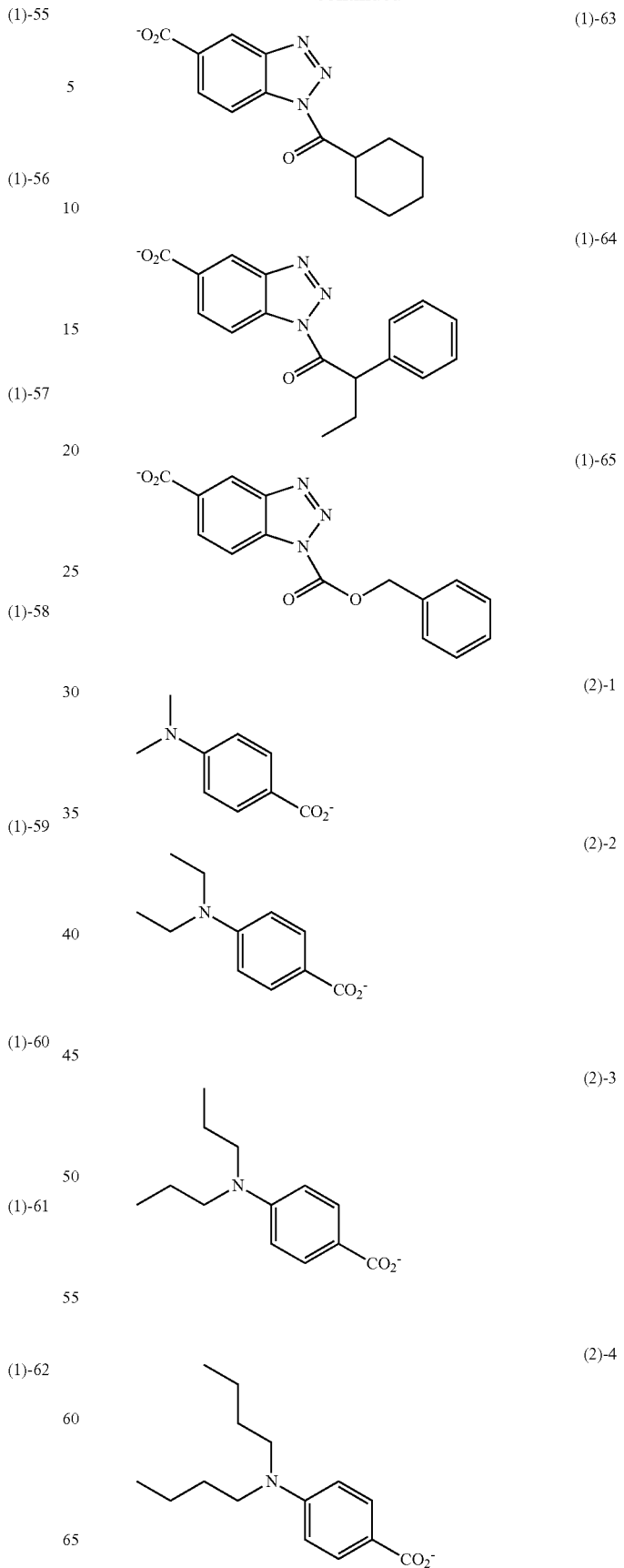

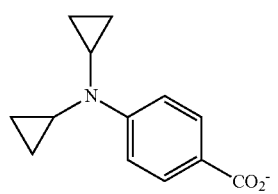 (2)-5
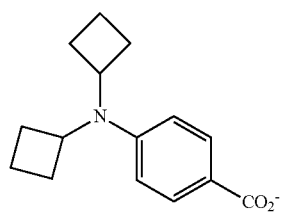 (2)-6
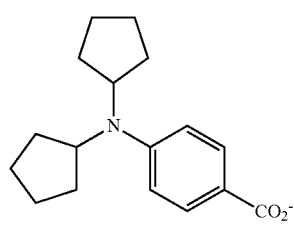 (2)-7
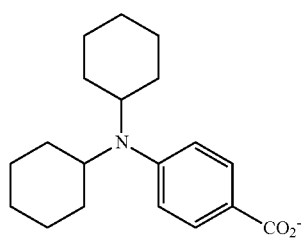 (2)-8
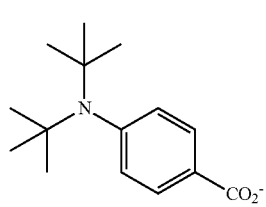 (2)-9
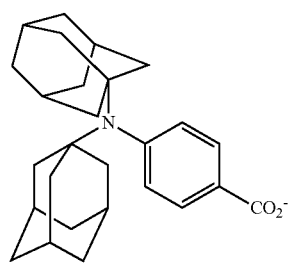 (2)-10
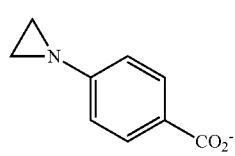 (2)-11
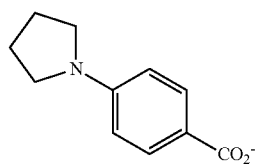 (2)-12
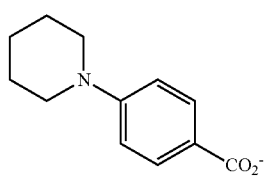 (2)-13
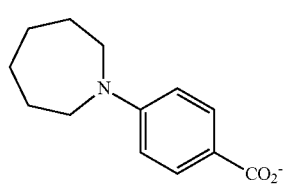 (2)-14
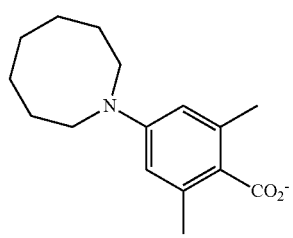 (2)-15
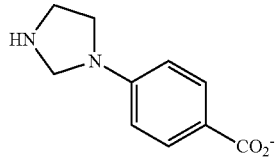 (2)-16
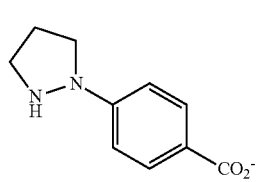 (2)-17
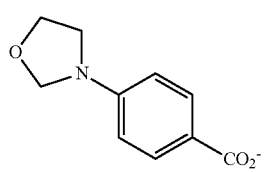 (2)-18
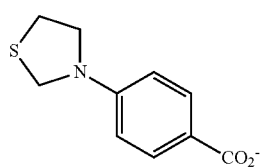 (2)-19

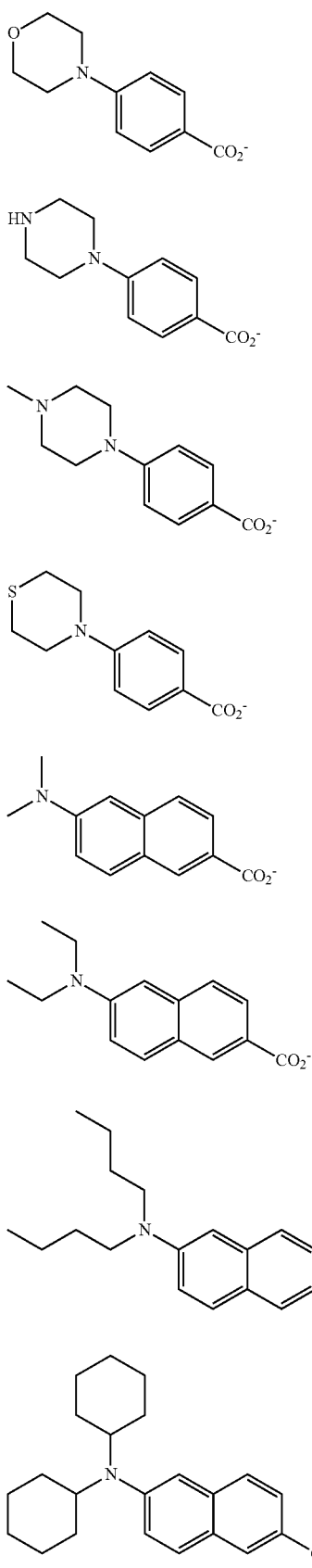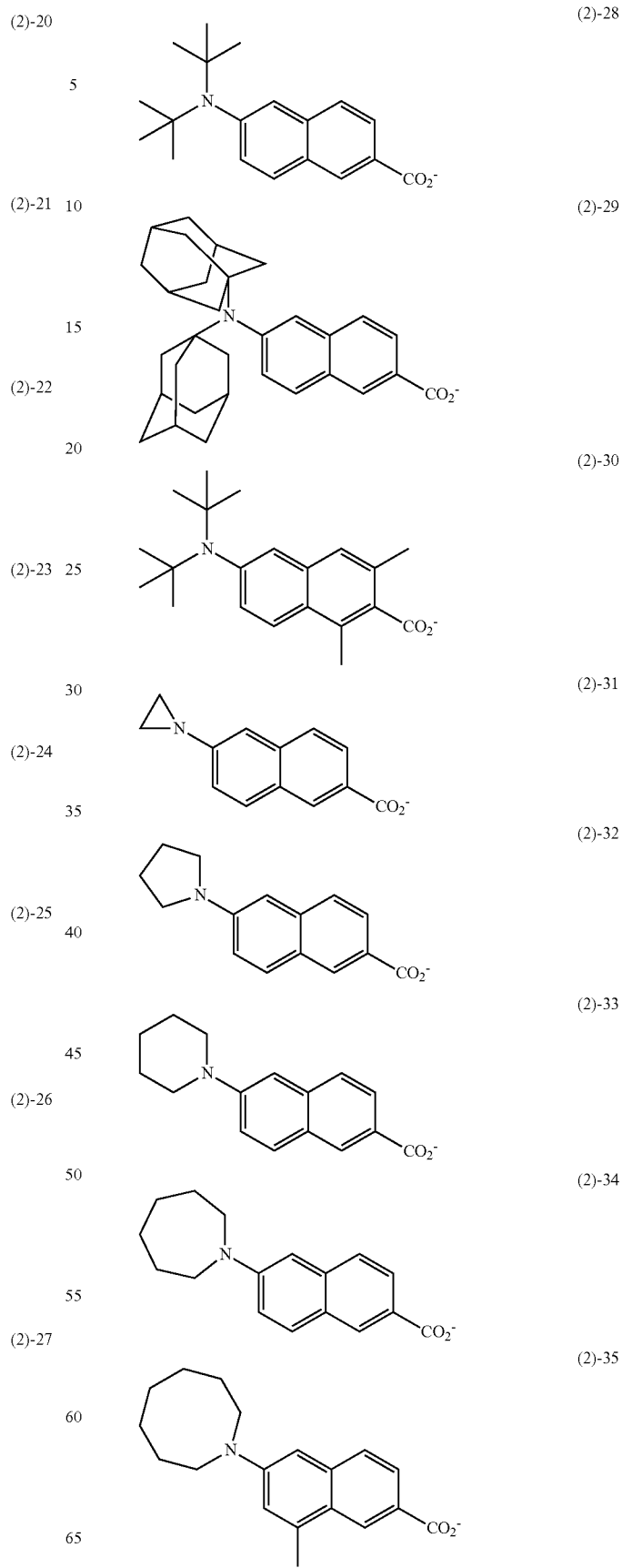

wherein s is 0 or 1, t is an integer of 0 to 2, $R^1$, $R^2$ and $B^1$ are as defined above, c is an integer satisfying c≤5+2t−e, d is 0 or 1, e is an integer of 1 to 3, X is an acid labile group when e is 1, and X is hydrogen or an acid labile group when e is 2 or 3, at least one X being an acid labile group.

4. The resist composition of claim 3 wherein the acid labile group is a tertiary alkyl group in which alkyl substituents on tertiary carbon are straight, branched or cyclic $C_1$-$C_{15}$ alkyl groups which may contain an oxygen-containing functional group, and alkyl substituents on tertiary carbon may bond together to form a ring, or an acetal group of the general formula (U-2-1), wherein $R^{24}$ is hydrogen or a straight, branched or cyclic $C_1$-$C_{10}$ alkyl group, and W is a straight, branched or cyclic $C_1$-$C_{30}$ alkyl group.

5. The resist composition of new claim 4 wherein W is a $C_7$-$C_{30}$ polycyclic alkyl group.

6. The resist composition of claim 1 wherein said resin (B) further comprises recurring units of at least one type selected from units having the general formulae (U-3) and (U-4):

wherein f is an integer of 0 to 6, $R^3$ is each independently hydrogen, an optionally halo-substituted $C_1$-$C_6$ alkyl or primary or secondary alkoxy group, or an optionally halo-substituted $C_1$-$C_7$ alkylcarbonyloxy group, g is an integer of 0 to 4, and $R^4$ is each independently hydrogen, an optionally halo-substituted $C_1$-$C_6$ alkyl or primary or secondary alkoxy group, or an optionally halo-substituted $C_1$-$C_7$ alkylcarbonyloxy group.

3. The resist composition of claim 1 wherein said resin (B) further comprises recurring units having the general formula (U-2):

7. The resist composition of claim 1 wherein said resin (B) further comprises recurring units of at least one type selected from units having the general formulae (a1), (a2) and (a3):

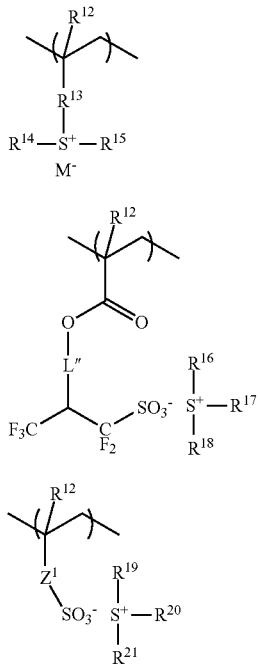

wherein $R^{12}$ is each independently hydrogen or methyl; $R^{13}$ is a single bond, phenylene, —O—$R^{22}$—, or —C(=O)—$Z^2$—$R^{22}$—, $Z^2$ is oxygen or NH, $R^{22}$ is a straight, branched or cyclic $C_1$-$C_6$ alkylene, alkenylene or phenylene group, which may contain a carbonyl (—CO—), ester (—COO—), ether (—O—), or hydroxyl moiety; L" is a single bond or —$Z^3$—C(=O)—O—, $Z^3$ is a straight, branched or cyclic $C_1$-$C_{20}$ divalent hydrocarbon group which may be substituted with or separated by a heteroatom, $Z^1$ is a single bond, methylene, ethylene, phenylene, fluorinated phenylene, —O—$R^{23}$— or —C(=O)—$Z^4$—$R^{23}$—, $Z^4$ is oxygen or NH, $R^{23}$ is a straight, branched or cyclic $C_1$-$C_6$ alkylene, alkenylene or phenylene group, which may contain a carbonyl, ester, ether, or hydroxyl moiety; M$^-$ is a non-nucleophilic counter ion; $R^{14}$, $R^{15}$, $R^{16}$, $R^{17}$, $R^{18}$, $R^{19}$, $R^{20}$, and $R^{21}$ are each independently a straight $C_1$-$C_{20}$, branched or cyclic $C_3$-$C_{20}$ monovalent hydrocarbon group in which a hydrogen atom may be substituted by a heteroatom selected from oxygen, sulfur, nitrogen and halogen or in which a heteroatom selected from oxygen, sulfur and nitrogen may intervene, so that a hydroxyl, cyano, carbonyl, ether bond, ester bond, sulfonic acid ester bond, carbonate bond, lactone ring, sultone ring, carboxylic anhydride or haloalkyl group may form or intervene, or a pair of $R^{14}$ and $R^{15}$ may bond together to form a ring with the sulfur atom, or any two or more of $R^{16}$, $R^{17}$ and $R^{18}$ or any two or more of $R^{19}$, $R^{20}$ and $R^{21}$ may bond together to form a ring with the sulfur atom.

8. The resist composition of claim 1, further comprising (D) a polymer comprising recurring units having the general formula (3), and fluorine-containing recurring units of at least one type selected from recurring units having the general formulae (4), (5), (6) and (7):

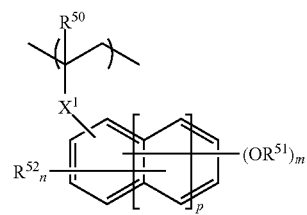

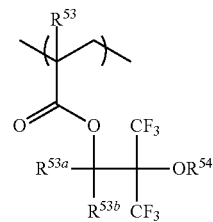

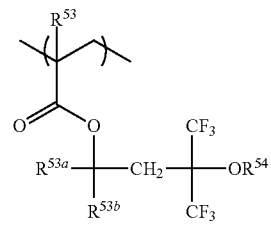

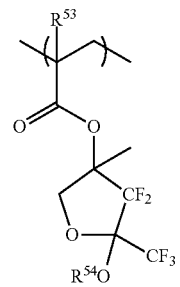

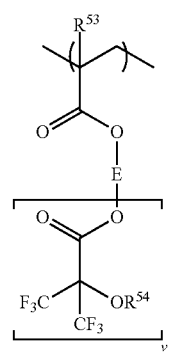

wherein $R^{50}$ is hydrogen or methyl, $R^{51}$ is hydrogen or a straight or branched $C_1$-$C_5$ monovalent hydrocarbon group which may be substituted with or separated by a heteroatom, $R^{52}$ is a straight or branched $C_1$-$C_5$ monovalent hydrocarbon group which may be substituted with or separated by a heteroatom, $R^{53}$ is each independently hydrogen, fluorine, methyl or trifluoromethyl, $R^{53a}$ and $R^{53b}$ are each independently hydrogen or a straight, branched or cyclic $C_1$-$C_{10}$ alkyl group, $R^{54}$ is each independently hydrogen, an acid labile group or a straight, branched or cyclic $C_1$-$C_{15}$ monovalent hydrocarbon or fluorinated hydrocarbon group in which an ether bond (—O—) or carbonyl moiety (—C(=O)—) may intervene in a carbon-carbon bond, m is an integer of 1 to 3, n is an integer in the range: $0 \leq n \leq 5+2k-m$, p is 0 or 1, v is an integer of 1 to 3, $X^1$ is a single bond, —C(=O)O— or —C(=O)NH—, and E is a straight, branched or cyclic $C_1$-$C_{20}$ (v+1)-valent hydrocarbon or fluorinated hydrocarbon group.

9. A pattern forming process comprising the steps of applying the resist composition of claim 1 onto a processable substrate to form a resist film, exposing patternwise the resist film to high-energy radiation, and developing the exposed resist film in an alkaline developer to form a resist pattern.

10. The process of claim 9 wherein the high-energy radiation is EUV or EB.

11. The process of claim 9 wherein the processable substrate has the outermost surface of a chromium-containing material.

12. The process of claim 9 wherein the processable substrate is a photomask blank.

* * * * *